US012623061B2

(12) United States Patent
Galdonik et al.

(10) Patent No.: US 12,623,061 B2
(45) Date of Patent: May 12, 2026

(54) SUPPORT CATHETERS AND ASSOCIATED LOADING COMPONENTS

(71) Applicant: Teleflex Life Sciences LLC, Wilmington, DE (US)

(72) Inventors: Jason Galdonik, Minneapolis, MN (US); Mark W. I. Webster, Auckland (NZ); Christopher E. Buller, Toronto (CA); Joshua Brenizer, Oak Grove, MN (US); Daniel Jindra, Andover, MN (US)

(73) Assignee: Teleflex Life Sciences LLC, Wilmington, DE (US)

( * ) Notice: Subject to any disclaimer, the term of this patent is extended or adjusted under 35 U.S.C. 154(b) by 1028 days.

(21) Appl. No.: 17/672,472

(22) Filed: Feb. 15, 2022

(65) Prior Publication Data

US 2022/0257910 A1 Aug. 18, 2022

Related U.S. Application Data

(60) Provisional application No. 63/149,510, filed on Feb. 15, 2021.

(51) Int. Cl.
A61M 25/09 (2006.01)
(52) U.S. Cl.
CPC ............................... A61M 25/0905 (2013.01)
(58) Field of Classification Search
CPC ...... A61M 25/0905; A61M 2025/0004; A61M 25/0054; A61M 25/005; A61M 25/008; A61M 2025/018
See application file for complete search history.

(56) References Cited

U.S. PATENT DOCUMENTS 4,000,739 A 1/1977 Stevens
4,166,468 A 9/1979 Haynie
(Continued)

FOREIGN PATENT DOCUMENTS

CA 2008784 C 7/2002
DE 69928825 7/2006
(Continued)

OTHER PUBLICATIONS

European Supplemental Search Report and Opinion mailed Feb. 1, 2024, in European Application No. 22753531.7.
(Continued)

*Primary Examiner* — Bhisma Mehta
*Assistant Examiner* — Marissa Taylor
(74) *Attorney, Agent, or Firm* — Dorsey & Whitney LLP

(57) ABSTRACT

Split support catheters, loading tools, and methods of use are disclosed. A support catheter can include an elongate tubular member and a push member. The tubular member can comprise a longitudinal slit configured to accommodate the exchange of various interventional devices into and out of the lumen defined by the tubular member. A loading tool can comprise a body member, a rod member, or both and can facilitate loading of the support catheter onto one or more interventional devices during a medical procedure. The support catheters can provide intravascular support to various interventional devices and can advantageously be inserted and removed without first removing an interventional device having its distal end at or near a target site within a patient's vasculature.

12 Claims, 59 Drawing Sheets

(56)                    References Cited

U.S. PATENT DOCUMENTS

| | | | |
|---|---|---|---|
| 4,289,128 A | 9/1981 | Rusch | |
| 4,402,685 A | 9/1983 | Buhler et al. | |
| 4,694,838 A | 9/1987 | Wijayarthna et al. | |
| 4,723,936 A | 2/1988 | Buchbinder et al. | |
| 4,762,129 A | 8/1988 | Bonzel | |
| 4,769,005 A | 9/1988 | Ginsburg et al. | |
| 4,771,782 A | 9/1988 | Millar | |
| 4,776,846 A | 10/1988 | Wells | |
| 4,813,930 A | 3/1989 | Elliott | |
| 4,832,028 A | 5/1989 | Patel | |
| 4,838,268 A | 6/1989 | Keith et al. | |
| 4,838,269 A | 6/1989 | Robinson et al. | |
| 4,909,252 A | 3/1990 | Goldberger | |
| 4,921,483 A | 5/1990 | Wijay et al. | |
| 4,932,413 A | 6/1990 | Shockey et al. | |
| 4,943,278 A | 7/1990 | Euteneuer et al. | |
| 4,946,440 A | 8/1990 | Hall | |
| 4,994,745 A | 2/1991 | Mizuta | |
| 5,002,531 A | 3/1991 | Bonzel | |
| 5,040,548 A | 8/1991 | Yock | |
| 5,061,273 A | 10/1991 | Yock | |
| 5,074,845 A | 12/1991 | Miraki et al. | |
| 5,088,991 A | 2/1992 | Weldon | |
| 5,098,412 A | 3/1992 | Shiu | |
| 5,102,403 A | 4/1992 | Alt | |
| 5,120,323 A | 6/1992 | Shockey et al. | |
| 5,122,125 A | 6/1992 | Deuss | |
| 5,156,594 A | 10/1992 | Keith | |
| 5,195,962 A | 3/1993 | Martin et al. | |
| 5,232,445 A | 8/1993 | Bonzel | |
| 5,234,416 A | 8/1993 | Macaulay et al. | |
| 5,257,974 A | 11/1993 | Cox | |
| 5,263,932 A | 11/1993 | David | |
| 5,267,958 A | 12/1993 | Buchbinder et al. | |
| 5,290,247 A | 3/1994 | Crittenden | |
| 5,328,472 A | 7/1994 | Steinke et al. | |
| 5,344,401 A | 9/1994 | Radisch et al. | |
| 5,350,395 A | 9/1994 | Yock | |
| 5,368,567 A | 11/1994 | Lee | |
| 5,383,853 A | 1/1995 | Jung et al. | |
| 5,395,389 A | 3/1995 | Patel | |
| 5,413,560 A | 5/1995 | Solar | |
| 5,415,639 A | 5/1995 | VandenEinde et al. | |
| 5,439,445 A | 8/1995 | Kontos | |
| 5,441,489 A | 8/1995 | Utsumi et al. | |
| 5,445,624 A | 8/1995 | Jimenez | |
| 5,445,625 A | 8/1995 | Voda | |
| 5,451,209 A | 9/1995 | Ainsworth et al. | |
| 5,472,425 A | 12/1995 | Teirstein | |
| 5,484,409 A | 1/1996 | Atkinson et al. | |
| 5,489,278 A | 2/1996 | Abrahamson | |
| 5,527,292 A | 6/1996 | Adams et al. | |
| 5,531,721 A | 7/1996 | Pepin et al. | |
| 5,545,149 A | 8/1996 | Brin et al. | |
| 5,549,553 A | 8/1996 | Ressemann et al. | |
| 5,562,620 A | 10/1996 | Klein et al. | |
| 5,567,203 A | 10/1996 | Euteneuer et al. | |
| 5,571,087 A | 11/1996 | Ressemann et al. | |
| 5,578,009 A | 11/1996 | Kraus et al. | |
| 5,599,326 A | 2/1997 | Carter | |
| 5,609,574 A | 3/1997 | Kaplan et al. | |
| 5,620,417 A | 4/1997 | Jang et al. | |
| 5,626,600 A | 5/1997 | Horzewski et al. | |
| 5,649,909 A | 7/1997 | Cornelius | |
| 5,658,263 A | 8/1997 | Dang et al. | |
| 5,658,309 A | 8/1997 | Berthiaume et al. | |
| 5,690,613 A | 11/1997 | Verbeek | |
| 5,704,926 A | 1/1998 | Sutton | |
| 5,720,300 A | 2/1998 | Fagan et al. | |
| 5,720,724 A | 2/1998 | Ressemann et al. | |
| 5,738,667 A | 4/1998 | Solar | |
| 5,743,876 A | 4/1998 | Swanson | |
| 5,772,639 A | 6/1998 | Lampropoulos et al. | |
| 5,772,642 A | 6/1998 | Ciamacco et al. | |
| 5,776,141 A | 7/1998 | Klein et al. | |
| 5,785,685 A | 7/1998 | Kugler et al. | |
| 5,792,124 A | 8/1998 | Horrigan et al. | |
| 5,817,072 A | 10/1998 | Lampropoulos et al. | |
| 5,827,229 A | 10/1998 | Auth et al. | |
| 5,843,022 A | 12/1998 | Willard et al. | |
| 5,860,963 A | 1/1999 | Azam et al. | |
| 5,876,373 A | 3/1999 | Giba et al. | |
| 5,891,056 A | 4/1999 | Ramzipoor | |
| 5,902,290 A | 5/1999 | Peacock, I et al. | |
| 5,911,715 A | 6/1999 | Berg et al. | |
| 5,944,712 A | 8/1999 | Frassica et al. | |
| 5,947,925 A | 9/1999 | Ashiya et al. | |
| 5,961,510 A | 10/1999 | Fugoso et al. | |
| 5,980,486 A | 11/1999 | Enger | |
| 6,027,461 A | 2/2000 | Walker et al. | |
| 6,036,682 A | 3/2000 | Lange et al. | |
| 6,042,578 A | 3/2000 | Dinh et al. | |
| 6,071,273 A | 6/2000 | Euteneuer et al. | |
| 6,096,073 A | 8/2000 | Webster et al. | |
| 6,102,890 A | 8/2000 | Stivland et al. | |
| 6,132,824 A | 10/2000 | Hamlin | |
| 6,159,195 A | 12/2000 | Ha et al. | |
| 6,179,828 B1 | 1/2001 | Mottola et al. | |
| 6,190,358 B1 | 2/2001 | Fitzmaurice et al. | |
| 6,193,686 B1 | 2/2001 | Estrada et al. | |
| 6,199,262 B1 | 3/2001 | Martin | |
| 6,217,527 B1 | 4/2001 | Selmon et al. | |
| 6,231,563 B1 | 5/2001 | White et al. | |
| 6,270,465 B1 | 8/2001 | Keith et al. | |
| 6,290,693 B1 | 9/2001 | Jung, Jr. et al. | |
| 6,299,628 B1 | 10/2001 | Harrison et al. | |
| 6,338,725 B1 | 1/2002 | Hermann et al. | |
| 6,398,773 B1 | 6/2002 | Bagaoisan et al. | |
| 6,409,863 B1 | 6/2002 | Williams et al. | |
| 6,443,912 B1 | 9/2002 | Mazzola et al. | |
| 6,475,195 B1 | 11/2002 | Voda | |
| 6,488,655 B1 | 12/2002 | Wantink et al. | |
| 6,503,223 B1 | 1/2003 | Sekido et al. | |
| 6,503,353 B1 | 1/2003 | Peterson et al. | |
| 6,548,010 B1 | 4/2003 | Stivland et al. | |
| 6,575,958 B1 | 6/2003 | Happ et al. | |
| 6,591,472 B1 | 7/2003 | Noone et al. | |
| 6,595,952 B2 | 7/2003 | Forsberg | |
| 6,596,020 B2 | 7/2003 | Vardi et al. | |
| 6,610,068 B1 | 8/2003 | Yang | |
| 6,610,069 B2 | 8/2003 | Euteneuer et al. | |
| 6,620,149 B1 | 9/2003 | Lenz et al. | |
| 6,635,029 B1 | 10/2003 | Venturelli | |
| 6,638,268 B2 | 10/2003 | Niazi | |
| 6,648,874 B2 | 11/2003 | Parisi et al. | |
| 6,682,536 B2 | 1/2004 | Vardi et al. | |
| 6,689,144 B2 | 2/2004 | Gerberding | |
| 6,692,483 B2 | 2/2004 | Vardi et al. | |
| 6,706,018 B2 | 3/2004 | Westlund et al. | |
| 6,733,487 B2 | 5/2004 | Keith et al. | |
| 6,755,812 B2 | 6/2004 | Peterson et al. | |
| 6,860,876 B2 | 3/2005 | Chen | |
| 6,869,417 B1 | 3/2005 | Walters et al. | |
| 6,997,908 B2 | 2/2006 | Carrillo, Jr. et al. | |
| 7,169,162 B2 | 1/2007 | Garakani | |
| 7,232,452 B2 | 6/2007 | Adams et al. | |
| 7,294,124 B2 | 11/2007 | Fidenschink | |
| 7,374,560 B2 | 5/2008 | Ressemann et al. | |
| 7,422,579 B2 | 9/2008 | Wahr et al. | |
| 7,544,201 B2 | 6/2009 | Pepper | |
| 7,604,612 B2 | 10/2009 | Ressemann et al. | |
| 7,697,996 B2 | 4/2010 | Manning et al. | |
| 7,717,899 B2 | 5/2010 | Bowe et al. | |
| 7,736,355 B2 | 6/2010 | Itou et al. | |
| 7,762,984 B2 | 7/2010 | Kumoyama et al. | |
| 7,763,012 B2 | 7/2010 | Petrick et al. | |
| 7,959,603 B2 | 6/2011 | Wahr et al. | |
| 8,048,032 B2 | 11/2011 | Root et al. | |
| 8,142,413 B2 | 3/2012 | Root et al. | |
| 8,292,850 B2 | 10/2012 | Root et al. | |
| 8,292,872 B2 | 10/2012 | Soetermans | |
| 8,613,722 B2 | 12/2013 | Lee et al. | |
| 8,721,624 B2 | 5/2014 | Wilson et al. | |
| 8,814,890 B2 | 8/2014 | Miyata et al. | |

(56)  References Cited

U.S. PATENT DOCUMENTS

| | | |
|---|---|---|
| RE45,380 E | 2/2015 | Root et al. |
| 8,996,095 B2 | 3/2015 | Anderson et al. |
| 9,144,662 B2 | 9/2015 | Caprio et al. |
| RE45,760 E | 10/2015 | Root et al. |
| RE45,776 E | 10/2015 | Root et al. |
| 9,352,123 B2 | 5/2016 | Zhou et al. |
| RE46,116 E | 8/2016 | Root et al. |
| 9,486,611 B2 | 11/2016 | Petersen et al. |
| 10,173,029 B2 | 1/2019 | Webster et al. |
| RE47,379 E | 5/2019 | Root et al. |
| 10,751,514 B2 | 8/2020 | Brenizer et al. |
| 10,946,177 B2 | 3/2021 | Peterson et al. |
| 10,953,197 B2 | 3/2021 | Brenizer et al. |
| 10,974,028 B2 | 4/2021 | Buller et al. |
| 2001/0010011 A1 | 7/2001 | Aliberto et al. |
| 2001/0016712 A1 | 8/2001 | Hamilton |
| 2002/0032432 A1 | 3/2002 | Nash et al. |
| 2002/0165598 A1 | 11/2002 | Wahr et al. |
| 2003/0130620 A1 | 7/2003 | Alokaili |
| 2003/0195546 A1 | 10/2003 | Solar et al. |
| 2003/0233117 A1 | 12/2003 | Adams et al. |
| 2004/0010280 A1 | 1/2004 | Adams et al. |
| 2004/0127927 A1 | 7/2004 | Adams |
| 2004/0133185 A1 | 7/2004 | Nash et al. |
| 2004/0236215 A1 | 11/2004 | Mihara et al. |
| 2005/0004523 A1 | 1/2005 | Osborne et al. |
| 2005/0015073 A1 | 1/2005 | Kataishi et al. |
| 2005/0148950 A1 | 7/2005 | Windheuser et al. |
| 2005/0182437 A1 | 8/2005 | Bonnette et al. |
| 2005/0267408 A1 | 12/2005 | Grandt et al. |
| 2005/0267442 A1 | 12/2005 | Oepen |
| 2006/0142703 A1 | 6/2006 | Carter et al. |
| 2006/0210605 A1 | 9/2006 | Chang et al. |
| 2006/0247661 A1 | 11/2006 | Richards et al. |
| 2007/0060911 A1 | 3/2007 | Webster et al. |
| 2007/0208302 A1* | 9/2007 | Webster ................... A61F 2/95 |
| | | 604/103.04 |
| 2007/0260219 A1 | 11/2007 | Root et al. |
| 2008/0082045 A1 | 4/2008 | Goldfarb et al. |
| 2008/0091137 A1 | 4/2008 | Reavill |
| 2008/0188804 A1* | 8/2008 | Jordan .................. A61M 25/00 |
| | | 604/103.04 |
| 2008/0243171 A1 | 10/2008 | Ressemann et al. |
| 2009/0005755 A1 | 1/2009 | Keith et al. |
| 2009/0264865 A1 | 10/2009 | Kawai |
| 2013/0072904 A1 | 3/2013 | Musbach et al. |
| 2013/0116701 A1 | 5/2013 | Wang et al. |
| 2013/0197483 A1 | 8/2013 | Anderson et al. |
| 2014/0012281 A1* | 1/2014 | Wang ............... A61M 25/0023 |
| | | 606/108 |
| 2014/0018773 A1 | 1/2014 | Wang et al. |
| 2014/0025004 A1 | 1/2014 | Falk et al. |
| 2014/0025043 A1 | 1/2014 | Wang et al. |
| 2014/0039461 A1 | 2/2014 | Anderson et al. |
| 2014/0052097 A1 | 2/2014 | Petersen et al. |
| 2014/0081243 A1 | 3/2014 | Zhou et al. |
| 2014/0142506 A1 | 5/2014 | Prindle et al. |
| 2014/0155801 A1 | 6/2014 | Zinn et al. |
| 2014/0171914 A1 | 6/2014 | Rowe et al. |
| 2014/0249508 A1 | 9/2014 | Wang et al. |
| 2014/0276618 A1 | 9/2014 | Di Caprio et al. |
| 2014/0358123 A1 | 12/2014 | Ueda et al. |
| 2015/0051633 A1 | 2/2015 | Sina |
| 2015/0151090 A1 | 6/2015 | Sutton et al. |
| 2016/0346515 A1 | 12/2016 | Buller et al. |
| 2017/0028170 A1 | 2/2017 | Ho |
| 2017/0296221 A1* | 10/2017 | Di Caprio ............. A61M 25/01 |
| 2017/0296369 A1 | 10/2017 | Dorn et al. |
| 2018/0116684 A1* | 5/2018 | Garrison ............. A61B 17/221 |
| 2018/0161547 A1 | 6/2018 | Brenizer et al. |
| 2018/0193042 A1* | 7/2018 | Wilson ............. A61B 17/12136 |
| 2019/0247619 A1 | 8/2019 | Brenizer et al. |
| 2019/0358434 A1 | 11/2019 | Fuller et al. |
| 2020/0129734 A1* | 4/2020 | Di Caprio ........... A61M 25/008 |
| 2020/0188633 A1 | 6/2020 | Cottone |
| 2020/0338317 A1 | 10/2020 | Brenizer et al. |
| 2021/0008342 A1 | 1/2021 | Buller et al. |
| 2021/0008343 A1 | 1/2021 | Brenizer et al. |
| 2021/0008355 A1 | 1/2021 | Peterson et al. |
| 2022/0096795 A1 | 3/2022 | Brenizer |

FOREIGN PATENT DOCUMENTS

| | | |
|---|---|---|
| EP | 0282143 A1 | 9/1988 |
| EP | 0377453 A1 | 7/1990 |
| EP | 0313558 B1 | 1/1991 |
| EP | 0380873 B1 | 5/1994 |
| EP | 0365993 B1 | 12/1994 |
| EP | 0881921 A1 | 12/1998 |
| EP | 1084728 A1 | 3/2001 |
| EP | 1400208 A1 | 3/2004 |
| EP | 0992260 B1 | 9/2007 |
| JP | h0248522 B | 7/1993 |
| JP | H10507095 A | 7/1998 |
| JP | 2004275435 A | 10/2004 |
| JP | 2009524490 A | 7/2009 |
| JP | 2012135379 A | 7/2012 |
| JP | 2017533012 A | 11/2017 |
| JP | 2019530519 A | 10/2019 |
| JP | 2020192267 A | 12/2020 |
| WO | 1984003633 A1 | 9/1984 |
| WO | 1996001604 A1 | 1/1996 |
| WO | 1997037713 A1 | 10/1997 |
| WO | 1998036709 A1 | 8/1998 |
| WO | 1999034749 A1 | 7/1999 |
| WO | 2000012166 A1 | 3/2000 |
| WO | 2000024451 A9 | 11/2000 |
| WO | 2005030308 A1 | 4/2005 |
| WO | 2007089570 A2 | 8/2007 |
| WO | 2014028898 A2 | 2/2014 |
| WO | 2016073563 A1 | 5/2016 |
| WO | 2016191415 A1 | 12/2016 |
| WO | 2017019900 A1 | 2/2017 |
| WO | 2018067824 A1 | 4/2018 |
| WO | 2020171878 A1 | 8/2020 |

OTHER PUBLICATIONS

Petition for Inter Partes Review, IPR 2020-00134, of U.S. Pat. No. Re. 45,760, dated Nov. 13, 2019, 100 pages.

Petition for Inter Partes Review, IPR 2020-00135, of U.S. Pat. No. Re. 45,776, dated Nov. 14, 2019, 96 pages.

Petition for Inter Partes Review, IPR 2020-00136, of U.S. Pat. No. Re. 45,776, dated Nov. 14, 2019, 87 pages.

Petition for Inter Partes Review, IPR 2020-00137, of U.S. Pat. No. Re. 47,379, dated Nov. 12, 2019, 102 pages.

Petition for Inter Partes Review, IPR 2020-00138, of U.S. Pat. No. Re. 47,379, dated Nov. 12, 2019, 98 pages.

Petition for Inter Partes Review, IPR2020-01341, of U.S. Pat. No. 8,142,413 dated Jul. 30, 2020, 112 pages.

Petition for Inter Partes Review, IPR2020-01342, of U.S. Pat. No. 8,142,413, dated Jul. 30, 2020, 89 pages.

Petition for Inter Partes Review, IPR2020-01343, of U.S. Pat. No. Re. 46,116, dated Jul. 31, 2020, 96 pages.

Petition for Inter Partes Review, IPR2020-01344, of U.S. Pat. No. Re. 46,116, dated Jul. 31, 2020, 93 pages.

U.S. Appl. No. 60/762,304, filed Jan. 26, 2006, 16 pages.

PTAB Final Written Decision for IPR2020-01341 of U.S. Pat. No. 8,142,413, dated Feb. 7, 2022, 59 pages.

PTAB Final Written Decision for IPR2020-01342 of U.S. Pat. No. 8,142,413, dated Feb. 7, 2022, 31 pages.

PTAB Final Written Decision for IPR2020-01343 of U.S. Pat. No. Re. 46,116, dated Feb. 23, 2022, 73 pages.

PTAB Final Written Decision for IPR2020-01344 of U.S. Pat. No. Re. 46,116, dated Feb. 23, 2022, 60 pages.

*QXMedical, LLC* v. *Vascular Solutions, Inc.*, D. Minn., No. 17-cv-01969: U.S. District Court, "Expert Report of Brian Brown re Invalidity," dated Jan. 4, 2019, 251 pages.

*QXMedical, LLC* v. *Vascular Solutions, Inc.*, D. Minn., No. 17-cv-01969: Defendant Vascular Solutions, Inc.'s Responsive Prior Art Statement, dated Dec. 8, 2017, 315 pages.

(56)　　　　　References Cited

OTHER PUBLICATIONS

*QXMedical, LLC* v. *Vascular Solutions, Inc.*, D. Minn., No. 17-cv-01969: Order dated Oct. 2, 2019, 42 pages.
*QXMedical, LLC* v. *Vascular Solutions, Inc.*, D. Minn., No. 17-cv-01969: QXMedical, LLC Prior Art Statement, dated Oct. 30, 2017, 355 pages.
*QXMedical, LLC* v. *Vascular Solutions, Inc.*, D. Minn., No. 17-cv-01969: QXMédical, LLC's "Opening Claim Construction Memorandum" (Mar. 14, 2018), D.I. 56.
*QXMedical, LLC* v. *Vascular Solutions, Inc.*, D. Minn., No. 17-cv-01969: Defendants' Memorandum in Opposition to Plaintiff's Summary Judgment Motion and in Support of Defendants' Summary Judgment Motion, dated Apr. 30, 2019.
Sakurada, Masami et al. "Improved Performance of a New Thrombus Aspiration Catheter: Outcomes From In Vitro Experiments and a Case Presentation," Catheterization and Cardiovascular Interventions, 63:299-306 (2004).
Schobel, Wolfgang et al. "Percutaneous Coronary Interventions Using a New 5 French Guiding Catheter: Results of a Prospective Study," Catheterization and Cardiovascular Interventions, 53:308-312 (2001).
Supplementary Partial European Search Report mailed Jul. 1, 2010 in EP Application No. 07762875.8.
Takahashi et al. "New Method to Increase a Backup Support of a 6 French Guiding Coronary Catheter," Catheterization and Cardiovascular Interventions 63:452-456 (2004), 5 pages; Published online in Wiley InterScience (www.interscience.wiley.com).
Takeshita, Satoshi et al., "Percutaneous coronary intervention using a novel 4-French coronary accessor," http://www3.interscience.wiley.com/cgi-bin/fulltext/119818183/main.html,ftx_abs (Jun. 10, 2008).
Translation of the Abstract of Japanese Patent Application No. 2003-070808, 2003, 1 page.
Tully, Shawn. "Blood Feud This little piece of metal is worth $4.5 billion this year, generates more profits than a blockbuster drug, and has sparked one of the weirdest corporate battles ever. It could also save your life." CNN Money, May 31, 2004, 5 pages. Retrieved Jan. 14, 2019 on the Internet: https://money.cnn.com/magazines/fortune/fortune_archive/2004/05/31/370693/index.htm.
Urban, Phillip et al. "Coronary Stenting Through 6 French Guiding Catheters," Catheterization and Cardiovascular Diagnosis, 28:263-266 (1993).
*Vascular Solutions LLC et al* v. *Medtronic, Inc.*, U.S. District Court case 19:cv-01760-PJS-TNL: Declaration of Dr. Paul Zalesky in Opposition to Motion for Preliminary Injunction, dated Nov. 15, 2019, 48 pages.
*Vascular Solutions LLC et al* v. *Medtronic, Inc.*, U.S. District Court case 19:cv-01760-PJS-TNL: Declaration of Peter Keith in Support of Plaintiffs' Motion for Preliminary Injunction, Jul. 12, 2019, 53 pages.
*Vascular Solutions LLC et al* v. *Medtronic, Inc.*, U.S. District Court case 19:cv-01760-PJS-TNL: Defendants' Opposition to Plaintiffs' Second Motion for a Preliminary Injunction (redacted), dated Dec. 27, 2021, 61 pages.
*Vascular Solutions LLC et al* v. *Medtronic, Inc.*, U.S. District Court case 19:cv-01760-PJS-TNL: Deposition of Peter Keith of Oct. 16, 2019, 126 pages.
*Vascular Solutions LLC et al* v. *Medtronic, Inc.*, U.S. District Court case 19:cv-01760-PJS-TNL: Plaintiffs' Reply Brief in Support of their Second Motion for Preliminary Injunction (redacted), dated Jan. 10, 2022, 27 pages.
*Vascular Solutions LLC et al* v. *Medtronic, Inc.*, U.S. District Court case 19:cv-01760-PJS-TNL: Plaintiffs' Memorandum in Support of Motion for Preliminary Injunction (redacted), dated Oct. 11, 2019, 36 pages.
*Vascular Solutions LLC et al* v. *Medtronic, Inc.*, U.S. District Court case 19:cv-01760-PJS-TNL: Second Declaration of Peter Keith in Support of Plaintiff's Motion for Preliminary Injunction, dated Dec. 6, 2019, 23 pages.

Vascular Solutions, Inc. "GuideLiner V3 catheter: Guide Extension Catheter with Half-Pipe Technology" [Brochure], Dec. 2013, Minneapolis, MN.
*Vascular Solutions, Inc.* v. *Boston Scientific Corporation*, District Court Case 0:13-cv-01172 (JRT-SER): Declaration of Anthony C. Vrba, Dated Jul. 8, 2013, 4 Pgs.
*Vascular Solutions, Inc.* v. *Boston Scientific Corporation*, District Court Case 0:13-cv-01172 (JRT-SER): Declaration of Howard Root in Support of Plaintiff's Motion for Preliminary Injunction, Dated Jun. 10, 2013, 55 pgs.
*Vascular Solutions, Inc.* v. *Boston Scientific Corporation*, District Court Case 0:13-cv-01172 (JRT-SER): Declaration of Tony J. Demartini, M.D., Dated Jul. 8, 2013, 3 pgs.
*Vascular Solutions, Inc.* v. *Boston Scientific Corporation*, District Court Case 0:13-cv-01172 (JRT-SER): Defendant, Boston Scientific Corporation's First Amended Prior Art Statement, dated Apr. 25, 2014.
*Vascular Solutions, Inc.* v. *Boston Scientific Corporation*, District Court Case 0:13-cv-01172 (JRT-SER): Defendant, Boston Scientific Corporation's Prior Art Statement, dated Dec. 20, 2013.
*Vascular Solutions, Inc.* v. *Boston Scientific Corporation*, District Court Case 0:13-cv-01172 (JRT-SER): Plaintiff, Vascular Solutions, Inc.'s Response to Defendant Boston Scientific Corporation's Prior Art Statement, Dated Jan. 23, 2014.
*Vascular Solutions, Inc.* v. *Boston Scientific Corporation*, District Court Case 0:13-cv-01172 (JRT-SER): Second Declaration of Howard Root in Support of Plaintiff's Motion for Preliminary Injunction, Dated Jul. 24, 2013, 22 Pgs.
Williams, David et al. "Percutaneous Coronary Intervention in the Current Era Compared with 1985-1986," Circulation, Dec. 12, 2000, pp. 2945-2951.
Yokoyama, Jin et al. "Feasibility and safety of thrombectomy with TVAC aspiration catheter system for patients with acute myocardial infarction," Heart Vessels (2006) 21:1-7.
PCT International Search Report mailed Jun. 21, 2022 in PCT application No. PCT/US2022/016469 filed Feb. 15, 2022.
PCT Written Opinion mailed Jun. 21, 2022 in PCT application No. PCT/US2022/016469 filed Feb. 15, 2022.
Alegria, Jorge R; Holmes, David; and Topol, Eric J. "Textbook of Interventional Cardiology," Saunders Elseveir, 5th Edition, 2008, p. 277-280.
Ashikaga et al, "Difficult Stent Deliver: Use of an Aspiration Catheter as a Sheat," Catheterization and Cardiovascular Interventions, 71:909-912 (2008).
ASTM, "Standard Test Methods for Flexural Properties of Unreinforced and Reinforced Plastics and Electrical Insulating Materials," Designation: D790-03, 2003, 11 pages.
Baim et al., "Randomized Trial of a Distal Embolic Protection Device During Percutaneous Intervention of Saphenous Vein Aorto-Coronary Bypass Grafts," Clinical Investigation and Reports, 2002, 6 pages.
Bertrand, Michel E. "The Evolution of Cardiac Catheterization and Interventional Cardiology," European Society of Cardiology, 2006, 10 pages.
Bonzel, T. et al. "The Sliding Rail System (Monorail): Description of a New Technique for Intravascular Instrumentation and its Application to Coronary Angioplasty," Z. Kardiol. 76, Supp. 6 (1987), pp. 119-122.
Boston Scientific, "Summary of Safety and Effectiveness Data," Taxus™ Express2™ Drug-Eluting Coronary Stent System (Mar. 4, 2004).
Cordis, "Instructions for Use—Cypher™ Sirolimus-eluting Coronary Stent on Raptor™ Over-the-Wire Delivery System," Apr. 2003, 20 pages.
Declaration of Sylvia Hall-Ellis, Ph.D., dated Nov. 6, 2019.
Dispatch—Monorail®-GEX™ Guidewire Exchange Catheter Brochure, 1 page.
Dorros et al., "Coronary Angioplasty in Patients with Prior Coronary Artery Bypass Surgery: All Prior Coronary Artery Bypass Surgery Patients and Patients More Than 5 Years After Coronary Bypass Surgery," Cardiology Clinics, vol. 7, No. 4, Nov. 1989, 14 pages.

(56) References Cited

OTHER PUBLICATIONS

EP search report mailed Apr. 16, 2018, in European Application No. 17193571.1 filed Sep. 27, 2017.

Feldman. "Coronary Angioplasty Using New 6 French Guiding Catheters," Catheterization and Cardiovascular Diagnosis 23:93-99 (1991).

File history for U.S. Appl. No. 12/824,734, now U.S. Pat. No. 8,142,413.

File history for U.S. Appl. No. 14/195,413, now U.S. Pat. No. Re. 45,776.

File history for U.S. Appl. No. 11/416,629, now U.S. Pat. No. 8,048,032.

File history for U.S. Appl. No. 13/359,059, now U.S. Pat. No. 8,292,850.

File history for U.S. Appl. No. 14/070,161, now U.S. Pat. No. Re. 45,380.

File history for U.S. Appl. No. 14/195,385, now U.S. Pat. No. Re. 45,760.

File history for U.S. Appl. No. 14/195,435, now U.S. Pat. No. Re. 46,116.

File history for U.S. Appl. No. 14/984,273, now U.S. Pat. No. Re. 47,379.

Grossman, "Historical Perspective and Present Practice of Cardiac Catheterization," Grossman's Cardiac Catheterization, Angiography, and Intervention, 2000, 213 pages.

Iqbal et al. "Coronary stents: historical development, current status and future directions," British Medical Bulletin, 2013, 106: 193-211.

Iserson, Kenneth. "J.-F.-B.Charrière: the Man Behind the "French" Gauge," Journal of Emergency Medicine, vol. 5, 1987, pp. 545-548.

Japanese Office Action for co-pending Japanese Patent Application No. 2008-552430 dated Jan. 2012 (6 pages).

Kern, Morton. "The Interventional Cardiac Catheterization Handbook, Second Edition," 2004, 63 pages.

Kucklick, Theodore. The Medical Device R & D Handbook, 2006, 328 pages.

Limbruno, Ugo et al., "Mechanical Prevention of Distal Embolization During Primary Angioplasty," Circulation, Jul. 15, 2003, pp. 171-176.

Markman Order in QXMedical, LLC v. Vascular Solutions, Inc., D. Minn., No. 17-cv-01969 (Oct. 30, 2018), D.I. 102.

McGraw-Hill Dictionary of Scientific and Technical Terms Fifth Edition, definition of Flexural Modulus, 1994, 3 pages.

Meads, C. et al., "Coronary artery stents in the treatment of ischaemic heart disease: a rapid and systematic review," Health Technology Assessment, vol. 4, No. 23, 2000, 165 pages.

Medtronic, Inc. et al v. Teleflex Innovations S.A.R.L., U.S. Court of Appeals for the Federal Circuit case 21-2356: Appellants' Opening Brief, Appeals from PTAB Nos. IPR-2020-00126, IPR2020-00128, IPR2020-00132, IPR2020-00135, IPR2020-00137, dated Mar. 9, 2022, 581 pages.

Medtronic, Inc. et al v. Teleflex Innovations S.A.R.L., U.S. Court of Appeals for the Federal Circuit case 21-2357: Appellants' Opening Brief, Appeals from PTAB Nos. IPR-2020-00127, IPR2020-00130, IPR2020-00136, dated Mar. 9, 2022, 372 pages.

Medtronic, Inc. et al v. Teleflex Innovations S.A.R.L., U.S. Court of Appeals for the Federal Circuit case 21-2359: Appellants' Opening Brief, Appeals from PTAB Nos. IPR-2020-00129, IPR2020-00134, IPR2020-00138, dated Mar. 9, 2022, 332 pages.

Mehan, Vivek et al., "Coronary Angioplasty Through 4 French Diagnostic Catheters," Catheterization and Cardiovascular Diagnosis, vol. 30, 1993, pp. 22-26.

Metz, Damien et al. "Comparison of 6F with 7F and 8F guiding catheters for elective coronary angioplasty: Results of a prospective, multicenter, randomized trial," American Heart Journal. vol. 134, No. 1, pp. 132-137.

Nordenstrom, Bjorn. "New Instruments for Catheterization and Angiocardiography," New Instruments for Catheterization and Angiocardiography, vol. 85, Aug. 1965, pp. 256-259.

Ozaki, Yukio, et al. "New Stent Technologies," Progress in Cardiovascular Diseases, vol. 39, No. 2, Sep./Oct. 1996, pp. 129-140.

PCT International Search Report mailed Sep. 1, 2016 in connection with PCT Application No. PCT/US2016/033904 filed May 24, 2016.

PCT International Search Report mailed Sep. 19, 2008 in PCT Appln. PCT/US07/02149.

PCT International Search Report mailed Apr. 29, 2019, in PCT application No. PCT/US2019/016235.

PCT Written Opinion mailed Sep. 1, 2016 in connection with PCT Application No. PCT/US2016/033904 filed May 24, 2016.

Petition for Inter Partes Review, IPR 2020-00126, of U.S. Pat. No. 8,048,032, dated Nov. 12, 2019, 93 pages.

Petition for Inter Partes Review, IPR 2020-00127, of U.S. Pat. No. 8,048,032, dated Nov. 12, 2019, 89 pages.

Petition for Inter Partes Review, IPR 2020-00128, of U.S. Pat. No. Re. 45,380, dated Nov. 12, 2019, 93 pages.

Petition for Inter Partes Review, IPR 2020-00129, of U.S. Pat. No. Re. 45,380, dated Nov. 14, 2019, 101 pages.

Petition for Inter Partes Review, IPR 2020-00130, of U.S. Pat. No. Re. 45,380, dated Nov. 12, 2019, 90 pages.

Petition for Inter Partes Review, IPR 2020-00131, of U.S. Pat. No. Re. 45,380, dated Nov. 14, 2019, 85 pages.

Petition for Inter Partes Review, IPR 2020-00132, of U.S. Pat. No. Re. 45,760, dated Nov. 13, 2019, 97 pages.

Petition for Inter Partes Review, IPR 2020-00133, of U.S. Pat. No. Re. 45,760, dated Nov. 13, 2019, 89 pages.

First Office Action issued in China and its English translation, CN Application No. 2025121001685950, dated Dec. 10, 2025, 17 pgs.

First Office Action issued in Japan and its English translation, JP Application No. 2025-003736, dated Jan. 5, 2026, 6 pgs.

* cited by examiner

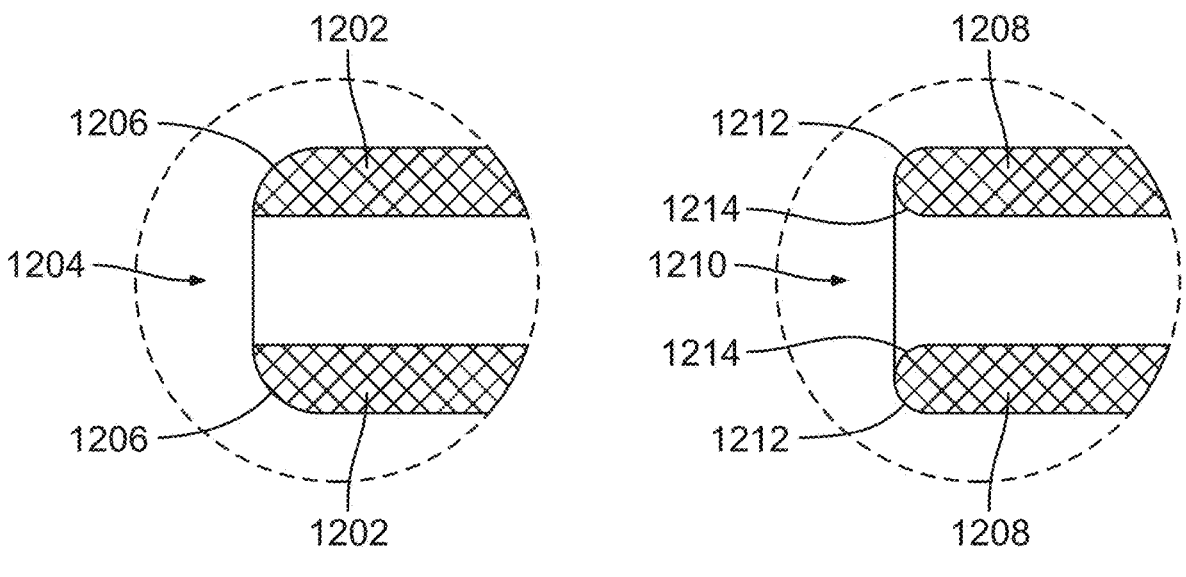
FIG. 12A
FIG. 12B
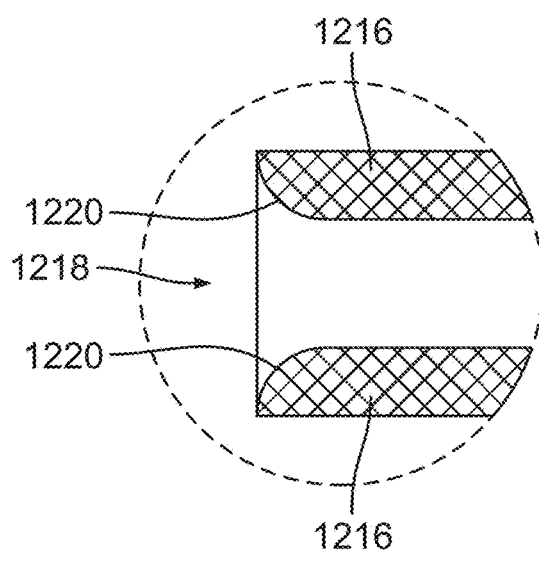
FIG. 12C

1300

1302    1306                    1304

1303

A

1308

1310        1306

1312

B

1314

1400

1603c

1604c

1604c

1604c

1606c

1608c

1606c

1608c

1606c (left)          (right)

1606d

1603d

1604d

1604d

1604d

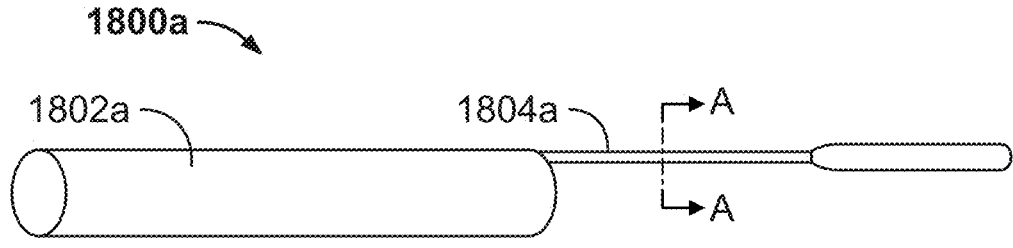
FIG. 18A
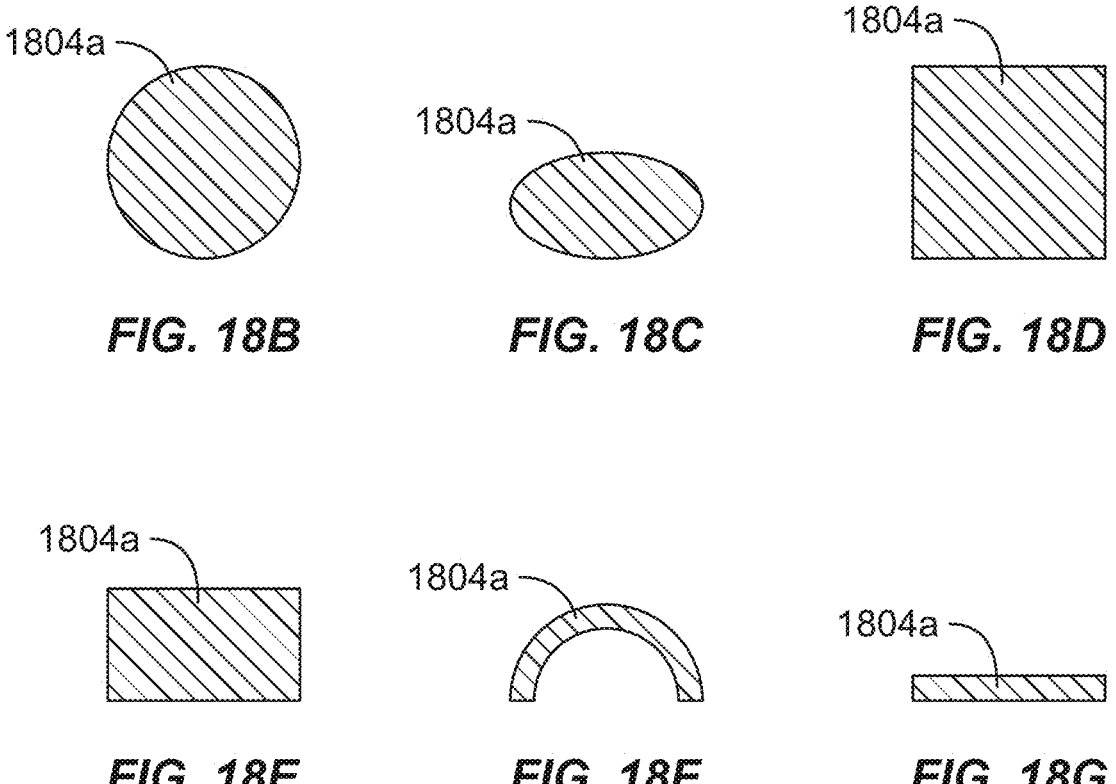
FIG. 18B        FIG. 18C        FIG. 18D
FIG. 18E        FIG. 18F        FIG. 18G

2200

2210

2208

2206

2204

2205

2202

2212

2218

2214

2206

2216

2204

2220

2202

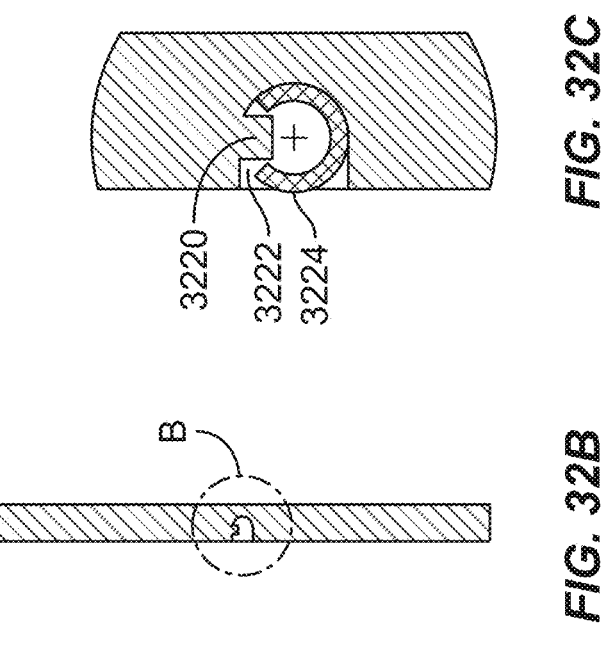
FIG. 32C
FIG. 32B
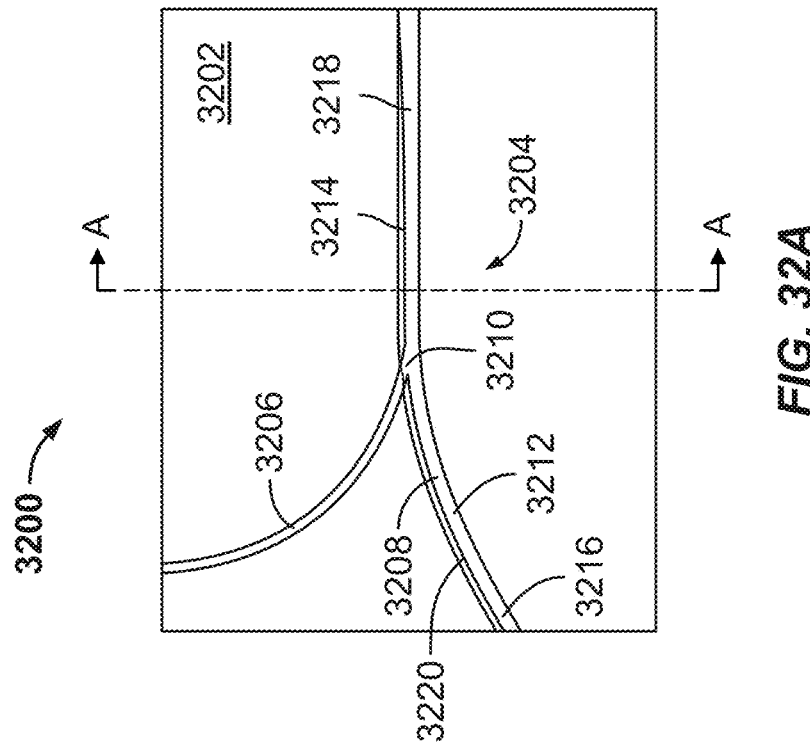
FIG. 32A

SUPPORT CATHETERS AND ASSOCIATED LOADING COMPONENTS

CLAIM OF PRIORITY

This non-provisional patent document claims the benefit of priority under 35 U.S.C. § 119(e) to Galdonik et al., U.S. Provisional Patent Application Ser. No. 63/149,510, entitled "EXPANDABLE SPLIT SUPPORT CATHETER AND LOADING TOOL DESIGNS, METHODS FOR MANU- FACTURE AND METHODS FOR USE" and filed on Feb. 15, 2021, which is herein incorporated by reference in its entirety.

TECHNICAL FIELD

This patent document relates to medical devices. More particularly, but not by way of limitation, the patent document relates to support catheters with attributes configured to support other interventional devices within a patient's vasculature. Accessory devices configured to assemble support catheters with various interventional devices are also disclosed.

BACKGROUND

A guide catheter can back out and withdraw from a vessel's ostium or branch when an interventional device, such as a guidewire, balloon catheter, stent or stent catheter, is passed therethrough and advanced beyond the guide catheter's distal end. This backing out of the guide catheter can cause the operating physician to lose the ability to further advance the interventional device distally. The inter- ventional device itself may also be unable to access or cross a treatment site, such as a lesion, due to lack of backup support. Devices configured to prevent guide catheter with- drawal and provide additional anchoring support for inter- ventional devices must be selected by an operating physician before a medical procedure is initiated to avoid the need to remove one or more devices from a patient's vasculature during the procedure.

Overview

The present inventors recognize that the need to provide increased backup support to interventional devices, such as guide catheters, during interventional procedures can be unpredictable. The present inventors also recognize that, once advanced down a blood vessel during an interventional procedure, support catheters can increase procedural success by "anchoring" an interventional device in the vessel, thereby making it less likely to back out or dislodge from a target site as another interventional device, e.g., balloon or stent delivery system, is advanced. The present inventors also recognize that support catheters can reduce friction between interventional devices and the surrounding vessel walls, making it less likely that the interventional devices catch on calcified and diseased upstream vessel wall tissue. The present inventors recognize that support catheters are increasingly used in chronic total occlusion (CTO) and percutaneous coronary intervention (PCI) procedures to increase guide support, and also to provide a target for retrograde wire re-entry. Another useful role for support catheters recognized by the present inventors is to facilitate selective delivery of contrast (e.g., to a desired branch vessel), thereby improving angiographic imaging, with a reduction in contrast volume.

The present inventors recognize that currently commer- cialized support catheters may consist of a proximal handle, a flexible distal tubular structure, and a push rod connecting the handle to the tube. The distal tubular structure can include a radiopaque element(s) so that it can be visualized, such as a round platinum-iridium (Pt—Ir) marker band. The distal tube is typically a fully round tube, and the wall may consist of an inner lubricious layer (such as a PTFE liner), a support material (such as stainless steel braid), and a polymeric outer layer (such as Nylon, Pebax®, or the like).

The present inventors further recognize that some preex- isting support catheters have an approximately 5F outer diameter configured to be advanced through a 6F guide catheter, where F is an abbreviation for the French catheter scale (a unit of measure catheter diameter (1F=⅓ mm)). Also on the market are 4F, 6F, and 7F support catheters. Generally, a 4F catheter has an internal diameter greater than or equal to 0.050 inches. Generally, a 5F catheter has an internal diameter greater than or equal to 0.059 inches, a 6F catheter has an internal diameter greater than or equal to 0.070 inches, and a 7F catheter has an internal diameter greater than or equal to 0.078 inches. It is to be appreciated that, because the wall thickness of the support catheter's tubular member can vary, and because of the need for some amount of space between the support catheter's tubular member and the guide catheter's inner wall, the support catheter's tubular member's inner diameter, when the tube does not have a device such as an interventional cardiology device inserted into it, may vary, and may be smaller than the inner diameter of a guide catheter of corresponding size. For example, while a standard 5F guide catheter may have an inner diameter of 0.059 inches or more, a 5F support catheter of the present invention in its resting state (without anything inserted into or through it) may have an inner diameter of about any of 0.052 inches or less, 0.053 inches, 0.054 inches, 0.055 inches, 0.056 inches, 0.057 inches, 0.058 inches, or 0.059 inches or more. If the support catheter's tubular member is in an expanded state, such as where an interventional cardiology device has been inserted into it, the diameter of the support catheter's tubular member may be expanded beyond that of the diameter of the support catheter's tubular member in its resting state. Certain stan- dard coronary balloons and stent delivery systems can be advanced and withdrawn through a 5F support catheter. The relatively larger catheter systems may be used during rota- tional atherectomy, bifurcation PCI procedures, and some CTO procedures (e.g., with balloon anchoring). The diam- eter of the support catheter can affect how easily it can be advanced down the coronary artery, especially given that support catheters are often needed for the challenging inter- ventional procedures requiring navigation through vessels having upstream tortuosity, disease and calcification.

The present inventors further recognize that to use cur- rently commercialized designs of support catheters, the user must typically first advance the distal tubular structure of the support catheter over a guidewire and into the guide catheter and/or blood vessel. The user must then advance the inter- ventional device (e.g., balloon, stent, etc.) over the guidewire, through the guide catheter, and through the support catheter to reach the target lesion. Thus, currently marketed designs do not allow the support catheter to be inserted after the interventional device, which means the user must either pre-select cases to use a support catheter or withdraw the interventional device completely when a sup- port catheter is required, so that the support catheter can be loaded first into the guide catheter.

Similarly, the present inventors recognize that, once the lesion has been treated, an interventional device must be completely removed in order to subsequently remove the support catheter, or both need to be removed together. The user cannot remove an existing support catheter after its use while leaving the interventional device in the vasculature.

One reason current support catheters cannot be loaded directly onto or removed from an interventional device is that these devices typically have a large proximal luer or hub that prevents loading a tubular support catheter onto the proximal end. Accordingly, interventional devices must be placed after the support catheter is inserted. Associated drawbacks to the overall procedure recognized by the present inventors include requiring the user to preselect (guess) when a support catheter is needed and load it first for difficult cases. This approach typically results in more expensive, longer procedures. If the support catheter is not preselected, the user must withdraw the carefully placed interventional device, load the support catheter, and then reload the interventional device. This also results in longer, more expensive operations. In addition, after treatment with an interventional device, the support catheter cannot be withdrawn separately, which can complicate interventional procedures.

Also, the present inventors recognize that current tubular support catheters often have a fixed inner and outer diameter and are not tapered and/or expandable. This means there will inherently be a size difference between the inner diameter of the guide catheter and the outer diameter of the support catheter, and between the inner diameter of the support catheter and the outer diameter of the interventional device. Too great of a size difference between these surfaces may result in less support because the push forces applied to the proximal end of the devices will not translate into 100% forward push. Instead, the typically flexible catheters may serpentine or even buckle if the radial gaps between the devices are too great. The primary reason a support catheter is used is to constrain interventional devices to ensure that the proximally applied push forces effectively drive the devices forward. This also means that current support catheters enter the vessel in their largest configuration to enable the interventional device to be able to pass because they are not expandable, thus rendering it more difficult to track the device down a tight vessel.

The present inventors also recognize that there is tension between using the smallest diameter support catheter possible, so that the interventional device is tightly constrained and so the support catheter can more easily track down a tight vessel, versus using the largest guide catheter possible, to improve interventional device support. It may be possible to have a support catheter even fit tightly on the guidewire to improve support and push of the wire, or as tightly as possible to the interventional device. Current support catheters having fixed diameters cannot effectively accommodate the different diameters of guide catheters, interventional devices, and guidewires, and do not have an ability to expand in diameter if larger devices are inserted through them.

The support catheters disclosed herein can be advantageously deployed "on-the-fly" after an interventional procedure has begun, i.e., without preselection by a user, to provide effective backup support to at least one interventional device already inserted within a blood vessel. A longitudinal slit defined into a distal tubular member of a disclosed support catheter enables a user to insert the support catheter after and over the interventional device by expanding the width of the slit in the support catheter's distal tubular member and inserting a portion of the interventional device into the distal tubular member. Likewise, the support catheter can be uncoupled from the interventional device by urging the interventional device out of the support catheter through the longitudinal slit in the support catheter's distal tubular member. Loading the support catheter onto the interventional device after determining that the device requires backup support provides procedural flexibility not available using preexisting devices, as does unloading the support catheter during a procedure. To facilitate the coupling (or mounting) process, accessory devices comprising loading tools are also disclosed herein, along with optional bundling tools particularly beneficial for certain interventional procedures.

Because the disclosed support catheters can be expandable, they may also be used for procedures that typically require catheters having larger diameters. The reduction in device profile can enhance the ease with which the catheter is advanced down the coronary artery (or other vessel). This may lessen the need for more aggressive approaches to advancing the support catheters distally, such as balloon anchoring in the distal vessel, which are associated with an increased risk of upstream vessel dissection. The disclosed support catheters may have a reduced diameter at the distal tip, only, or over the entire length of the elongate tubular member having the longitudinal slit.

Vessel anchoring provided by the disclosed support catheters may be improved relative to preexisting devices, largely because the support catheters can be inserted deep into a blood vessel. Stent delivery system protection and support may also be maintained using the disclosed support catheters, because the stent on its delivery balloon remains sheathed around almost a majority of its circumference.

Another advantage of embodiments of the expandable slit support catheters of the present disclosure is that the catheters can be "clipped" onto a guidewire and balloon/stent delivery catheter shaft in situ, close to the Tuohy-Borst hemostatic valve (mounted on the proximal end of the guide catheter), for example, and then advanced through the guide catheter and down the coronary artery, all without first having to remove the balloon/stent delivery catheter from the patient.

The present inventors further recognize that there may also be an advantage to more quickly and easily removing support catheters from a patient. The disclosed support catheters can be withdrawn and removed from a guidewire and interventional device shaft in a "peel-away" manner, which may involve withdrawing the tubular member of the support catheter from the guide catheter, and peeling the tubular member off the inserted wire/therapeutic device.

Support catheters of the present disclosure can include, in some embodiments, a longer distal segment (30-40 cm), relatively shorter shaft, and optionally an added distal curve to provide directional control within cardiac chambers and when crossing the tricuspid valve. These and related embodiments can allow pacing leads to be delivered to an optimal position in the right atrium and right ventricle, and for left ventricular pacing in coronary veins accessed via the coronary sinus. This version of the catheter can optionally have a distal curve, so that its distal end can be directionally controlled. The support catheter can be inserted through a short, straight vascular sheath, or through a longer sheath with a distal curve designed, for example, to engage the coronary sinus. Once the pacing lead is fixed into position, the peel-away feature allows easy removal, with minimal risk of lead displacement.

Various additional improvements to the design, implementation, construction and/or use of support catheters and the like are described in U.S. Pat. No. 10,173,029 entitled "Deflection Control Catheters, Support Catheters and Methods of Use," the entire teachings of which are incorporated herein by reference.

These and other examples and objects of the present support catheters, loading components, and related methods will be set forth in the following Detailed Description. This Overview is intended to provide non-limiting examples of the present subject matter; it is not intended to provide an exclusive or exhaustive explanation. The Detailed Description below is included to provide further information about the present support catheters, loading components, and related methods.

BRIEF DESCRIPTION OF THE DRAWINGS

In the drawings, like numerals can be used to describe similar features and components throughout the several views. The drawings illustrate generally, by way of example but not limitation, various embodiments discussed in the present patent document.

FIG. 12A illustrates an enlarged cross-sectional view of a distal end of a support catheter, as constructed in accordance with at least one embodiment.

FIG. 12B illustrates an enlarged cross-sectional view of a distal end of another support catheter, as constructed in accordance with at least one embodiment.

FIG. 12C illustrates an enlarged cross-sectional view of a distal end of another support catheter, as constructed in accordance with at least one embodiment.

FIG. 18A illustrates a perspective view of a support catheter, as constructed in accordance with at least one embodiment.

FIG. 18B illustrates an enlarged cross-sectional view of a push member that can be included in the support catheter of FIG. 18A, taken along line A-A.

FIG. 18C illustrates an enlarged cross-sectional view of a push member that can be included in the support catheter of FIG. 18A, taken along line A-A.

FIG. 18D illustrates an enlarged cross-sectional view of a push member that can be included in the support catheter of FIG. 18A, taken along line A-A.

FIG. 18E illustrates an enlarged cross-sectional view of a push member that can be included in the support catheter of FIG. 18A, taken along line A-A.

FIG. 18F illustrates an enlarged cross-sectional view of a push member that can be included in the support catheter of FIG. 18A, taken along line A-A.

FIG. 18G illustrates an enlarged cross-sectional view of a push member that can be included in the support catheter of FIG. 18A, taken along line A-A.

FIG. 32A illustrates a plan view of a loading tool configured to facilitate coupling of a support catheter with an interventional device, as constructed in accordance with at least one embodiment.

FIG. 32B illustrates a cross-sectional view of the loading tool shown in FIG. 32A, taken along line A-A.

FIG. 32C illustrates an enlarged cross-sectional view of the loading tool shown in FIG. 32B, taken at Detail B.

FIG. 42 illustrates a loading tool comprising a ring-like feature for user handling, as constructed in accordance with at least one embodiment.

FIG. 43 illustrates a bundling tool coupled with a guidewire and interventional device, as constructed in accordance with at least one embodiment.

FIG. 44 illustrates another bundling tool, as constructed in accordance with at least one embodiment.

FIG. 45 illustrates another bundling tool, as constructed in accordance with at least one embodiment.

FIG. 46 illustrates a loading tool comprising an integral bundling feature coupled with a guidewire and interventional device, as constructed in accordance with at least one embodiment.

FIG. 47 illustrates a loading tool comprising a rod and bundling tube, as constructed in accordance with at least one embodiment.

FIG. 48 illustrates a loading tool comprising a single tube, as constructed in accordance with at least one embodiment.

FIG. 49 illustrates a loading tool comprising countersunk channels, as constructed in accordance with at least one embodiment.

FIG. 50A illustrates a schematic view of a method of inserting a pacemaker lead within a vascular target site in accordance with the disclosed embodiments.

FIG. 50B illustrates a schematic view of a subsequent step of the method shown in FIG. 50A.

FIG. 50C illustrates a schematic view of a subsequent step of the method shown in FIG. 50B.

FIG. 50D illustrates a schematic view of a subsequent step of the method shown in FIG. 50C.

Figure 50A:
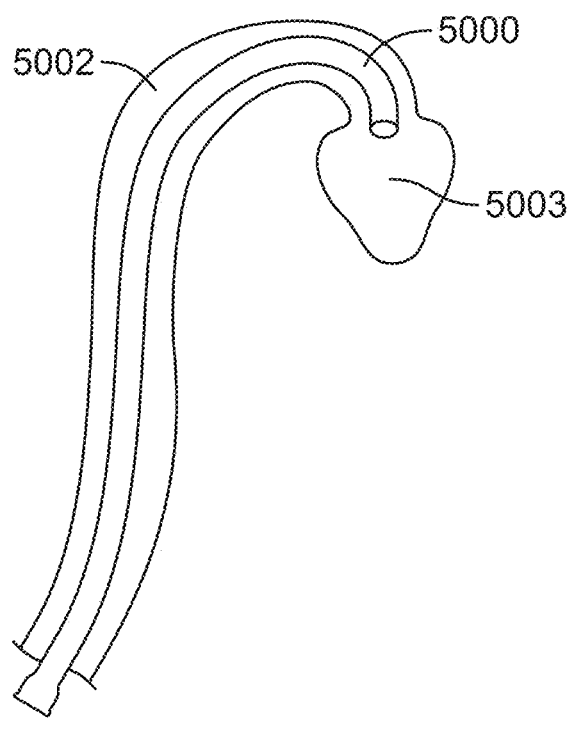
Figure 50B:
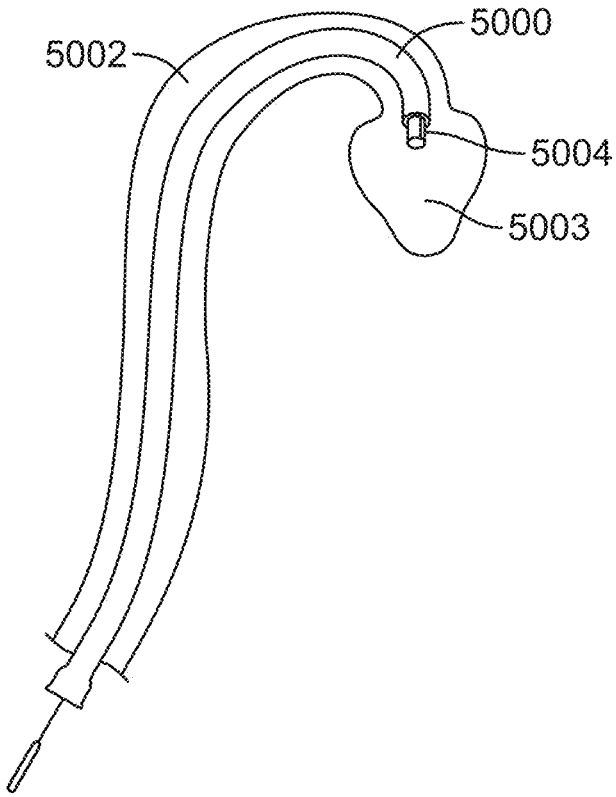
Figure 50C:
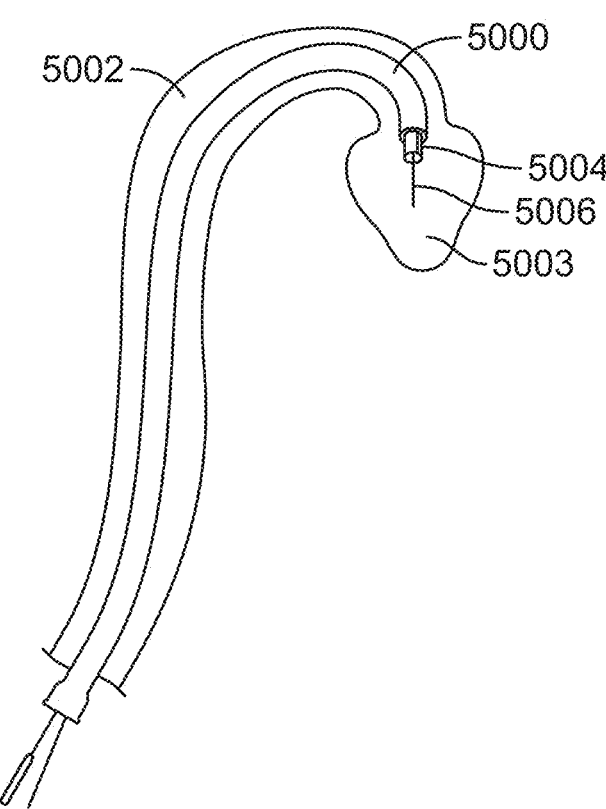
Figure 50D:
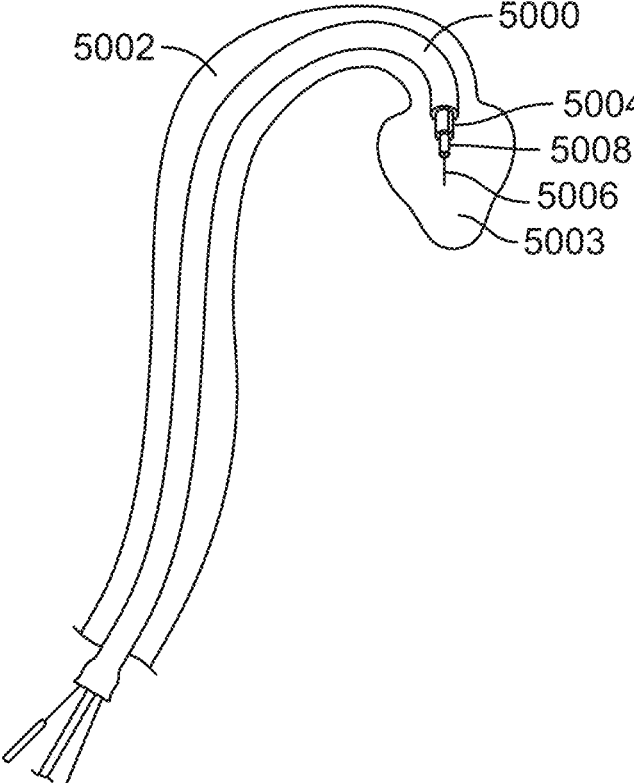
Figure 50E:
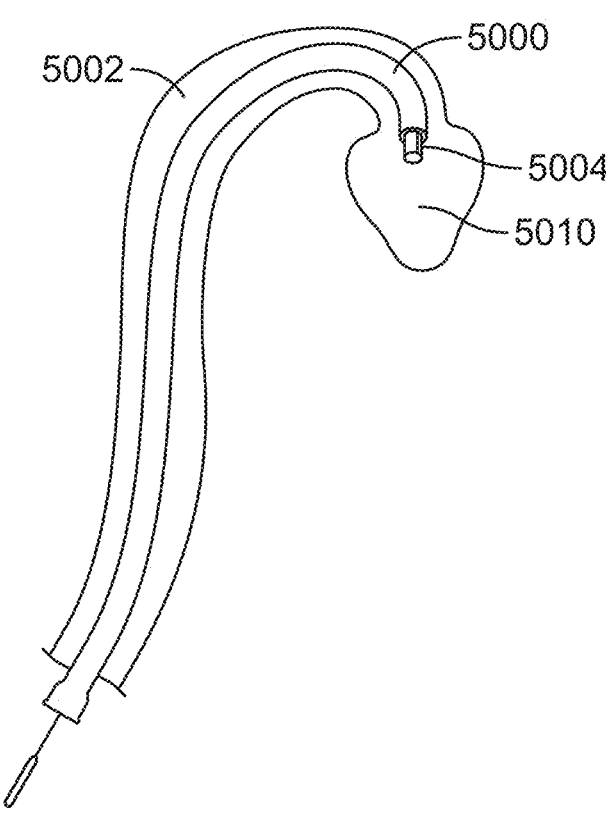

FIG. 50E illustrates a schematic view of a subsequent step of the method shown in FIG. 50E.

Figure 50F:
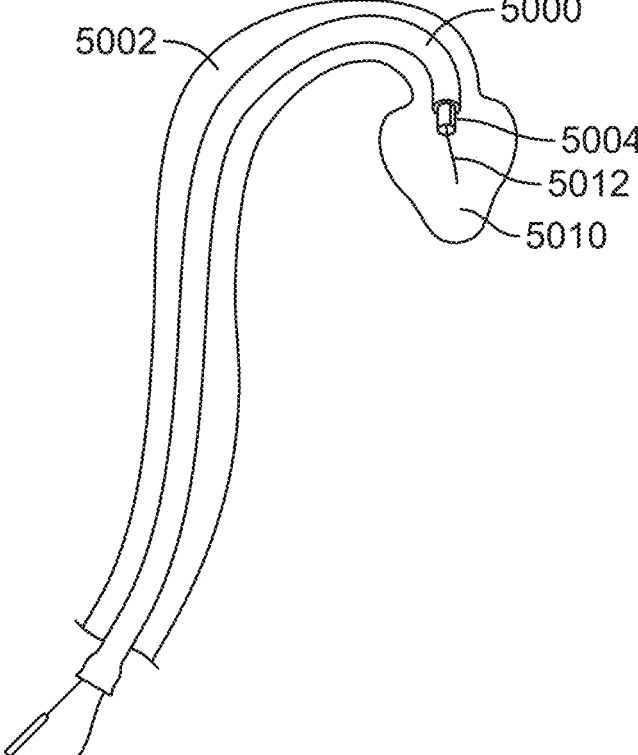

FIG. 50F illustrates a schematic view of a subsequent step of the method shown in FIG. 50E.

Figure 50G:
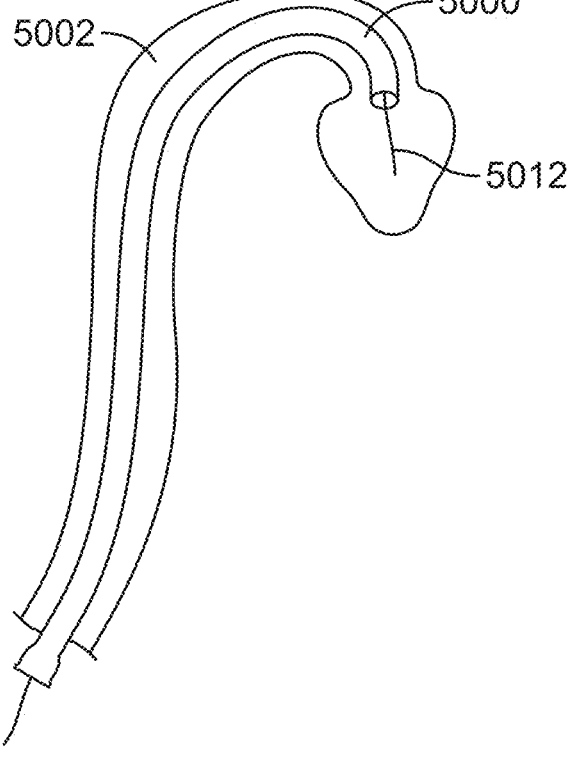

FIG. 50G illustrates a schematic view of a subsequent step of the method shown in FIG. 50F.

Figure 51A:
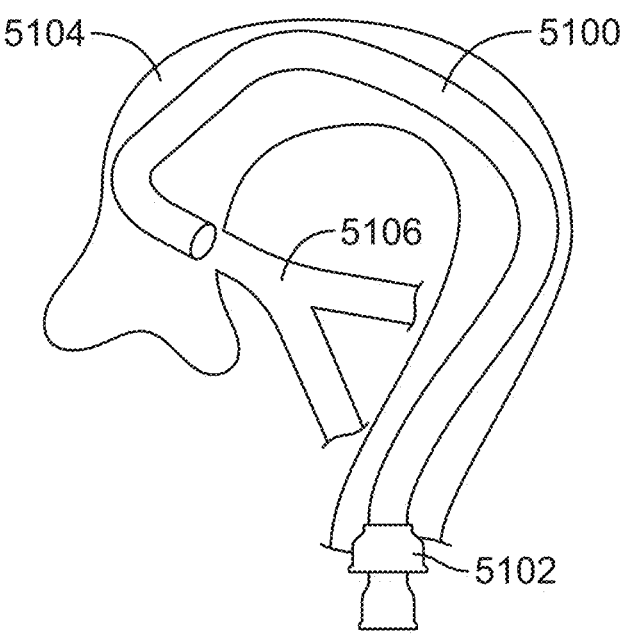

FIG. 51A illustrates a schematic view of a method of treating a bifurcation lesion in accordance with the disclosed embodiments.

Figure 51B:
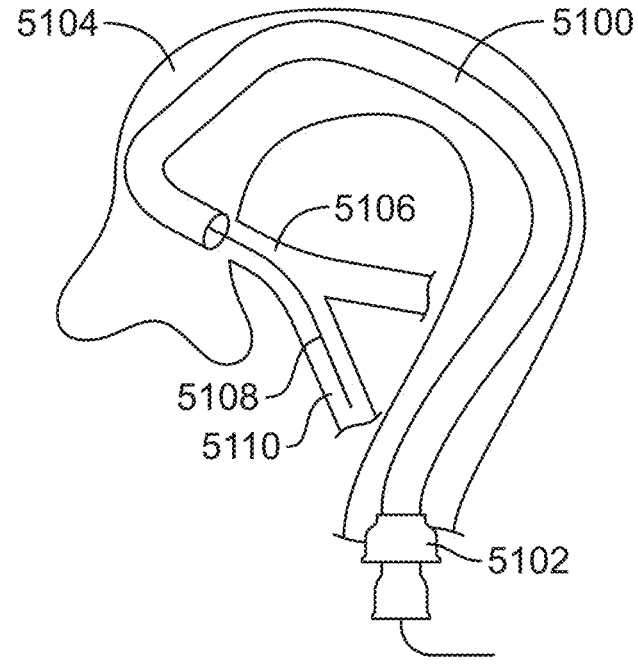

FIG. 51B illustrates a schematic view of a subsequent step of the method shown in FIG. 51A.

Figure 51C:
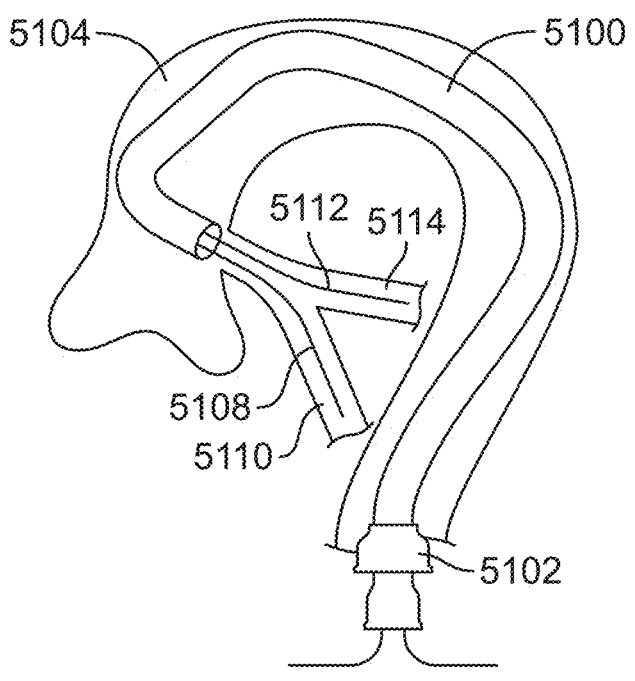

FIG. 51C illustrates a schematic view of a subsequent step of the method shown in FIG. 51B.

Figure 51D:
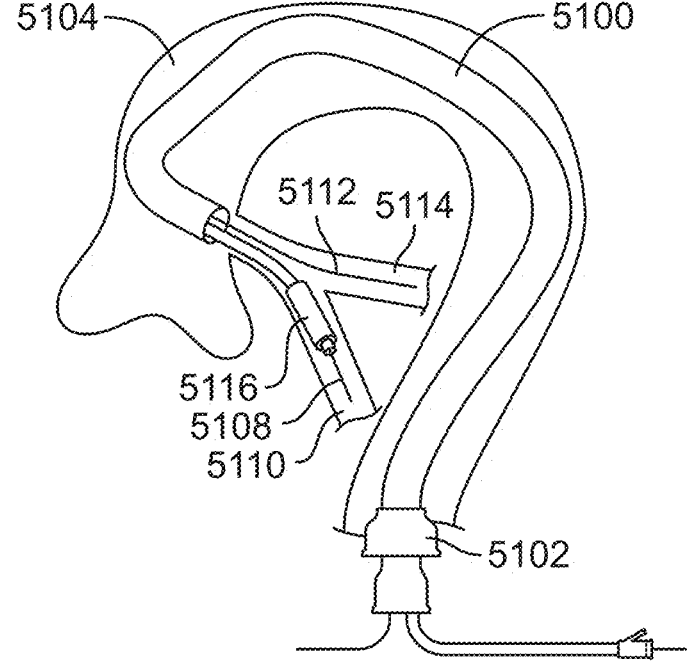

FIG. 51D illustrates a schematic view of a subsequent step of the method shown in FIG. 51C.

Figure 51E:
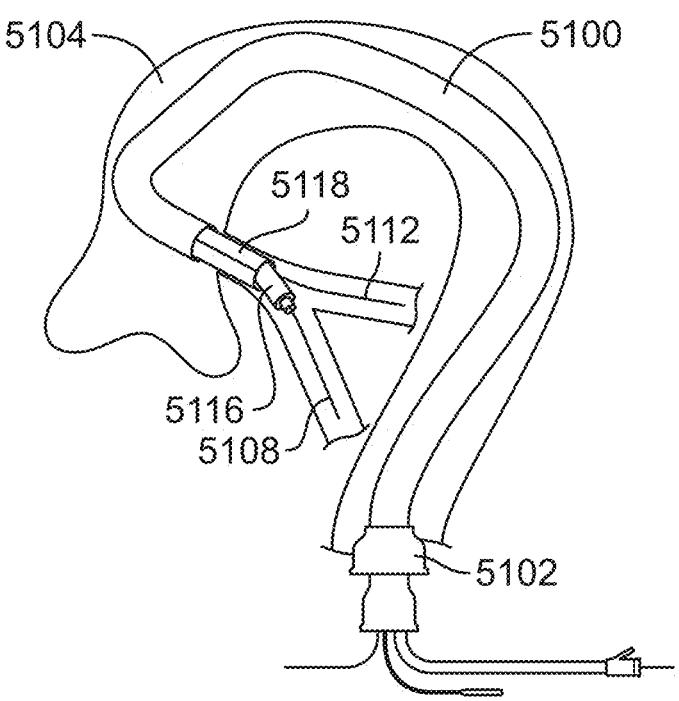

FIG. 51E illustrates a schematic view of a subsequent step of the method shown in FIG. 51D.

Figure 51F:
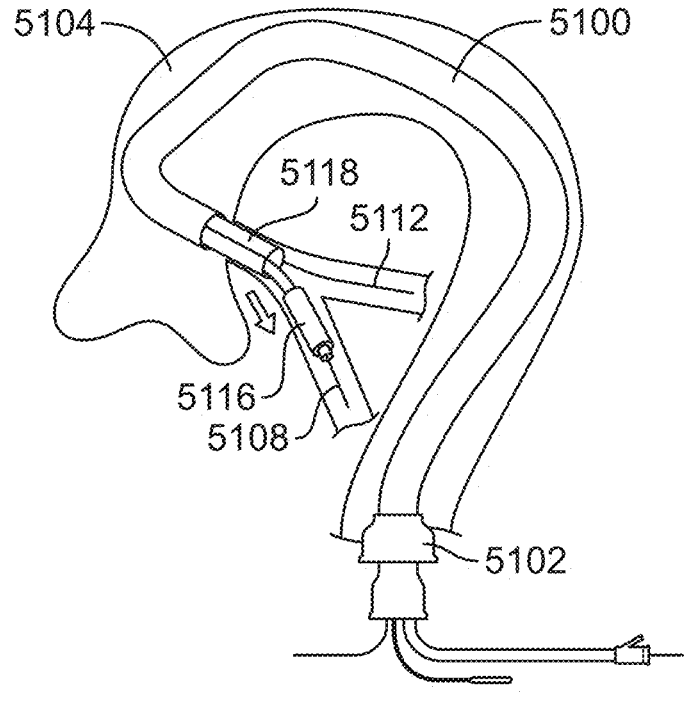

FIG. 51F illustrates a schematic of the support catheter inserted through the guide catheter and introducer sheath.

Figure 51G:
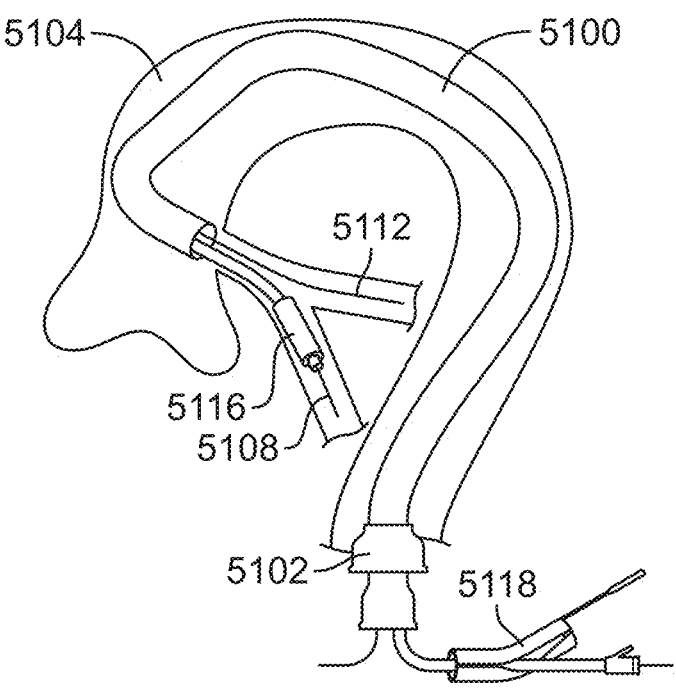

FIG. 51G illustrates a schematic view of a subsequent step of the method shown in FIG. 51F.

Figure 51H:
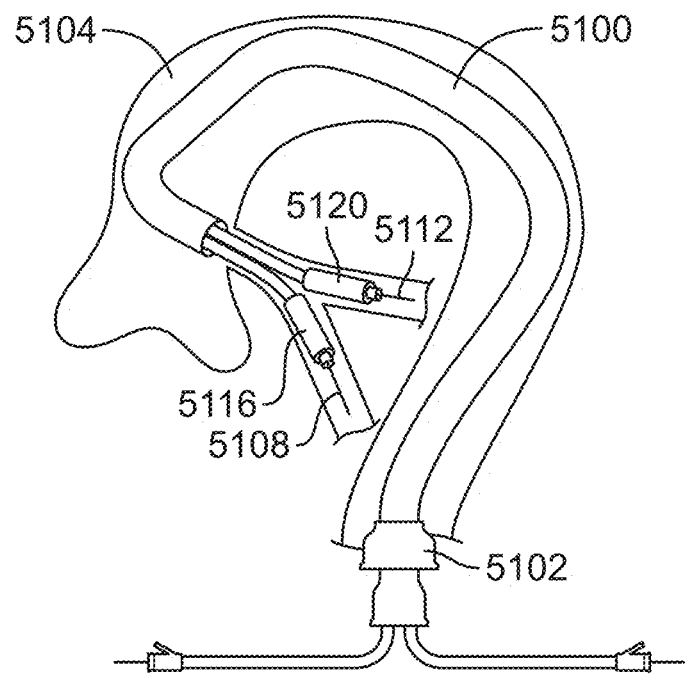

FIG. 51H illustrates a schematic view of a subsequent step of the method shown in FIG. 51G.

Figure 51I:
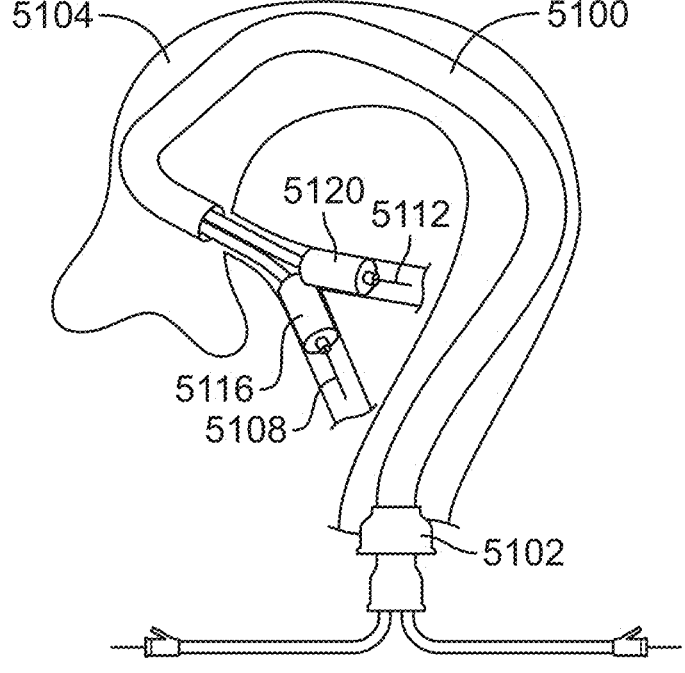

FIG. 51I illustrates a schematic view of a subsequent step of the method shown in FIG. 51H.

Figure 52A:
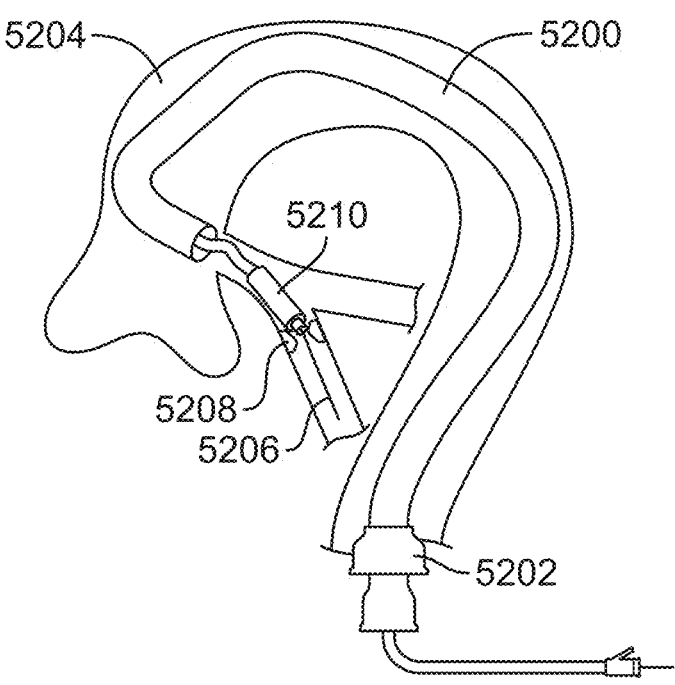

FIG. 52A illustrates a schematic view of a method of inflating a treatment balloon in accordance with the disclosed embodiments.

Figure 52B:
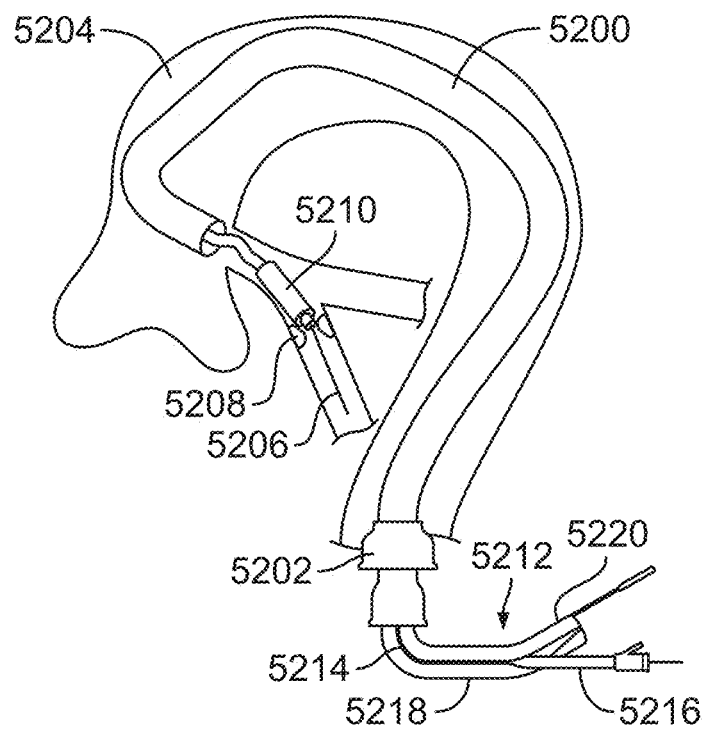

FIG. 52B illustrates a schematic view of a subsequent step of the method shown in FIG. 52A.

Figure 52C:
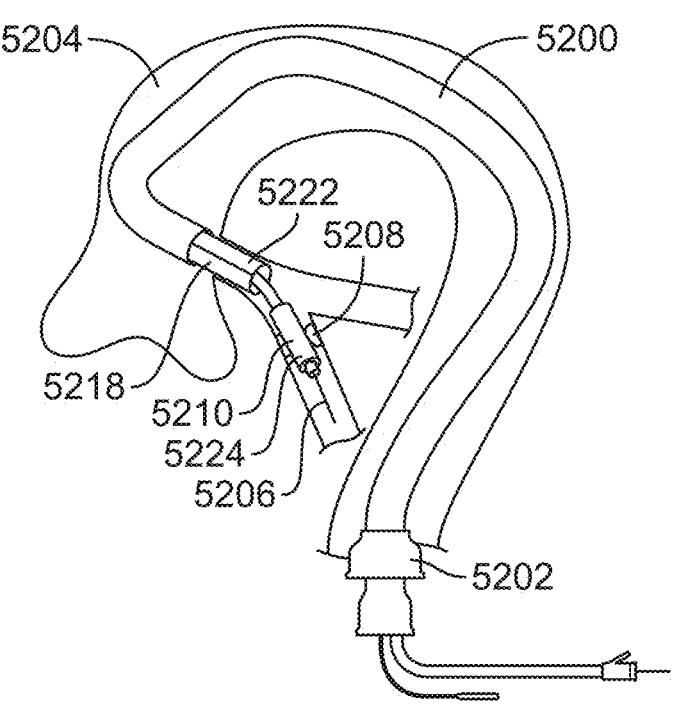

FIG. 52C illustrates a schematic view of a subsequent step of the method shown in FIG. 52B.

Figure 52D:
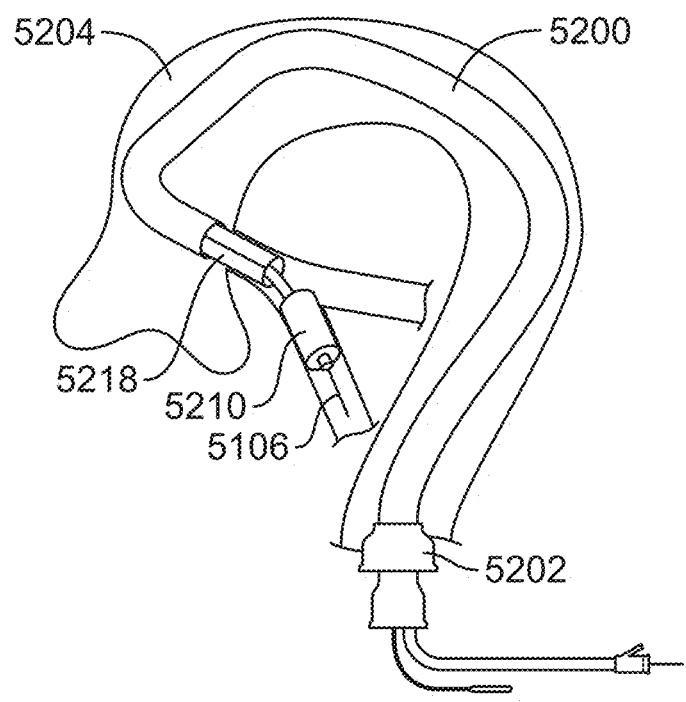

FIG. 52D illustrates a schematic view of a subsequent step of the method shown in FIG. 52C.

Figure 52E:
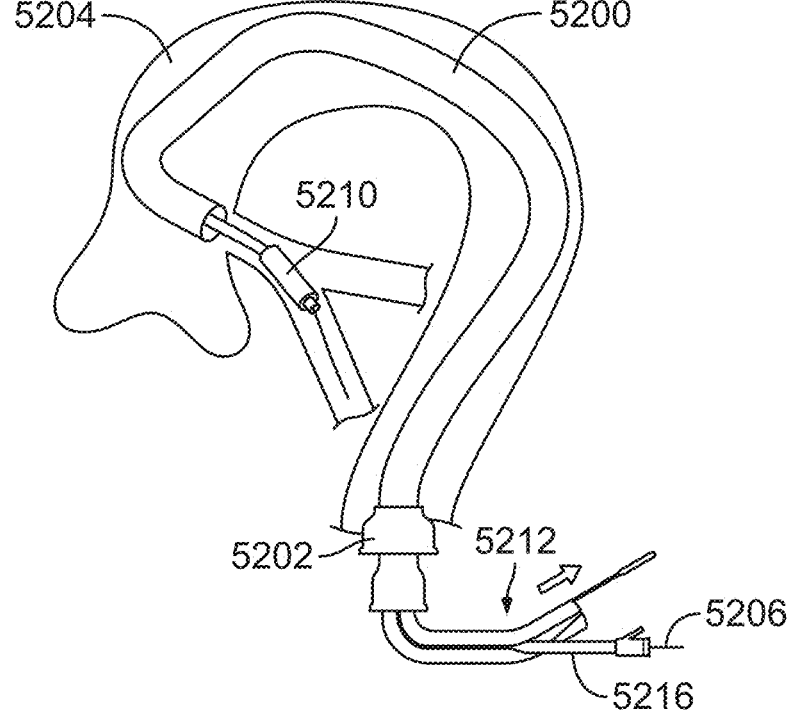

FIG. 52E illustrates a schematic view of a subsequent step of the method shown in FIG. 52D.

Figure 53A:
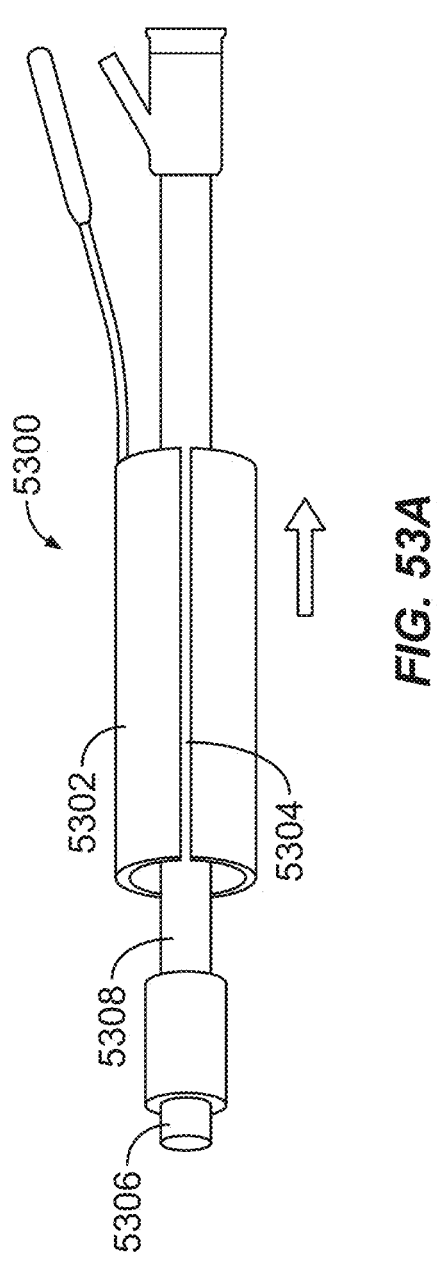

FIG. 53A illustrates a schematic of a support catheter being back-loaded over an interventional device.

Figure 53B:
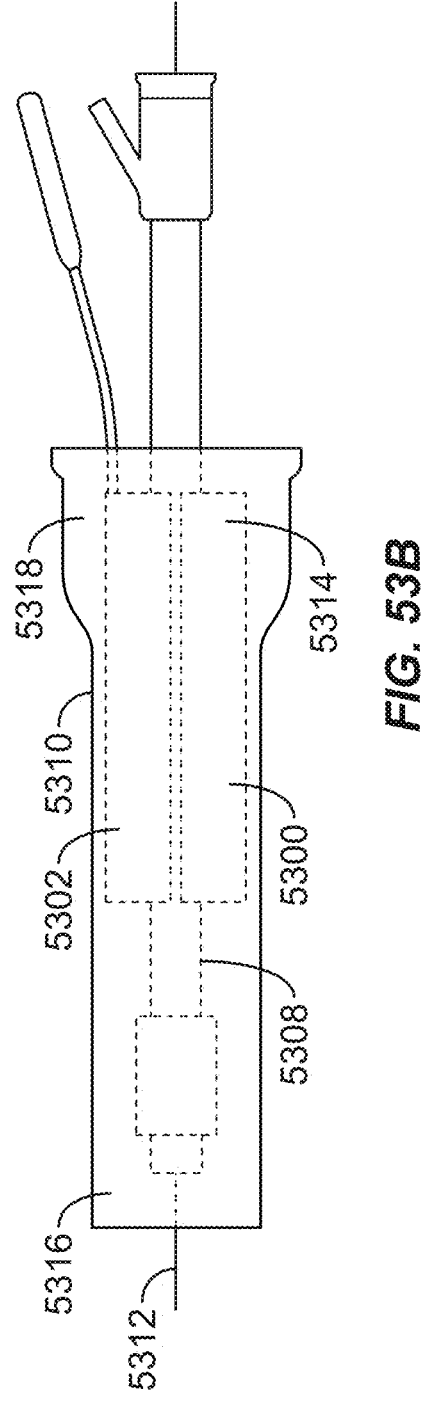

FIG. 53B illustrates a schematic of a support catheter and interventional device within a guide catheter.

The drawing figures are not necessarily to scale. Certain features and components may be shown exaggerated in scale or in schematic form, and some details may not in the interest of clarity and conciseness.

DETAILED DESCRIPTION

Various embodiments and aspects of the present disclosure will be described with reference to details discussed below, and the accompanying drawings will illustrate the various embodiments. The following description and drawings are generally illustrative of the present disclosure and are not to be construed as limiting. Numerous specific details are described to provide a thorough understanding of various embodiments of the present disclosure. However, in certain instances, well-known or conventional details are not described in order to provide a concise discussion of embodiments of the present disclosure.

This patent document discloses, among other things, support catheters to be placed within guide catheters for providing support and guidance in a vessel when percutaneously advancing interventional devices, such as guidewires, balloon catheters, stents, or stent catheters. The support catheters can be inserted into the vessel after determining that one or more already-inserted interventional devices require or could benefit from additional support. Accessory devices for loading the support catheters over in-place interventional devices are also disclosed. The present support catheter has application in the coronary, peripheral, and other vasculature.

The support catheters disclosed herein can comprise guide extension catheters configured to be passed through a main lumen of a guide catheter so that its distal end portion can be extended beyond a distal end of a guide catheter, for example as described in U.S. Pat. No. 8,048,032 (and child cases) and U.S. Pat. No. 10,751,514, which are incorporated by reference in their entireties herein.

As used herein, an "interventional device" is any device inserted into the vasculature of a patient to treat a medical condition. Interventional devices can provide therapy and/or procedural support. For example, an interventional device may be used to treat a medical issue, e.g., a blood vessel occlusion or stenotic lesion, and/or an interventional device may be used to guide another interventional device to a treatment site, where the interventional device may secure or position the other device. For these purposes, interventional devices are typically elongate devices having diameters small enough to fit within a patient's blood vessels. Interventional devices deployed to treat a blood vessel lesion, for example, may comprise a treatment catheter carrying a treatment structure, such as an inflatable balloon, stent, and/or distal threaded portion configured to drill through the lesion. Interventional devices can include interventional cardiology devices in some embodiments. Additional non-limiting, non-exhaustive examples of interventional devices contemplated herein include: stents, stent delivery devices, balloon catheters, balloon delivery devices, and/or pacemaker leads. Solely for consistency and ease of illustration, "interventional device" and "support catheter" refer to separate devices herein.

As used herein, a "user" can be defined as a person guiding the disclosed support catheters and interventional devices into and from a patient's vasculature during a medical procedure. Non-limiting examples of users contemplated herein include medical professionals, such as treating clinicians, nurses, physicians, interventional cardiologists, and/or physician assistants.

A "blood vessel" can be defined herein as any vessel within a patient's vasculature, non-limiting examples of which may include various arteries and veins, including the branches and ostia included therein. Specific examples can include coronary arteries, but it should be understood that the support catheters can also be used for treating non-coronary diseased vessels, peripheral vasculature, neuro vasculature, or other hollow structures (e.g., biliary tract, ureter, etc.) throughout a patient's body where interventional devices are or can be deployed.

The support catheters described herein (which may also be referred to herein as "expandable slit support catheters," "slit support catheters," or "guide extension catheters") assist in directing and securing elongate interventional devices within a patient's blood vessels during a variety of medical procedures, such as percutaneous procedures targeting difficult-to-reach branch vessels. A medical device delivery system can include at least one interventional device and a support catheter configured to couple with and ride over the interventional device(s) in an over-the-wire or rapid-exchange configuration. Once coupled with an interventional device, the support catheter can aid in resisting axial and shearing forces that tend to dislodge interventional devices from a seated position, which may include the ostium of a branch artery.

One embodiment of an expandable support catheter 100 in accordance with principles of the present disclosure is shown in FIGS. 1A-1F. Among other features, the support catheter includes an expandable, longitudinal slit running a full length of a distal tubular member thereof. The slit can accommodate the insertion and removal of various interventional devices into the tubular member such that the support catheter can be coupled with the interventional devices inside a blood vessel after the interventional devices have already been inserted therein. When the support catheter is no longer needed, it can be simply withdrawn from a treatment site and uncoupled from the interventional device(s). The configuration of the slit can vary to accommodate the needs of a user, as can the configuration of the tubular member defining the slit, as further described herein. While the distal tubular portion is referred to as a "member" throughout this document, it is understood that "member" refers to a longitudinal segment or portion, as appropriate in the context, and is not limited to a separate structure; instead, a person of ordinary skill reading this disclosure would understand that the portions of the claimed support catheter can be monolithic, unitary, made up of one, two, or more components or materials, or combinations of these (longitudinally and/or axially oriented), and that unless otherwise stated the term "member" is not intended to limit how the device is constructed.

Figures 1A, 1B, 1C:
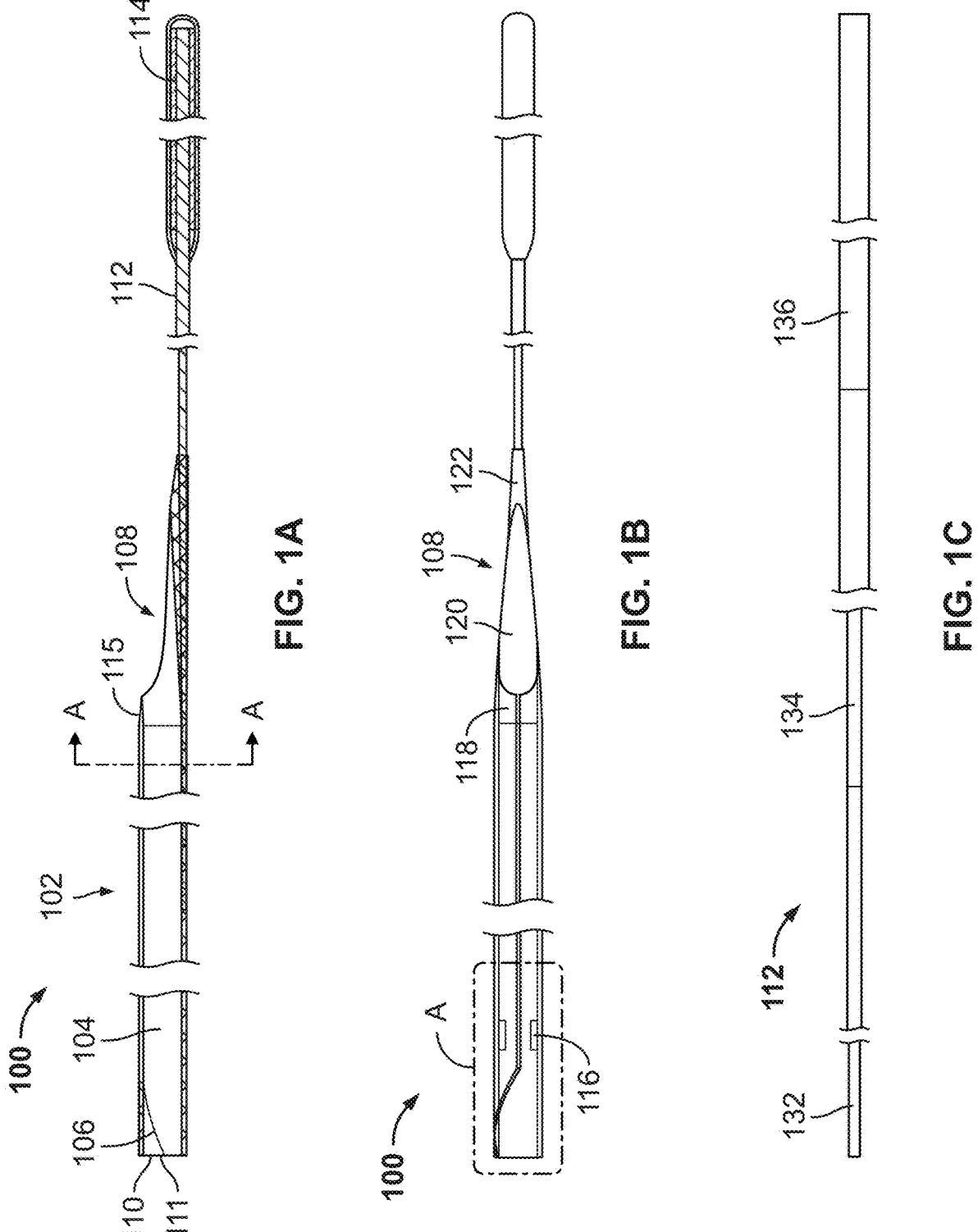
FIG. 1A illustrates a fragmentary cross-sectional side view of a support catheter, as constructed in accordance with at least one embodiment.
FIG. 1B illustrates a plan view of the support catheter shown in FIG. 1A.
FIG. 1C illustrates a fragmentary side view of the push member included in the support catheter shown in FIG. 1A.

The support catheter 100 depicted in the longitudinal cross-section of FIG. 1A includes a rapid exchange device 102 comprised of a distal sheath or tubular member 104 defining a longitudinal slit 106 and an angled proximal port 108 opposite a distal end opening 110. An inner lumen 111 defined by the tubular member 104 connects the proximal port 108 to the distal end opening 110. The support catheter 100 further includes a push member 112, e.g., connecting wire or rod, which can be eccentrically coupled to the tubular member 104 at one end and an optional handle member 114 at the opposite, proximal end accessible to a user outside the patient's body. The push member 112 can transmit pushing and pulling forces applied by a user to slidably advance or retract the support catheter 100 during a medical procedure without blocking the guide catheter's lumen, so that interventional devices can be advanced alongside the push member 112 and then advanced into the tubular member 104 via the proximal port 108. The longitudinal slit 106 can accommodate the loading and unloading of the support catheter 100 onto and from various interventional devices during a medical procedure, respectively. Such accommodation may be achieved via expansion of the width of the slit 106 caused by urging an interventional device therethrough, with or without the use of a loading tool, as further set forth and described below.

The handle member 114 can be formed from any material(s) that can be gripped by a user, such as a polycarbonate material. Together with the push member 112, the handle member 114 can allow the user to push the tubular member 104 through a patient's vasculature (or body) to a region of interest. The handle member 114 can also be sized or shaped such that it is inhibited from passing through a hemostatic valve attachable to a proximal end of a guide catheter through which portions of the support catheter are inserted.

The length of the support catheter 100 can vary. In some embodiments, such as the one depicted in FIG. 1A, the support catheter has a length of about 150 cm. In additional embodiments, the length of the support catheter 100 may be less than about 50 cm, or about any of 50 cm, 60 cm, 70 cm, 80 cm, 90 cm, 100 cm, 110 cm, 120 cm, 130 cm, 140 cm, 150 cm, 160 cm, 170 cm, 180 cm, 190 cm, 200 cm or more, or any length therebetween. The length of the support catheter 100 can be such that the tubular member 104 can reach a distal end or distal portion of an interventional device positioned at a vascular target site. Accordingly, the support catheter 100 may have a length approximately equal to or slightly less than the length of an interventional device. When adapted for use with a guide catheter or sheath, the support catheter 100 may have a length that is longer than that of the guide catheter or sheath.

The length of the tubular member 104 can also vary. In the example shown, the tubular member 104 is about 17 cm long. Additional examples can feature a tubular member 104 having a length of about any of 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, or longer, or any length therebetween. When adapted for use with a guide catheter or sheath, the tubular member 104 may have a length that is shorter than that of the guide catheter or sheath.

The proximal port 108 defines the proximal opening of the lumen 111. In the illustrated embodiment, the proximal port 108 comprises an angled opening or cutout portion defined by a slanted wall, collar, or concave track extending from the push member 112 to a fully cylindrical portion that marks the proximal end 115 of the tubular member 104. The proximal port 108 may be considered a portion or extension of the push member 112 and/or tubular member 104 in some embodiments, especially if the port 108 is angled, stepped, or otherwise sloped. In some examples, the proximal port 108 may be considered a discrete component of the support catheter 100 bonded between or integrated with the proximal end 115 of the tubular member 104 or the distal end of the push member 112. Metallic or polymeric structures forming proximal port 108 can become less stiff and more flexible in a proximal-to-distal direction to provide a gradual flexibility transition between the more rigid push member 112 and the typically more flexible tubular member 104.

The shape, angle, and configuration of the port 108 may vary. For example, the proximal port 108 may define a smooth increase in circumference (in the distal direction) or a stepped increase in circumference defined by one or more plateaus. FIG. 1A, for example, shows a proximal port 108 that has a generally non-inclined region separated by two inclined regions. In some examples, the proximal port 108 can include, in the distal-to-proximal direction, a full circumference portion (which may constitute the proximal end of the tubular member 104), a hemicylindrical portion, and an arcuate portion, each of any desired length, similar to the tubular portion of the guide extension catheter described in U.S. Pat. No. 8,048,032. In still other embodiments, the proximal port 108 may not be angled, and may instead define a blunt, transverse opening perpendicular to the longitudinal axis of the tubular member 104. The proximal port 108 may have one slope or more, or no slope (i.e., generally perpendicular), and of any angle or angles, as desired.

As shown in the plan view of FIG. 1B, the support catheter 100 can also include at least one radiopaque marker band 116 within the tubular member 104 to enable visualization and tracking of the catheter within a patient's vasculature. In some embodiments, the support catheter 100 or a portion thereof, e.g., the distal tubular member 104, can be formed from radiopaque material. A radiopaque marker or a depth marker can also be included on the push member 112.

FIG. 1B also provides a plan view of the proximal port 108, showing a full circumference portion 118, a greater than 180° portion 120, and a less than 180° portion 122. Greater than 180° portion 120 may, for example, include structure forming approximately 300° of the circumference of the tubular member 104. Less than 180° portion 122 may, for example, include structure forming approximately 90° of the circumference of the tubular member 104.

A fragmented side view of the push member 112 is shown in FIG. 1C. In certain embodiments, the push member 112 can include a plurality of segments or portions having different stiffness and flexibility profiles to provide the support catheter 100 with a desired combination of pushing force and vessel placement capabilities. In this particular embodiment, the push member 112 tapers in the distal direction, such that the distal portion 132 has a narrower diameter than a middle portion 134, which has a narrower diameter than a proximal portion 136. Alternatively, the push member 112 can be of generally uniform thickness and/or cross-sectional shape along its length. Alternatively, the distal portion of push member 112, toward or adjacent to the tubular member 104, can be tapered, narrowed, and/or of a cross-sectional shape that differs from the cross-sectional shape of a portion or portions of the push member 112 that is or are proximal to the region toward or adjacent tubular member 104.

To effectively push the tubular member 104 of the support catheter 100 through a patient's vasculature while also preventing vessel blockage and allowing passage of various interventional devices alongside the push member 112, the push member 112 can comprise a flexible rod, wire, or tubular element having a relatively small cross-sectional diameter or other dimension(s). Examples can include a push member 112 comprised of at least one segment comprised only of wire, and/or wire and another segment comprised of hypotube, with an optional hypotube cover. Embodiments can also include at least one segment comprised of hypotube crimped with a wire segment. For example, the push member 112 can comprise a proximal portion formed of hypotube-crimped wire adjacent to a wire-only segment extending to and optionally beyond the proximal end 115 of the tubular member 104. Solid steel or Nitinol core wires and solid core wire wrapped in a smaller wire coil or braid can also be used. Alternatively, the push member 112 can have a void or voids along some or all of its length, either discrete, discontinuous, or continuous, in whole or in part. Generally, the push member 112 can include an elongate solid wire or rod of constant or varying dimensions and can comprise a polymeric or metallic material, such as high-tensile stainless steel (e.g., 304V, 304L or 316LV), mild steel, nickel-titanium alloys, nickel-chromium-molybdenum allows, nickel-copper allows, nickel-tungsten alloys or tungsten alloys. The push member 112 can be coated with a hydrophilic, silicone or other friction-reducing material. The push member 112 also can be made of a hypotube; where the interior of such a hypotube is open at both ends and along its length, such an interior would be too small to allow passage of a balloon or stent catheter.

In the example illustrated in FIG. 1C, the distal portion 132 of the push member 112 has a cross-sectional diameter of about 0.006 inches, the middle portion 134 has a cross-sectional diameter of about 0.008 inches, and the proximal portion 136 has a cross-sectional diameter of about 0.018 inches. The aforementioned cross-sectional diameters are not limiting, as cross-sectional diameters along the push member 112 can range from about less than about 0.001 inches to about 0.03 inches or greater. Any suitable diameter or diameters that do not interfere with the function or operation of the support catheter 100 may be used.

The length of the push member 112 may vary depending in part on the length and configuration of the support catheter 100, as the push member 112 can be attached at least to the proximal end of the tubular member and can extend proximally from this attachment to the optional handle member 114. Push members can be at least partially embedded within or coupled to at least a portion of the tubular member 104. The example shown in FIG. 1C has a length of about 146 cm, such that the push member 112 spans almost the entire length of the support catheter 100. In additional examples, the push member 112 may extend only to, or near, the proximal end 115 of the tubular member 104. In various embodiments, the length of the push member 112 may be less than about 50 cm, or about any of 50 cm, 60 cm, 70 cm, 80 cm, about 90 cm, 100 cm, 110 cm, 120 cm, 130 cm, 140 cm, 150 cm, 160 cm, 170 cm, 180 cm, 190 cm, 200 cm or more, or any length therebetween. In specific, non-limiting embodiments, for example for deployment in coronary arteries, the push member 112 can have a length of approximately 95 cm, and the tubular member 104 can have a length of approximately 15 cm. According to such embodiments, the inner diameter of the tubular member 104 can fit over a 4F to 4.5F catheter and an outer diameter to fit within a 6F guide catheter, with an adequate gap between the outer diameter of the tubular member 104 and the inner diameter of the guide catheter, as discussed below.

Figure 1D:
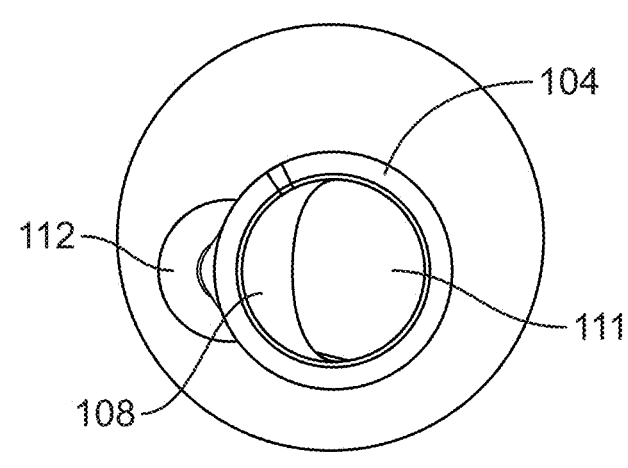
FIG. 1D illustrates an enlarged cross-sectional view of the support catheter taken along line A-A of FIG. 1A.

FIG. 1D is a cross-sectional side view of the support catheter 100 taken along line A-A of FIG. 1A, showing the push member 112, the angled proximal port 108, and the distal tubular member 104. The distal tubular member 104 can have a substantially circular cross-section defining the lumen 111 sized to accommodate passage of various interventional devices.

Figure 1E:
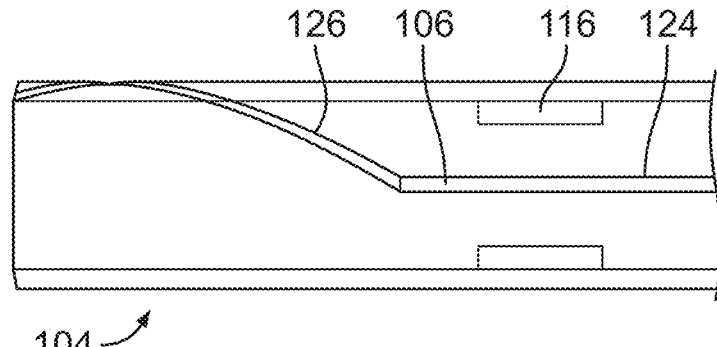
FIG. 1E illustrates an enlarged side view of a distal portion of the tubular member of the support catheter taken at Detail A of FIG. 1B.

FIG. 1E is a close-up view of a distal portion of the distal tubular member 104, taken at Detail A of FIG. 1A, showing the marker band 116 and a distal portion of the longitudinal slit 106. As shown, the slit 106 can include a straight portion 124 and at least one slanted or curved portion 126 distal to the straight portion (relative to the longitudinal axis of the tubular member 104). In embodiments, the support catheter 100 may have a continuous straight slit or a slit that jogs radially in one or more locations. In some embodiments, the slit may jog near its distal end, for example spanning the distal 0.25 cm to 3 cm of the tubular member 104. This configuration of the slit 106 can facilitate navigation of the support catheter 100 through tight bends in the vasculature by preventing the slit from opening before necessary. Although a slit 106 that jogs is shown, a variety of other non-straight slit configurations can be used to serve a similar purpose. In yet additional embodiments, for instance, the tubular member 104 can have a spiral-shaped, zig-zag, serpentine, or other irregular configuration, or a zipper-like longitudinal slit, to provide for easy mounting onto an interventional device while also providing increased resistance to accidental disengagement of the device.

Figure 1F:
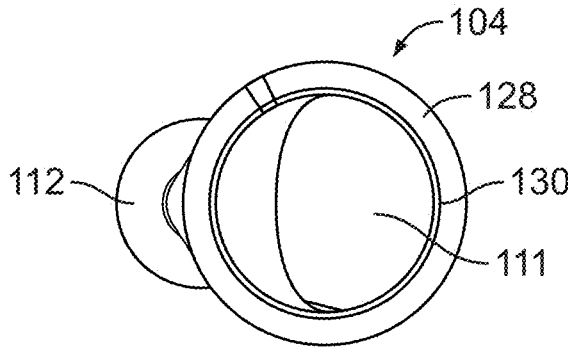
FIG. 1F illustrates an enlarged cross-sectional view of the support catheter taken along line A-A of FIG. 1A, showing the layers and dimensions of the tubular member wall and inner lumen.

The cylindrical wall defining the tubular member 104 can include an outer layer 128 and, as shown in the cross-sectional side view of FIG. 1F, an inner liner 130 defining the cross-sectional diameter of the tubular member 104. The outer and inner liners 128, 130 can comprise an extrusion of various materials, and may be reinforced with a metal frame structure, braid or coil, as further described herein.

In some examples, the support catheter 100 can have a nominal 4F dimension over the entire length of the tubular member 104, which may allow such catheters to be inserted through 5F, 6F, 7F or 8F guide catheters. The diameter and overall design of the tubular member 104 can be made to a smaller or larger diameter, depending upon the end use and indication. The inner diameter of the tubular member 104 shown in FIG. 1F is 0.052 inches and the outer diameter is 0.068 inches. In general, the lumen 111 of the tubular member 104 can be sized and shaped to accommodate the passage of one or more interventional devices therethrough. In some examples, an inner diameter of the lumen 111 of the tubular member 104 is not more than about one French smaller than an inner diameter of the lumen of a guide catheter/sheath through which the support catheter is extended during a medical procedure.

Figures 2A, 2B, 2C, 2D, 2E:
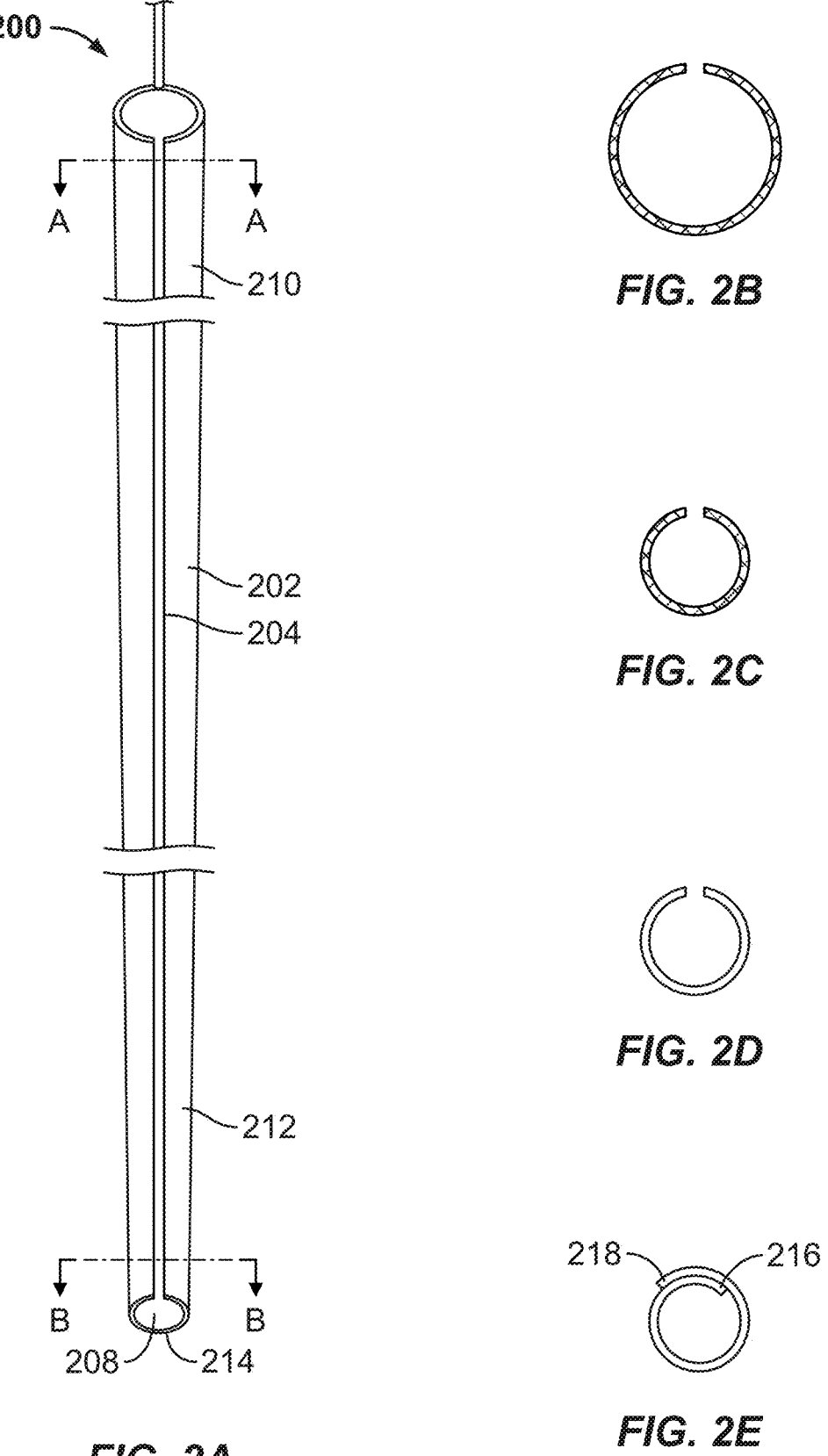
FIG. 2A illustrates a fragmented plan view of a support catheter comprising a tapered tubular member, as constructed in accordance with at least one embodiment.
FIG. 2B illustrates an enlarged cross-sectional view of the support catheter taken at line A-A of FIG. 2A.
FIG. 2C illustrates an enlarged cross-sectional view of the support catheter taken at line B-B of FIG. 2A
FIG. 2D illustrates an enlarged cross-sectional view of one embodiment of the support catheter taken at line B-B of FIG. 2A.
FIG. 2E illustrates an enlarged cross-sectional view of another embodiment of the support catheter taken at line B-B of FIG. 2A.

In general, the tubular member 104 can assume cross-sectional outer dimensions that allow the tubular member 104 to coaxially (i.e., in a tube-in-tube configuration, generally over the same longitudinal axis, with allowance for space between the tubes) slide into and through a guide catheter. The following discussion applies to the tubular member 104 when the longitudinal edges of the slit are touching or very close (e.g., within about 1 mm) to each other, as shown in FIG. 2B. For example, with a 6F guide catheter, the tubular member 104 can have an inner diameter that is about that of a 5F guide catheter, or any suitable desired diameter. In some embodiments, the inner diameter of the tubular member 104 may be not more than about one French smaller than the inner diameter of the guide catheter with which it is used. The difference between the inner diameters of the tubular member 104 and the guide catheter are related to the wall thickness of each and to the gap between the outer dimeter of the tubular member 104 and the inner diameter of the guide catheter, where the gap should be sufficient to allow the tubular member 104 to be advanced within the guide catheter. For instance, the gap in cross-sectional diameter between the inner diameter of the guide catheter and the outer diameter of the tubular member 104 may be less than and/or about 0.001 inches, 0.002 inches, 0.003 inches, 0.004 inches, or 0.005 inches, or any distance therebetween. In specific embodiments, the cross-sectional diameter gap may range from about 0.002 to 0.003 inches, or about 0.002 to 0.0035 inches. The diameter gap between an outer diameter of the tubular member 104 and the inner diameter of the guide catheter may be generally continuous along a substantial portion of the length or a majority of the length of the tubular member 104 in some embodiments, or the gap, and/or the difference between the inner diameters of the tubular member 104 and the guide catheter, can be varied along the length of the tubular member 104, e.g., in one embodiment the distal portion of the tubular member 104 can be tapered. In various embodiments, a guide catheter with any diameter may be used. The length of the tubular member 104 can be substantially less than the length of the guide catheter; however, the tubular member 104 can be designed with any length according to a desired application, such as about any of 6 to 45 cm, 10 to 35 cm, 14 to 25 cm, or 18 to 20 cm, or any other desired length. While the discussion above was provided in the context of the slit edges of the tubular member 104 touching or being very close (e.g., within about 1 mm) to each other, it is to be understood that these examples also apply when the slit edges are overlapping, as shown in FIG. 2E, with or without an interventional device being inside the tubular member 104, and further that these examples apply when the longitudinal edges of the slit are in a spread, expanded configuration because of an interventional device, as shown in FIG. 5D.

Figure 1G:
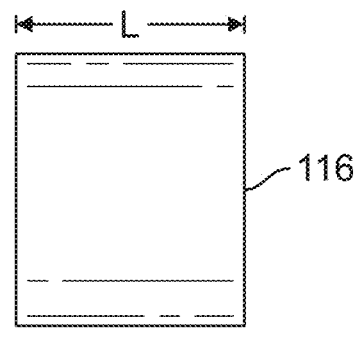
FIG. 1G illustrates a side view of the marker band included in the support catheter shown in FIG. 1A.
Figure 1H:
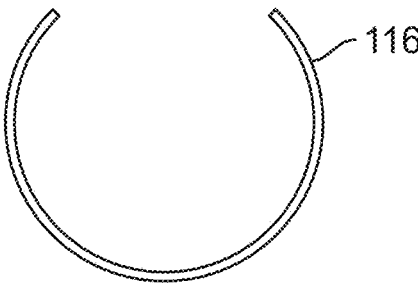
FIG. 1H illustrates a cross-sectional side view of the marker band shown in FIG. 1G.
Figure 1I:
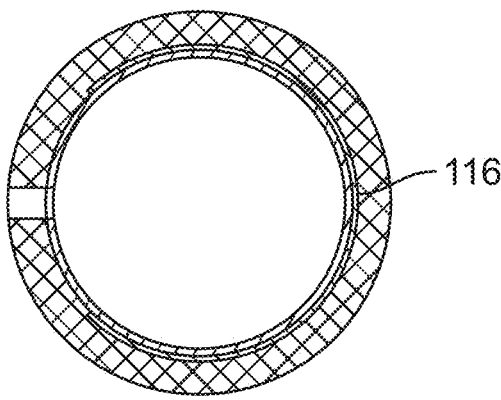
FIG. 1I illustrates a cross-sectional side view of the portion of the distal tubular member containing the marker band shown in FIG. 1H.

An optional marker band 116 of the support catheter 100 is shown in FIGS. 1G and 1H, with the transverse cross-sectional view of FIG. 1I illustrating an optional arrangement of the marker band 116 relative to the distal tubular member 104. FIG. 1G is a side view of the marker band 116, showing its length L, which may vary. In some embodiments, the length L of the marker band 116 may be about 0.04 cm. As noted above, the tubular member 104 itself may include a radiopaque material, such that no separate marker bands are included. Other embodiments, such as that shown, include one or more discrete marker bands having a defined length, which may range from less than or about 0.01 cm, or about any of 0.02 cm, 0.03 cm, 0.04 cm, 0.05 cm, 0.06 cm, 0.07 cm, 0.08 cm, 0.10 cm or longer, or any length therebetween.

The marker band 116 can have a substantially cylindrical configuration that extends around the circumference of the tubular member 104. The marker band 116 of FIG. 1H spans approximately 270° around the tubular member 104, leaving about 90° of the tubular member unmarked (plus-or-minus about) 30°, where the longitudinal slit 106 extends. In embodiments, the marker band 116 may extend less than or greater than 270° around the tubular member 104, for example spanning about any of 90°, 100°, 110°, 120°, 130°, 140°, 150°, 160°, 170°, 180°, 190°, 200°, 210°, 220°, 230°, 240°, 250°, 260°, 270°, 280°, 290°, 300°, 310°, 320°, 330°, 340°, 350°, 360°, or any value therebetween.

As further evident in FIG. 1H, the cross-sectional thickness of the marker band 116 may be small relative to the cross-sectional thickness of the wall of the tubular member 104. The inner diameter of the marker band 116 can be about 0.054 inches, plus-or-minus about 0.0002 inches, and the outer diameter can be about 0.056 inches, again plus-or-minus about 0.0002 inches. The marker band 116 may be symmetric or approximately symmetric (e.g., plus-or-minus) 10° with respect to the slit 106, as shown in FIG. 1I. The marker band 116 can comprise platinum-iridium, platinum-tungsten, or an alloy thereof. Alternatively, one or more marker bands can be formed by impregnating portions of the tubular member 104 with a radiopaque filler material, such as barium sulfate, bismuth trioxide, bismuth carbonate, powdered tungsten, powdered tantalum or the like. The marker band 116 may be of any desired flexibility or rigidity.

The support catheters disclosed herein, including support catheter 100, can be formed from one or more biocompatible materials, non-limiting examples of which may include metals, such as stainless steel or alloys, e.g., Nitinol, or polymers such as polyether-amide block copolymer (Pebax®), nylon (polyamides), polyolefins, polytetrafluoroethylene, polyesters, nylons, polyurethanes, polycarbonates or other suitable biocompatible polymers or composites and/or combinations of these. Generally, different sections of a support catheter can be formed from different materials from other sections, and sections of the catheter can comprise a plurality of materials at different locations and/or at a particular location. For example, a proximal extended rod/wire can be formed from metal, such as stainless steel. With respect to a tubular member, one material of particular interest can include a thermoplastic polymer with embedded reinforcing material, such as a wire, braid or coil that can be metal or suitable polymer or other material. Suitable polymer layer materials for the tubular member include, for example, polyamides, i.e., nylons, or Pebax®. The wire can be braided, coiled or otherwise placed over a polymer tubing liner with some tension. A polymer jacket is then placed over the top. Upon heating over the softening temperature of the polymer and subsequent cooling, the wire becomes embedded within the polymer. The liner and jacket can be the same or different materials. Suitable wire for embedding in the polymer includes, for example, flat stainless steel wire. The wire adds additional mechanical strength while maintaining appropriate amounts of flexibility.

The materials can be molded, extruded or the like, for example, based on well-known processing approaches in the field. Materials can be joined by softening one material and embedding the other material within the softened material, and/or using mechanical reinforcements, clamps, brackets or the like. Medical grade materials are generally commercially available for adaptation for forming the structures described herein. Curves can be introduced to polymer material through softening the polymer and hardening the polymer on a curved mandrel or the like.

As shown below in Table 1, the components included in embodiments of the disclosed support catheters, such as the outer extrusion of the tubular member, hypotube, and marker band, may, by way of example only, be comprised of one or more optional materials, including a thermoplastic elastomer (e.g., HYTREL SSD 20% $BaSO_4$), stainless steel (e.g., 304 SS), and an alloy (e.g., Pt 10% Ir), respectively.

TABLE 1

| Component | Material |
| --- | --- |
| Extrusion - Outer | HYTREL SSD 20% BaSO4 |
| Extrusion - Liner | PTFE |

TABLE 1-continued

| Component | Material |
| --- | --- |
| Hypotube Cover | Grilamid |
| Hypotube | 304 SS |
| Wire | 304 SS |
| Marker Band (MB) | Pt 10% Ir |

In some embodiments, expandable support catheters of the present disclosure can be characterized by the proximal end of the tubular member being of greater diameter than the distal portion. As shown in FIGS. 2A-2C, for instance, a support catheter 200 can include a distal tubular member 202 defining a longitudinal slit 204 extending from an angled proximal port 206 to a distal end opening 208. The tubular member 202 tapers in the distal direction, such that the proximal portion 210 has a greater diameter than the distal portion 212. It may be desired, in addition or alternatively, for the proximal end 210 to flare to a larger diameter than the rest of the tubular member 202. The tubular member 202 may taper by any desired amount, e.g., from just over 0 inches to about 1F to about 2F or more, from the proximal portion 210 to the distal portion 212. By way of illustration, if the support catheter 200 is configured specifically for use with a 6F guide catheter, the proximal portion 210 of the support catheter 200 can have a 5F outer diameter and the distal portion 212 can have a 4F outer diameter. The length of each discrete diameter portion may vary along the length of the tubular member 202. For example, the outer diameter might be about 5F over the proximal 90 mm, taper from about 5F to 4F over the next 90 mm, and be about 4F over the distal 90 mm of the tubular member 202. A support catheter for use with a 7F guide catheter might similarly taper distally from 6F to 4F across its length. In some embodiments, the distal portion 212 of the support catheter can taper less e.g., to 4.5F, or more e.g., to 3.0 or 3.5F. However, 4F may be the optimal balance, in some instances, between low profile/deliverability and reliable stent/balloon delivery system coverage. In some examples, it may be advantageous to have the tubular member 202 taper such that its distal tip 214 is only slightly greater than the diameter of a guidewire (e.g., approximately 0.014 inches for coronary use), which may have a solid structure or may an internal structure, such as a hollow lumen or core wire.

The outer diameter of the larger proximal portion 210 of the support catheter 200 may fit generally closely within the inner diameter of a guide catheter or sheath through which the support catheter 200 is inserted, thereby maximizing the diameter of the lumen defined by the tubular member 202 and increasing the overall support provided by the support catheter 200, while also accommodating unobstructed passage of interventional devices and contrast agents therethrough. The lower profile, smaller diameter of the distal portion 212 of the tubular member 202 can facilitate guide extension delivery down narrow, tortuous blood vessels. The cross-sectional views of FIG. 2B and FIG. 2C illustrate the larger cross-sectional diameter of the proximal portion 210 relative to the distal portion 212, along with the longitudinal slit 204.

The configuration of the tubular member 202 and its longitudinal slit 204 may vary. In some embodiments, the slit 204 can be defined by the parallel juxtaposition of opposing blunt edges or lips 216, 218 of the tubular member 202, such that the space between the opposing lips 216, 218 defines the width of the slit 204. In other examples, the lips 216, 218 can overlap in the pre-use (insertion) configuration, as shown in FIG. 2E, before coupling with an interventional device. According to such embodiments, the lips 216, 218 of the slit 204 can either overlap less or return to the non-overlapping configuration shown in FIG. 2D during or after insertion of an interventional device through the tubular member 202.

Figures 3A, 3B:
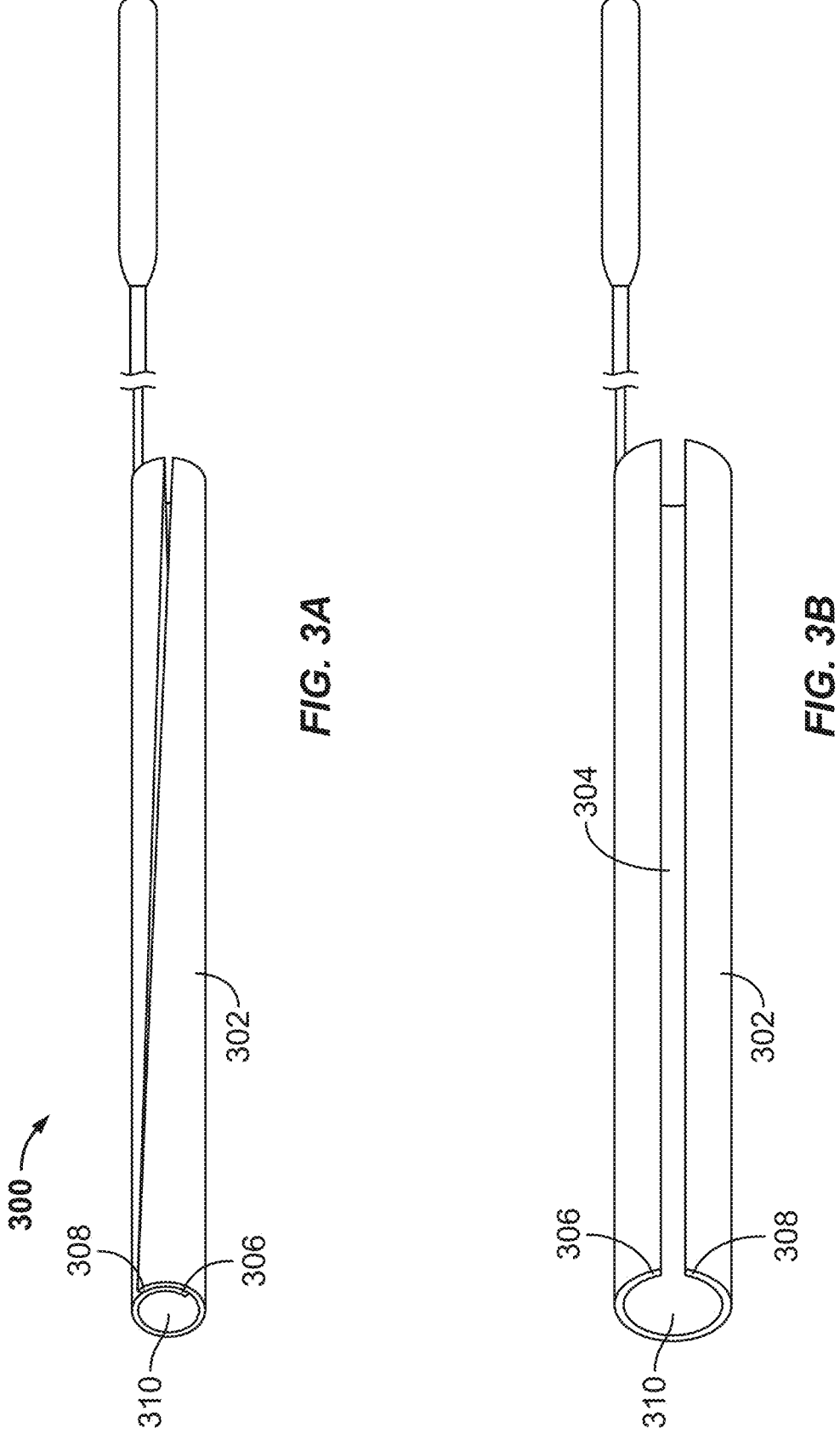
FIG. 3A illustrates a perspective view of a support catheter comprising a tubular member in a narrowed configuration, as constructed in accordance with at least one embodiment.
FIG. 3B illustrates a perspective view of the support catheter of FIG. 3A in an expanded configuration.

For example, the support catheter 300 shown in FIGS. 3A and 3B includes a tubular member 302 defining a longitudinal slit 304 configured to form and potentially expand until a gap of variable width is created between previously overlapping lips 306, 308. Such expansion may occur when an interventional device is being inserted into or removed from the lumen 310 of the tubular member 302. As the slit 304 of the support catheter 300 opens, circumferential coverage of the interventional device adequate to retain the device within the lumen 310 is maintained. This particular configuration can allow the tubular member 302 to curl down to very small diameters when navigating tight vessels and/or when used to advance an interventional device that is of sufficiently smaller outer diameter than the inner diameter of the tubular member 302. This configuration can also be beneficial during medical procedures that involve tracking the support catheter 300 directly over a guidewire, as the tight-curled configuration of the tubular member around the guidewire may prevent the guidewire from escaping the lumen 310 of the tubular member 302 through the slit 304. In additional examples, the edges or lips of the slit can interlock, such as in a keyed configuration, to prevent accidental removal of an interventional device inserted within the tubular member.

In some embodiments, support catheters of the present disclosure (e.g., any of the support catheters described herein) can incorporate a longitudinal slit that does not traverse the full length of the tubular member. For example, the support catheter 400 depicted in FIGS. 4A-4C comprises a tapered tubular member 402 and a longitudinal slit 404 having a proximal end 406 distal to the proximal port of the tubular member, such that the intervening section of the tubular member 402 is slit-free, as shown in the cross-sectional view of FIG. 4B. The proximal end 406 of the slit 404 can begin approximately at the beginning of the tapered portion of the tubular member 402 (cross-sectional view shown in FIG. 4C) and extend through the distal end 410 of the tubular member 402, such that the slit 404 spans about two-thirds of the length of the tubular member 402. The length of the slit 404 relative to the length of the tubular member 402 can vary. In some examples, the slit 404 may span at least about 50% of the length of the tubular member, or at least about 60%, 70%, 80%, 90%, 95%, more than 95%, or any length therebetween. Such partial slit embodiments can be useful in situations where the distal portion of the support catheter is inserted deep into a vessel of decreasing size, and the slit allows opposing lips to overlap and achieve a tapered tubular member of even smaller size.

Figure 5A:
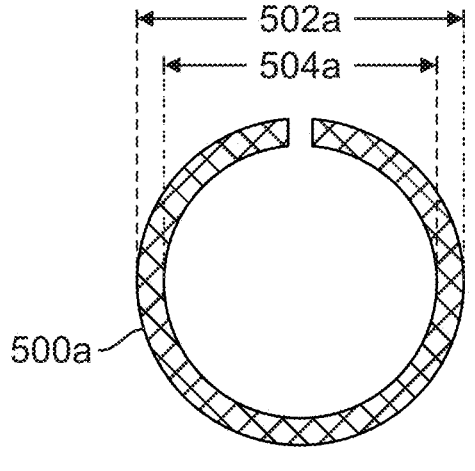
FIG. 5A illustrates an enlarged cross-sectional view of a tubular member of a support catheter, as constructed in accordance with at least one embodiment.
Figure 5B:
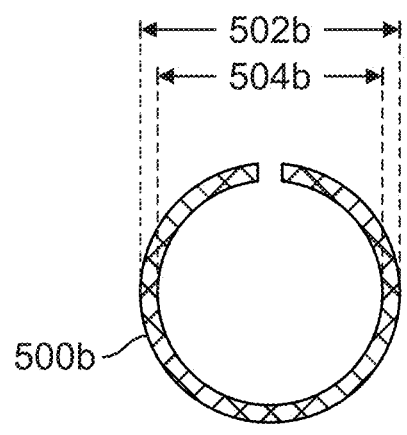
FIG. 5B illustrates an enlarged cross-sectional view of another tubular member of a support catheter, as constructed in accordance with at least one embodiment.
Figure 5C:
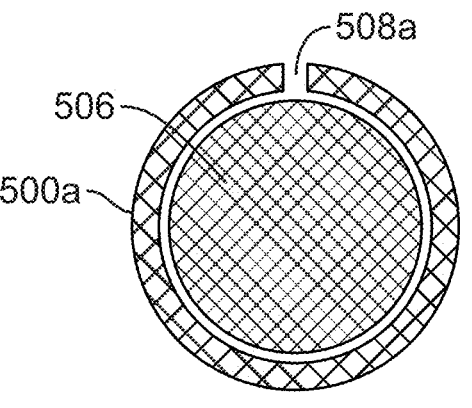
FIG. 5C illustrates an enlarged cross-sectional view of the tubular member of FIG. 5A after insertion of an interventional device therein.
Figure 5D:
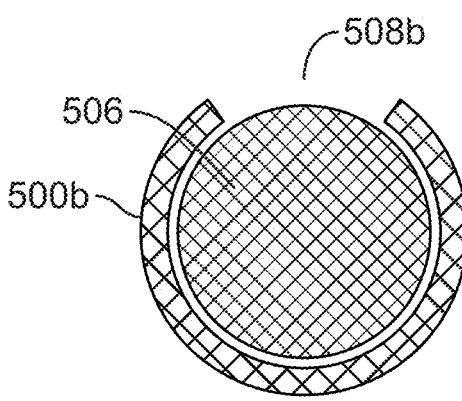
FIG. 5D illustrates an enlarged cross-sectional view of the tubular member of FIG. 5B after insertion of an interventional device therein.

Non-limiting, exemplary cross-sectional diameters of the disclosed tubular members before and after insertion of an interventional device are depicted in FIGS. 5A-5D. As shown in FIG. 5A, a 5F tubular member 500a can have an outer diameter 502a of about 0.067 inches and an inner diameter 504a of about 0.056 inches. The 4F tubular member 500b shown in FIG. 5B has an outer diameter 502b of about 0.053 inches and an inner diameter 504b of 0.046 inches. Upon insertion of an interventional device 506 through the 5F tubular member 500a, the slit 508a defined by the tubular member 500a may maintain the same or substantially the same width. Insertion of the same interventional device 506 through the tubular member 500*b* of the 4F catheter may cause the width of the slit 508*b* of the catheter to expand. The degree of expansion can vary depending on the number and cross-sectional size of the interventional device(s) and/or the material composition of the tubular member. In the example shown in FIG. 5D, accommodation of the interventional device 506 may cause the slit 508*b* of the 4F tubular member 500*b* to expand until it surrounds about 80% of the circumference of the interventional device 506. In other embodiments, the circumferential coverage of a tubular member remaining after an interventional device is inserted therein may vary, ranging from about 50% or more, such as about any of 55%, 60%, 65%, 70%, 75%, 80%, 85%, 90%, or more, or any value therebetween. Due largely to the hoop strength of the tubular member, the circumferential coverage of the interventional device provided by the surrounding tubular member after insertion of the interventional device therethrough may be sufficient to retain the interventional device in the lumen defined by the tubular member. The remaining coverage may also be sufficient to efficiently transfer (from the support catheter to the interventional device) push forces applied to the proximal end of the support catheter.

Figures 6, 7:
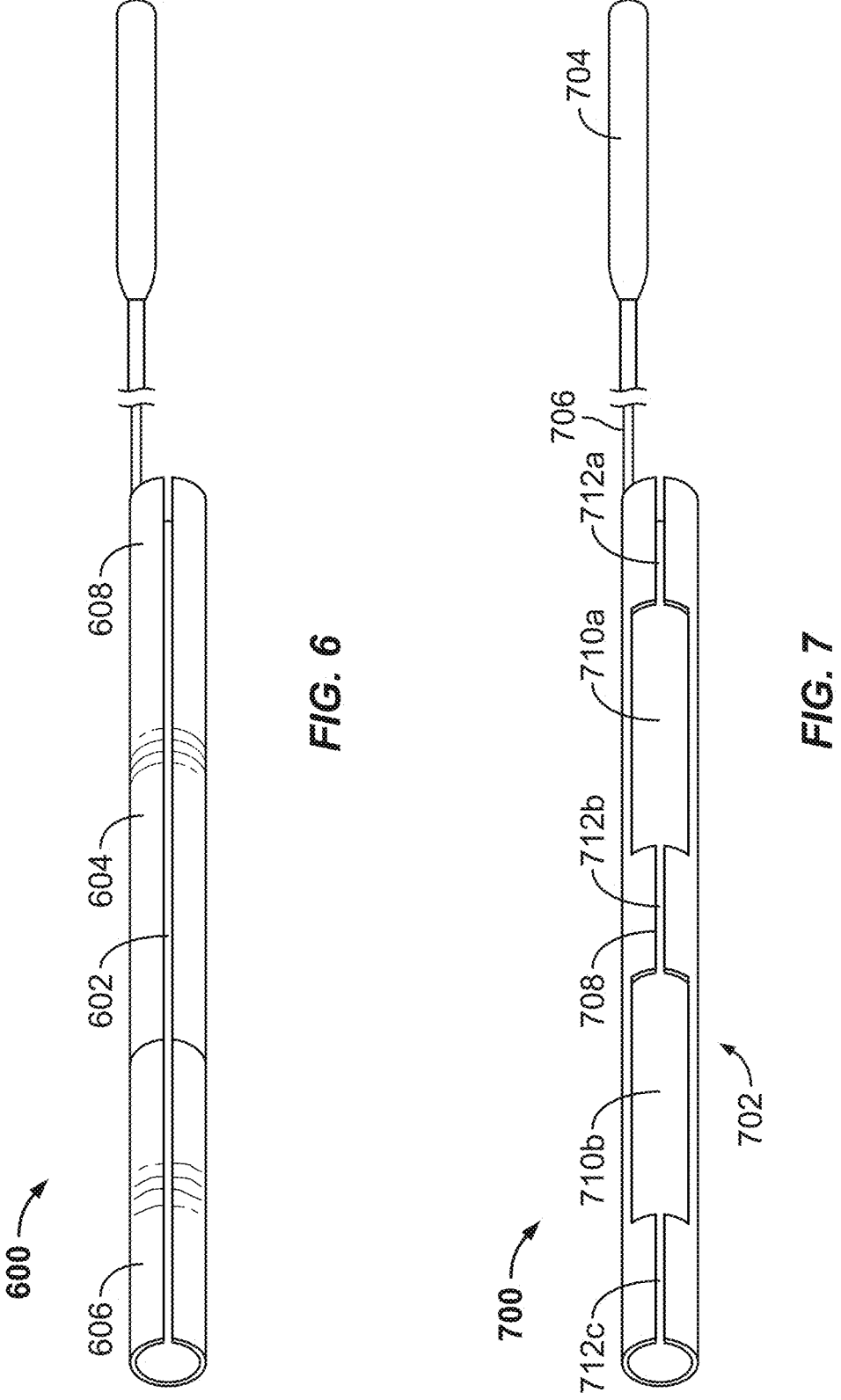
FIG. 6 illustrates a perspective view of a support catheter comprising a variable durometer tubular member, as constructed in accordance with at least one embodiment.
FIG. 7 illustrates a perspective view of another support catheter, as constructed in accordance with at least one embodiment.

In addition or alternatively, support catheters of the present disclosure (e.g., any of the support catheters described herein) can be characterized by the distal end of the distal tubular member being more flexible than the proximal end, as illustrated by FIG. 6, which may improve the maneuverability of the catheters within a patient's vasculature. As shown, a support catheter 600 can comprise a longitudinal slit 602 spanning at least a portion of a distal tubular member 604, which comprises a distal portion 606 that is softer than a proximal portion 608. The distal portion 606 may be constructed of a polymer (such as HYTREL, Nylon 12, or Pebax) of about 25D durometer to about 63D durometer. The proximal portion 608 may be constructed of a polymer (such as HYTREL, Nylon 12, or Pebax) of about 63D durometer to about 72D durometer.

The number of sections along the tubular member having different durometers may vary, ranging for example from two, three, four, five, or more sections. Additional embodiments can include a tubular member having, from its proximal end to its distal end, a soft or medium durometer polymer, followed by a harder durometer polymer, followed by a soft or medium durometer polymer. In some embodiments, the durometer may vary in a substantially seamless, continuous fashion along the length of the distal tubular member 604, such that discrete regions of uniform hardness may not be feasibly delineated. In some embodiments, the transverse cross-section of the distal tubular member may comprise materials having different durometer values. From a transverse cross-sectional perspective of the tubular member, for example, a bottom of the circular cross-section can be made of a softer durometer polymer than the top of the circular cross-section (where the slit is included) to resist unintentional deformation along each side of the slit. The tubular member 604 may have a hoop strength sufficient to resist unwanted opening along the slit 602 as the tubular member 604 is advanced through curves and bends within a vasculature.

In terms of flexural modulus, embodiments of a support catheter can include, starting at a distal end, a first portion having a flexural modulus of about 13,000 PSI plus-or-minus 5000 PSI, a second portion having a flexural modulus of about 29,000 PSI plus-or-minus 10,000 PSI, a third portion having a flexural modulus of about 49,000 PSI plus-or-minus 10,000 PSI, and a fourth portion having a flexural modulus of about 107,000 PSI plus-or-minus 20,000 PSI. Any number of rigidities can be used along the length of some or all portions of the device, as would be apparent to a person of ordinary skill in the art based on a reading of this disclosure.

In yet additional embodiments, the distal tip of the tubular member may be tapered and flexible, such that the tip can fold back into the lumen of the distal portion of the tubular member upon interacting with an interventional device. Folding back of the distal tip can increase the interventional device support provided by the support catheter, which may be advantageous after the interventional device has reached its target site. Proximal folding of the distal tip may therefore embody a transition in the primary function of the support catheter from catheter maneuvering assistance to interventional device support. Embodiments can also include a flexible, tapered distal tip configured to fold back onto the outer surface of the distal portion of the tubular member.

In some embodiments, expandable support catheters of the present disclosure (e.g., any of the support catheters described herein) can incorporate a longitudinal slit that varies in cross-sectional width along the length of the tubular member. Specific examples may include a longitudinal slit that forms or incorporates one or more enlarged cutout regions, as reflected by the non-limiting example of FIG. 7. The illustrated support catheter 700 includes a distal tubular section 702 opposite an optional handle 704, with a push member 706 positioned therebetween. A longitudinal slit 708 defined by the tubular member 702 includes a first cutout region 710*a* proximal to a second, distal cutout region 710*b*, with more narrow regions 712*a*, 712*b*, and 712*c* positioned therebetween. The support catheter 700 may better facilitate clipping of the support catheter over an interventional device. Embodiments may feature only one cutout region or more than two cutout regions, e.g., four, five, six, or more.

Figure 8A:
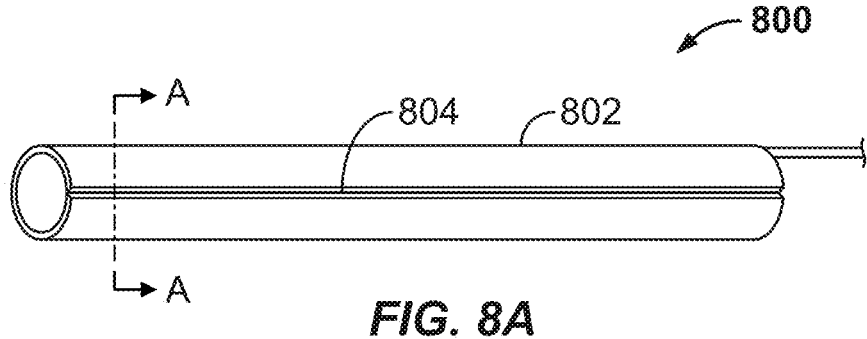
FIG. 8A illustrates a perspective view of a support catheter comprising a scored longitudinal slit, as constructed in accordance with at least one embodiment.
Figure 8B:
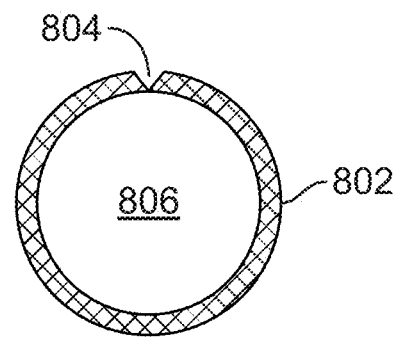
FIG. 8B illustrates an enlarged cross-sectional view of the support catheter taken at line A-A of FIG. 8A.
Figure 8C:
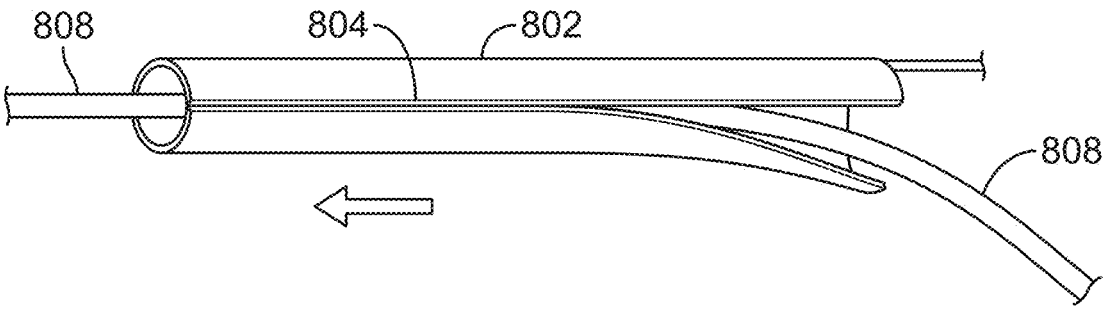
FIG. 8C illustrates a perspective view of the support catheter of FIG. 8A as the support catheter is being uncoupled from an interventional device.

In some embodiments, expandable support catheters of the present disclosure (e.g., any of the support catheters described herein) can incorporate a "scored" slit manufactured to extend less than 100% through the wall of the distal tubular member, as reflected by the non-limiting examples of FIGS. 8A, 8B, and 8C. The support catheter 800 includes a distal tubular member 802 having a longitudinal slit 804. The transverse cross-sectional view of the distal tubular member 802 depicted along line A-A in FIG. 8B illustrates the wedge-shape of the slit 804, which does not extend through the wall of the tubular member 802 into the inner lumen 806, such that the inner surface of the tubular member 802 remains fully intact. By having a slit initiated but not extending through the entire wall, a user may be able to use the support catheter like a currently marketed support catheter (loaded directly over a guidewire, or with the distal end of the guidewire, or back-loaded onto the interventional device prior to introducing the interventional device into the guide catheter). The scored slit enables the support catheter to function similar to currently marketed support catheters, but then be removed by tearing the slit and peeling the tubular member off of the interventional device after the support catheter is no longer needed unlike currently marketed support catheters. In addition or alternatively, a support catheter having a perforated slit could be used in a similar fashion. FIG. 8C shows an interventional device 808 being removed from the distal tubular member 802 of the support catheter 800 via the slit 804, which may tear in a proximal-to-distal direction during separation of the support catheter 800 and interventional device 808. In some examples, the support catheter 800 having the scored slit 804 may need to be placed before the interventional device 808. Where a scored slit is used, the frangible, intact, membrane-like portion of the tube may be on the tube's inner surface, outer surface, or in between. Alternatively, the slit can be a series of perforations. Where the frangible, intact portion of the tube is on the outer wall, it may be formed by molding the tubular portion over a mandrel that has a suitably shaped ridge formed longitudinally along the length of the mandrel, so that, when the tubular portion is molded over the ridge, the ridge leaves a score along the length of the tubular portion's interior.

Figure 9:
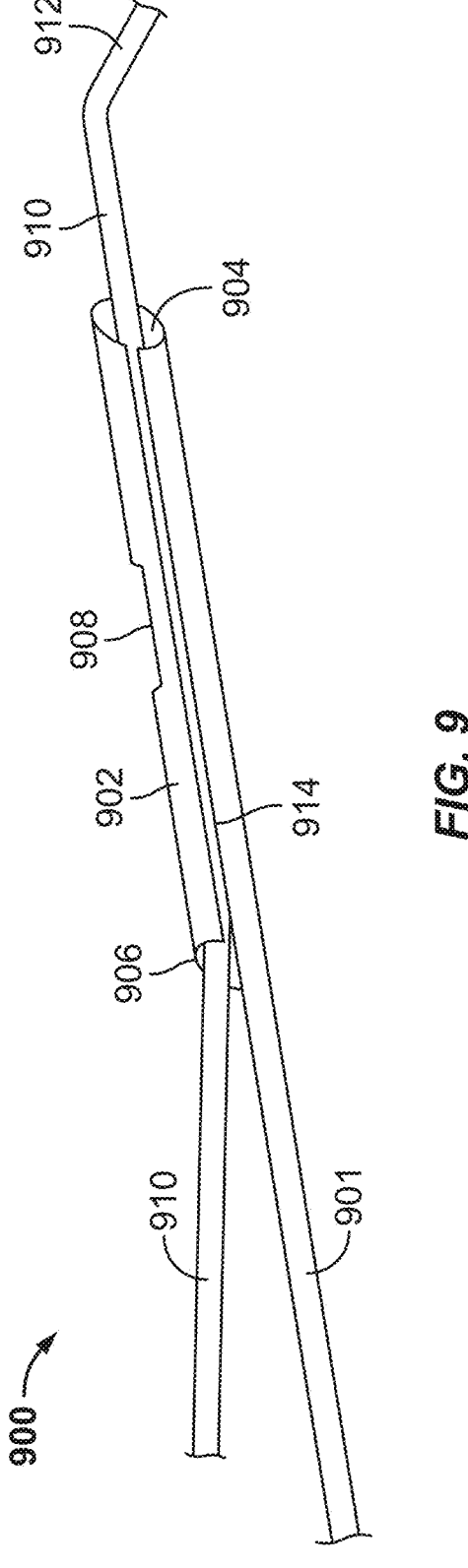
FIG. 9 illustrates a perspective view of a support catheter having a distal tubular structure defining a proximal side opening, as constructed in accordance with at least one embodiment.

Embodiments of the support catheters disclosed herein may feature a tubular member defining at least one side port. The support catheter 900 shown in FIG. 9, for instance, includes a proximal push member 901 and a tubular member 902. The tubular member 902 defines a distal end opening 904, a proximal port 906, and a side port 908. In addition to preventing backup, the support catheter 900 can deflect an interventional device, such as the illustrated guidewire 910, into a targeted branch vessel within a patient's vasculature, as further described in U.S. Pat. No. 10,173,029.

The side port 908 can be sized and shaped to facilitate exit of the distal tip 912 of an interventional device therethrough. In some examples, the side port 908 has a longitudinal length that is longer than, e.g., at least twice the diameter of, a guidewire. At least a portion of the tubular member 902 can have a durometer value that is approximately equal to or greater than the durometer value of the interventional device 910 to support the device as it is pushed through the side port 908. The tubular member 902 can have a flexibility sufficient to open and close over the interventional device 910 while also having a rigidity sufficient to remain over the device 910 as the tubular member 902 is pushed into position within a vessel. The longitudinal slit 914 can be formed with overlapping sections, sections that meet, and/or various locking sections.

In specific examples, the side port 908 has a longitudinal length of about 8 mm. The length of the tubular member distal to the distal end of the side port may be about 9 mm, 10 mm, 11 mm, 12 mm, 13 mm, 14 mm, 15 mm, or longer, or any length therebetween. The support catheter 900 can have one or more curved portions that deflect the side port 908 away from the longitudinal axis of the tubular member 902 spanning from the proximal port 906 to the distal end opening 904.

In some embodiments, adding a slit to the tubular element of the support catheter can entail a change to the co-extrusion of a metal braid or coil in the distal tubular portion in accordance with aspects of the present disclosure. Also, there may be changes to the radiopaque marker band from the ring-marker band used in some embodiments described herein.

There are multiple catheter construction options envisioned by the present disclosure. One or more versions of the support catheters discussed above may utilize some or all of these construction methods. In some embodiments, the distal tubular member of a support catheter can be extruded without a metal braid or coil reinforcement. In accordance with this approach, a polymer used to form the tubular member can be reflowed on top of an inner tubular liner (polymeric or lubricious such as PTFE). Polymer durometer may be varied along the shaft of a support catheter, with the lowest durometer segments being generally near the distal tip (e.g., as reflected by the non-limiting examples of FIGS. 1A, 1B, and 6). Additionally, a slippery coating (such as a hydrophilic or silicone coating) can be applied to the inner and/or outer surfaces of the tubular member to reduce friction during use. As noted above, at least a portion of a support catheter can be made radiopaque (visible under X-ray) by loading the polymers with radiopacifiers such as bismuth subcarbonate, barium sulfate or the like, and/or a split marker band of suitable flexibility is used, where the Pt—Ir marker contains a split and is usually embedded into the polymer near the distal tip (within 1 cm and preferably within 0.250 inches to 0.025 inches (e.g., as reflected by the non-limiting examples of FIG. 1E).

Figure 10:
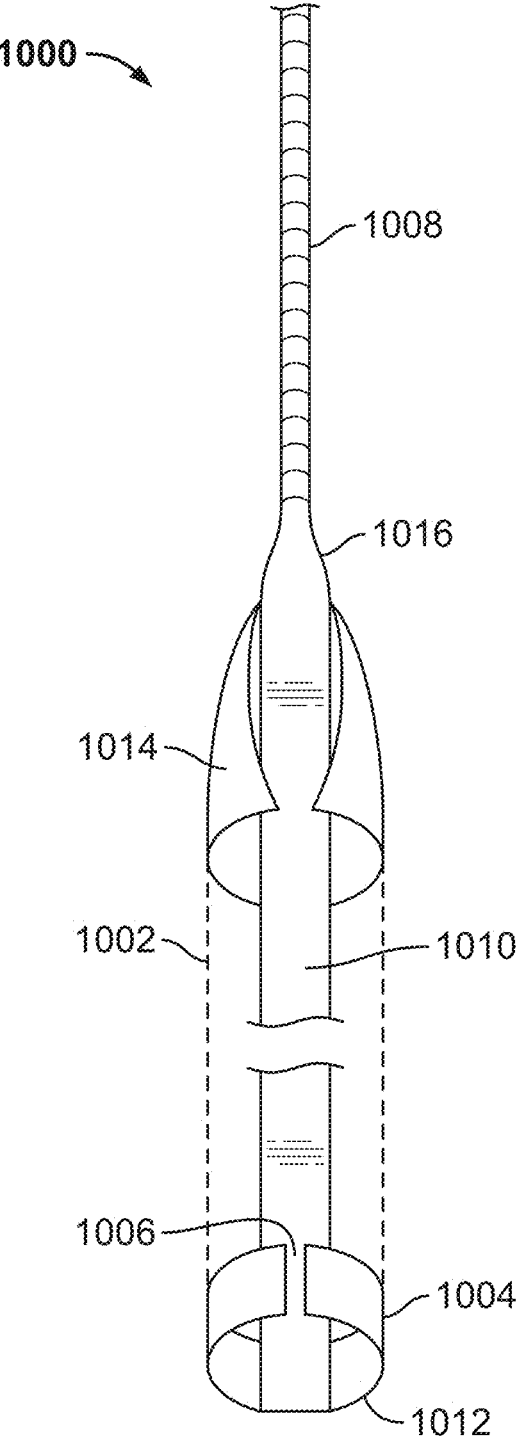
FIG. 10 illustrates a fragmented plan view of another support catheter, as constructed in accordance with at least one embodiment.

It may be advantageous to taper or flatten at least a distal portion of the push member, which may comprise a metal or other suitably rigid push shaft material in some examples, and attach it to the tubular member and/or the reinforcing material within and/or to a marker band of a tubular member using welding, adhesive, or bonding to improve tensile strength of the assembly as shown, for example, in the support catheter 1000 of FIG. 10, where the distal portion of the push member is connected to the marker band. In one embodiment, the support catheter 1000 includes a distal tubular member 1002 having a distal marker band 1004 defining a longitudinal slit 1006 opposite a proximal portion of a push member 1008 comprising a wire. The push wire 1008 includes an elongate flattened portion 1010 having a ribbon-like cross-sectional shape that can extend to or near the distal end 1012 of the tubular member 1002. The support catheter 1000 further includes a proximal transition portion 1014 that may be defined by a crescent or half-pipe shape that may be glued, welded or otherwise secured to the proximal-most flattened portion of the push wire 1016. By having a flat ribbon shape and extending the length of the tubular member 1002, the flattened portion 1010 of the push wire 1008 can provide a supportive "spine" to the tubular member 1002 and a larger surface area to secure the tubular member 1002. The flattened portion 1010 may also provide tensile strength to the tubular member 1002.

Figure 4A:
FIG. 4A illustrates a fragmented plan view of a support catheter comprising a shortened longitudinal slit, as constructed in accordance with at least one embodiment.
Figure 4A:
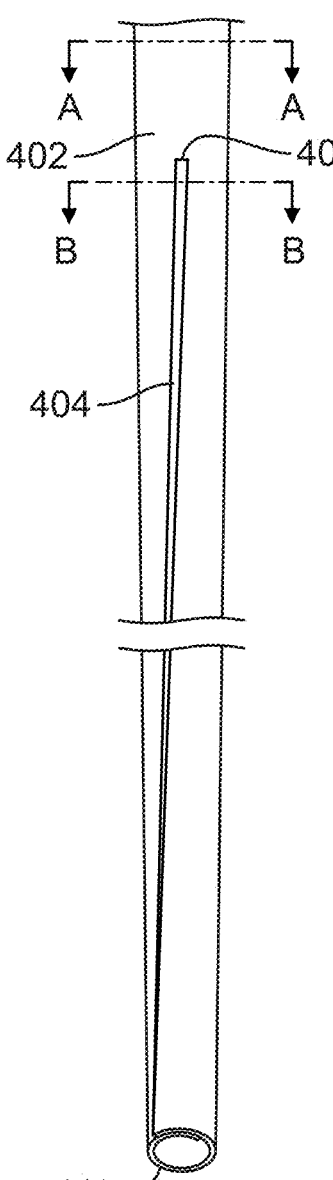
Figure 4B:
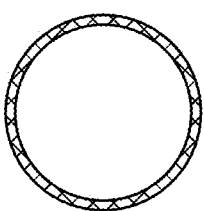
FIG. 4B illustrates an enlarged cross-sectional view of the support catheter taken at line A-A of FIG. 4A.
Figure 4C:
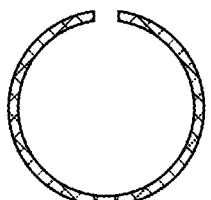
FIG. 4C illustrates an enlarged cross-sectional view of the support catheter taken at line B-B of FIG. 4A.
Figure 11:
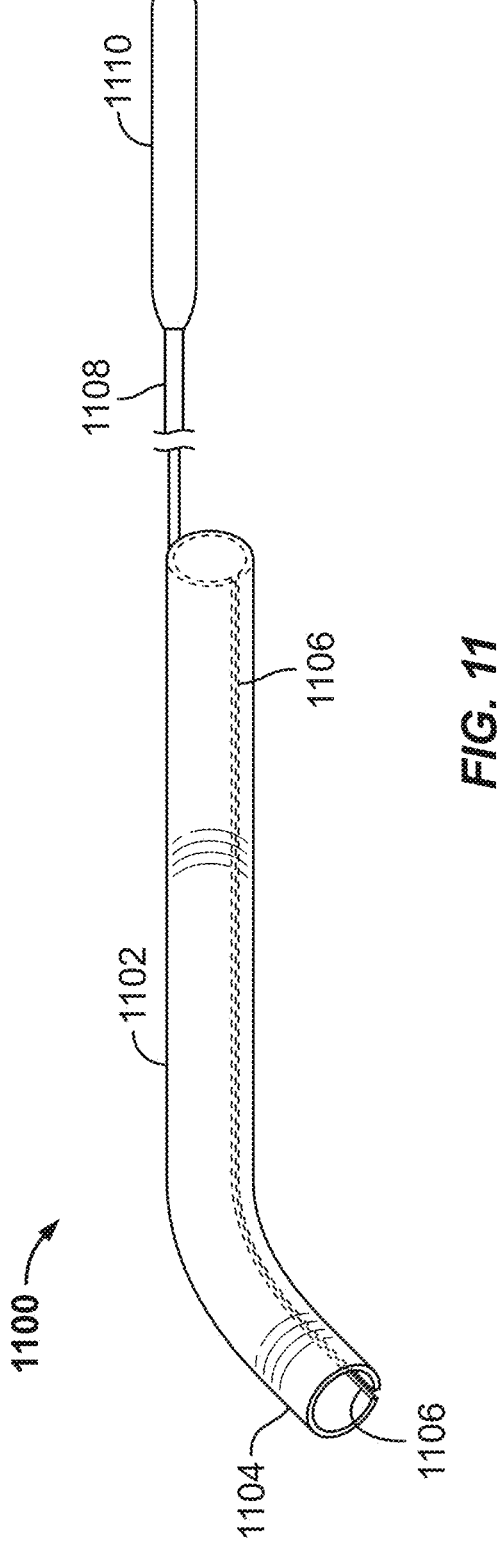
FIG. 11 illustrates a perspective view of a support catheter comprising a curved distal end, as constructed in accordance with at least one embodiment.

In one embodiment, the tubular member of the support catheter may be shaped with a curve, e.g., by heating and/or cooling in a curved shape to add a curve (e.g., as reflected by the non-limiting example of FIG. 11), or heated and cooled into a tapered configuration (e.g., as shown, for example, in FIGS. 4A-4C). The curved catheter 1100 shown in FIG. 11 includes a distal tubular member 1102 having a curved portion 1104 and a longitudinal slit 1106. A proximal push member 1108 and optional handle 1110 are also included. The slit may be on the inside of the curve, which can prevent or inhibit interventional devices from accidentally exiting the lumen of the tubular member via the slit during use, such as when the tubular member is navigating tortuous blood vessels. Multiple curved portions can be included at various points along the distal tubular member in different embodiments.

The tubular member of various support catheters can have radiused edges at the distal and/or proximal ends to facilitate entry and exit of interventional devices (e.g., as reflected by the non-limiting examples of FIGS. 12A-12C). In particular, the distal and/or proximal end of the tubular member may have a radiused outer surface, radiused inner surface, or radiused inner and outer surfaces. The circumferential wall 1202 of the distal end 1204 of the tubular member of FIG. 12A, for example, has a radiused outer surface 1206. The circumferential wall 1208 of the distal end 1210 of the tubular member shown in FIG. 12B has a radiused outer surface 1212 and inner surface 1214. The circumferential wall 1216 of the distal end 1218 of the tubular member shown in FIG. 12C has a radiused inner surface 1220. The liner, split radiopaque and/or metal marker bands, and hydrophilic coating, curve, and taper are additional configurations that can be used in a combination, or not at all for this and all design configurations. The edges may be rounded by heating, material removal, folding the end over on itself, adding material (different or the same), or other methods.

Figure 13A:
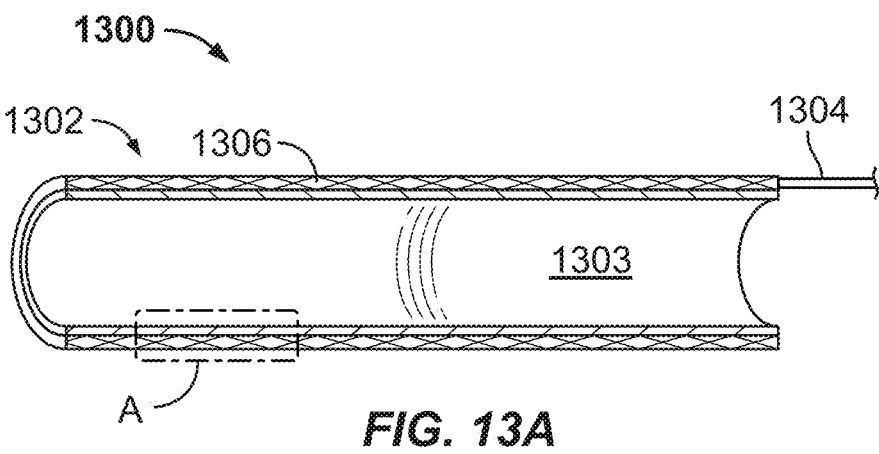
FIG. 13A illustrates a cross-sectional side view of a support catheter comprising a braided structure, as constructed in accordance with at least one embodiment.
Figure 13B:
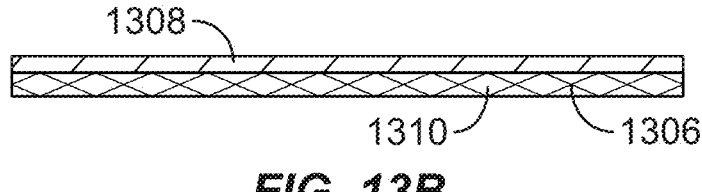
FIG. 13B illustrates an enlarged cross-sectional view of the support catheter taken at Detail A of FIG. 13A.

In some optional embodiments, the distal tubular member of a support catheter can contain one or more polymer layers and a reinforcement member, e.g., a braid or coil, so that the tubular member comprises a layered circumferential wall. In some embodiments, the braid (or coil, longitudinal supports, or other reinforcing layers or material or materials) may be loaded over a liner and reflowed with an outer polymer so that the braid (or other reinforcement) is encapsulated. The assembly is then slit, as generally reflected by the longitudinal cross-sectional view of FIG. 13A. The support catheter 1300 includes a distal tubular member 1302 formed in accordance with such embodiments. The tubular member 1302 defines an inner lumen 1303 and the support catheter 1300 includes a push member 1304 proximal to the distal tubular member 1302. A braided layer 1306 of the tubular member 1302 is enclosed within an inner liner 1308 and an outer polymer 1310, as shown more closely in the enlarged view of Detail A of FIG. 13B. The inner liner 1308 may constitute a polymer layer comprised of, or coated with, silicone, polytetrafluoroethylene (PTFE) or another lubricous material to provide a slippery surface for received interventional devices. The outer polymer 1310 may constitute a polymer layer comprised of one or more flexible materials, such as polyurethane, polyethylene or polyolefin of sequentially diminishing durometers along the tubular member's length, and it can be coated with a friction-reducing material (e.g., a hydrophilic or silicone material) to facilitate insertion and trackability through the vasculature and a guide catheter or sheath. The braided layer can comprise stainless steel or platinum alloy, for instance, and can extend between the polymer layers along at least a portion of the tubular member. Any suitable polymeric, metal, composite, or other suitable materials, or combinations of these, may be used, for any desired component, aspect, portion or portions of the support catheter, as a person of ordinary skill in the art reading this disclosure would appreciate.

Figure 13C:
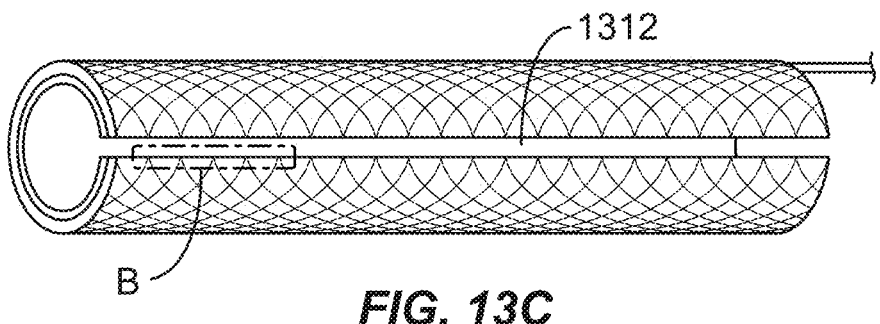
FIG. 13C illustrates a side view of the support catheter shown in FIG. 13A.
Figure 13D:
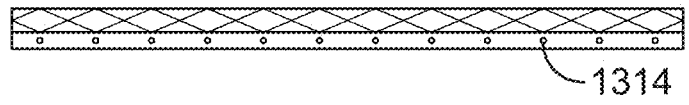
FIG. 13D illustrates an enlarged cross-sectional view of the support catheter taken at Detail B of FIG. 13C.

The side view of FIG. 13C illustrates the longitudinal slit 1312 of the catheter 1300, and FIG. 13D provides a magnified view of Detail B, which shows one edge 1314 of the slit 1312, revealing the cross-section of the braided layer 1306 exposed upon flush-cutting the tubular member 1302 to form the slit 1312.

Figure 14A:
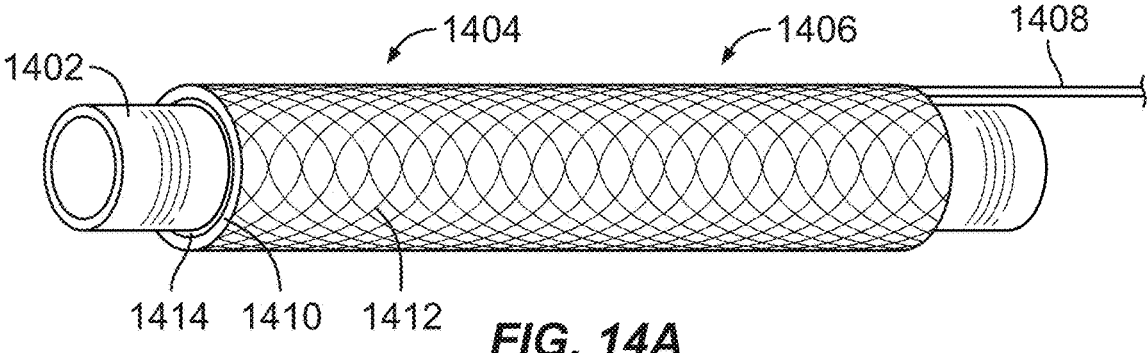
FIG. 14A illustrates an initial step of a method of forming a support catheter in accordance with at least one embodiment.
Figure 14B:
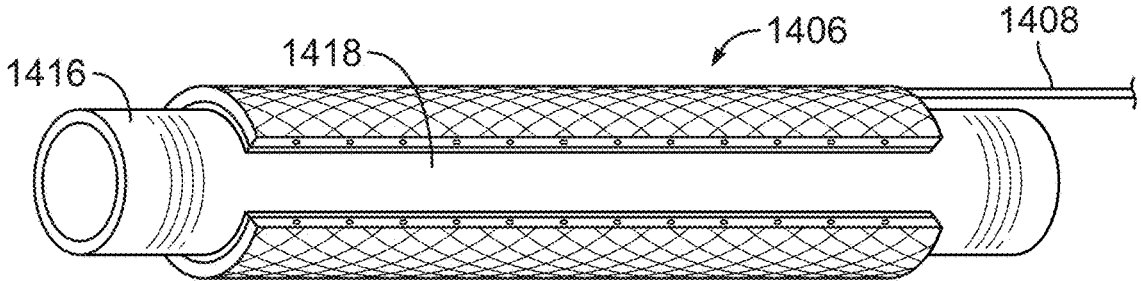
FIG. 14B illustrates a subsequent step of the method.
Figure 14C:
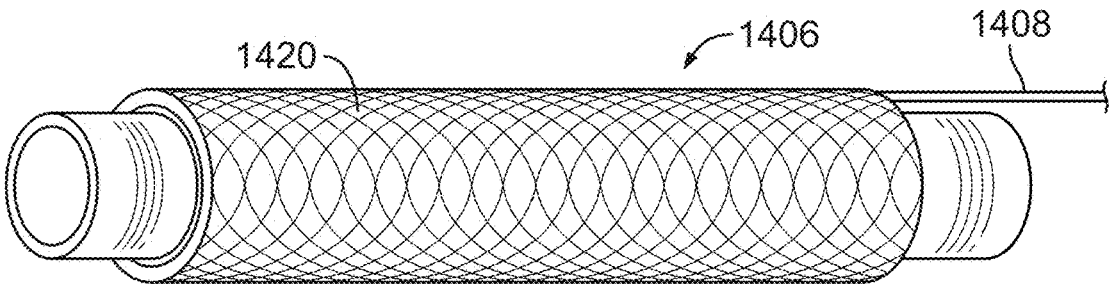
FIG. 14C illustrates a subsequent step of the method.
Figure 14D:
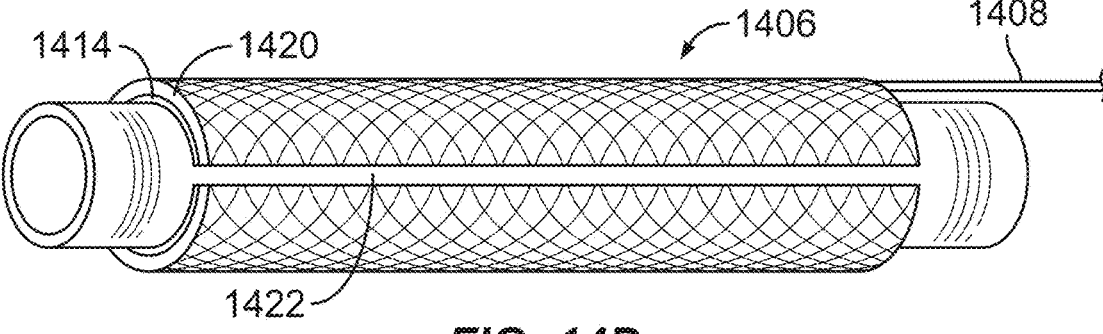
FIG. 14D illustrates a subsequent step of the method.

FIGS. 14A-14D depict a braided-catheter manufacturing process 1400 implemented using at least one mandrel. As shown in FIG. 14A, the process 1400 may involve inserting a first mandrel 1402 through a preliminary, slit-free distal tubular member 1404 of a catheter 1406 opposite a push member 1408. The distal tubular member 1404 includes a first layer of polymer 1410 that has been reflowed on top of a cylindrical braid 1412 and inner liner 1414, all of which define an inner lumen having a diameter that is smaller than the targeted diameter of the final distal tubular member. The distal tubular member 1404 is then slit and loaded onto a second, larger mandrel 1416 which spreads the slit 1418 open. A second outer layer of polymer 1420 is then reflowed over the braid 1412 to encapsulate the braid and cover the slit 1418, as shown in FIG. 14C. The tubular member 1404 is then cut again, as shown in FIG. 14D, to form the final slit 1422. An optional goal of all embodiments is to ensure there are no sharp metal braid edges protruding through the polymeric surfaces. It may be advantageous to taper the metal push rod shaft and attach it to the braid and/or marker band to improve tensile strength of the assembly.

Alternatively, a non-metallic material can be used instead of a metallic braid or coil, such as a layer of woven Dacron or carbon fiber (or similar material). According to such embodiments, the slit can be cut through the tube, including through the Dacron or carbon fiber layer.

Figures 15A, 15B:
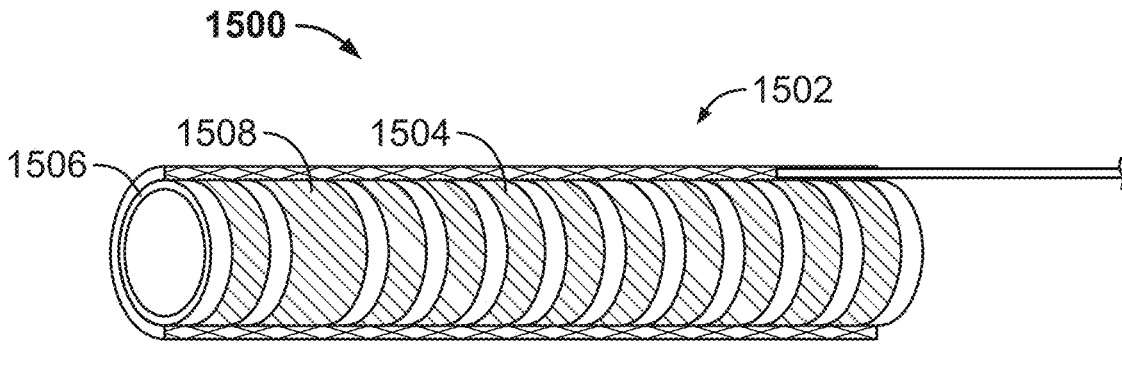
FIG. 15A illustrates a cross-sectional side view of a support catheter comprising a metal support structure, as constructed in accordance with at least one embodiment.
FIG. 15B illustrates a perspective view of the support catheter shown in FIG. 15A.

In other embodiments, a metal "ribbon" or "coil" is added to the distal tubular member instead of or in addition to the metal braid. For example, FIG. 15A shows a support catheter 1500 comprising a distal tubular member 1502 having a metal ribbon or coil 1504 surrounding an inner liner 1506. A split distal marker band 1508 is also included in the tubular member 1502. One or more proximal metal collars might be attached to the ribbon or coil. The perspective view of FIG. 15B also shows the longitudinal slit 1510 of the tubular member 1502 and the metal ribbon or coil 1504 exposed at an edge of the slit.

In other embodiments, a metal stainless steel tube can be cut into a pattern to provide flexibility, and then reflowed into the tubular assembly. The pattern can be stacked end-to-end and co-extruded. The metal structure can be cut so that it extends around approximately 80-90% of the circumference of the distal tube, allowing for the longitudinal slit to be added to the portion lacking the metal structure. Although this production method may be slightly more complex than adding a metal braid, it provides multiple potential benefits. Laser-cutting of stents from 316 SS tubes using this technique can be relatively inexpensive, for example. Many cut patterns can be used to form the tubular member, including options which add a "spine" to the extruded tubular member. The flexibility of the tube may vary over its length by having a row of stent-like frames with different patterns, by altering the strut (tube) thickness, or by changing the strut width. Additional components, such as a distal marker band and a cuff and segment for attaching to the push wire at the proximal end can be laser cut as part of their respective patterns. The patterns can be designed to interdigitate and align when a row of patterned metal structures is stacked together. Different alloys, such as cobalt chrome or platinum chrome, can be used for some or all of the stents, to increase radiopacity. One such design creates radial flexibility but prevents longitudinal compression and/or elongation. Non-limiting examples of optional patterned tubes are provided in the views of FIGS. 16A-16J and described below.

Figures 16A, 16B, 16C, 16D:
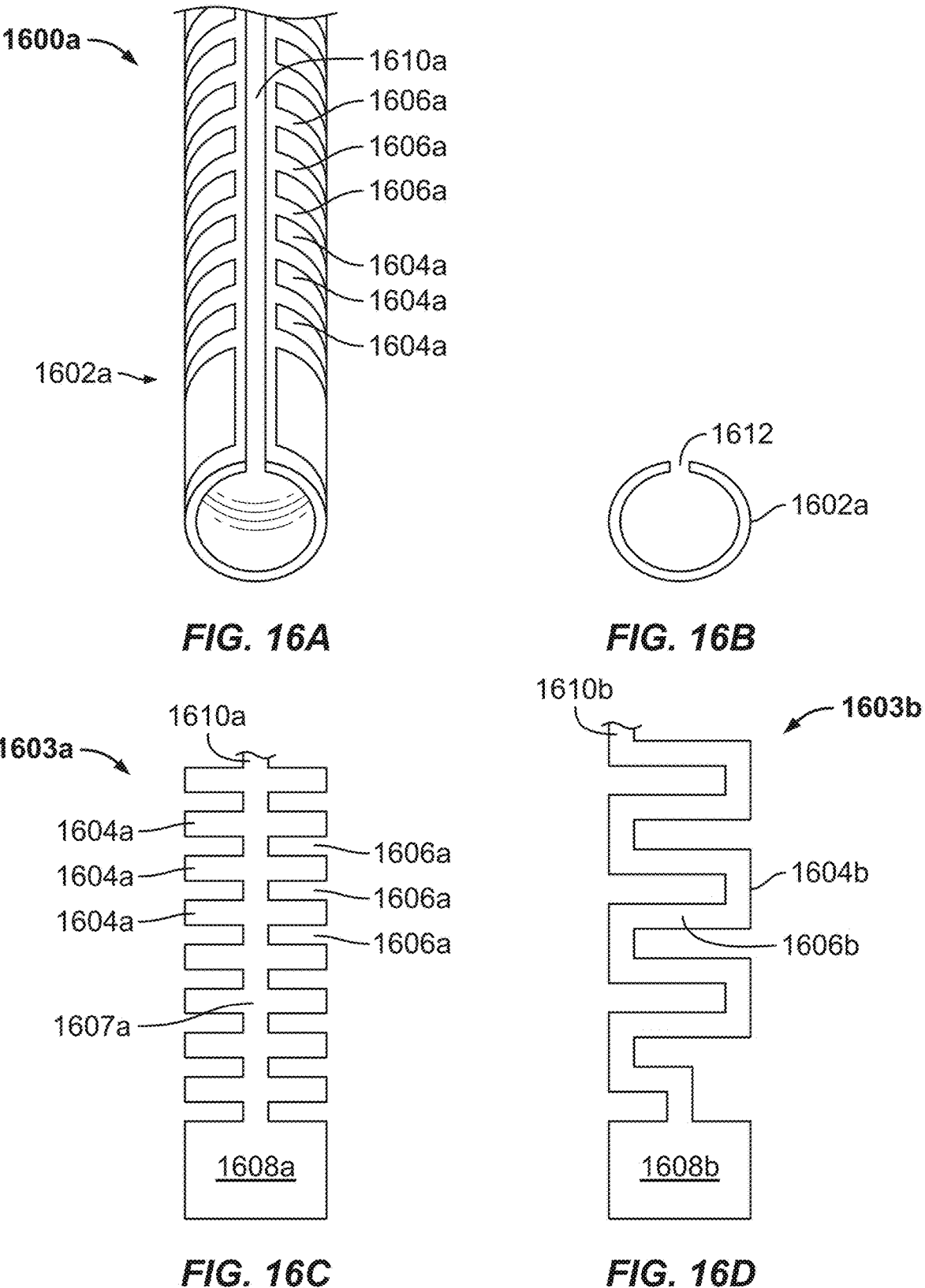
FIG. 16A illustrates a perspective view of a tubular member of a support catheter comprising a metal support frame, as constructed in accordance with at least one embodiment.
FIG. 16B illustrates a cross-sectional transverse view of the tubular member shown in FIG. 16A.
FIG. 16C illustrates a plan view of the metal support frame of the tubular member shown in FIG. 16A.
FIG. 16D illustrates a plan view of an alternate embodiment of a metal support frame that can be included in the tubular member shown in FIG. 16A.

FIGS. 16A-16C show a support catheter 1600*a* having a distal tubular member 1602*a* comprised of a ladder-like metal frame 1603*a* defined by a plurality of parallel ribs 1604*a* and gaps 1606*a* interleaved therebetween. A longitudinal "spine" 1607*a* spans the length of the frame 1603*a*, integral with and connecting the prongs 1604*a*. As shown in the perspective view of FIG. 16A and the plan view of FIG. 16C, the distal end 1608*a* of the frame 1603*a* can have a larger surface area than each of the individual prongs 1604*a* to accommodate placement of a marker band, among other things. The proximal end 1610*a* can be attached to or formed integrally with another frame having the same pattern or a different pattern. The slit 1612 of the tubular member 1602*a* is visible in the transverse cross-sectional view of FIG. 16B. The slit 1612 may be positioned approximately opposite the spine 1607*a* in some embodiments.

FIG. 16D shows a snake-like frame 1603*b* that may be used to form the distal tubular member of a support catheter in a similar manner. The snake-like frame 1603*b* can be defined by a series of longitudinal segments 1604*b* of metal connected by lateral segments 1606*b* of metal that culminate in a distal end 1608b having a broad surface for integration of a marker band, for example. Like frame 1603a, frame 1603b can be stacked with another frame at its proximal end 1610b.

Figures 16E, 16F, 16G:
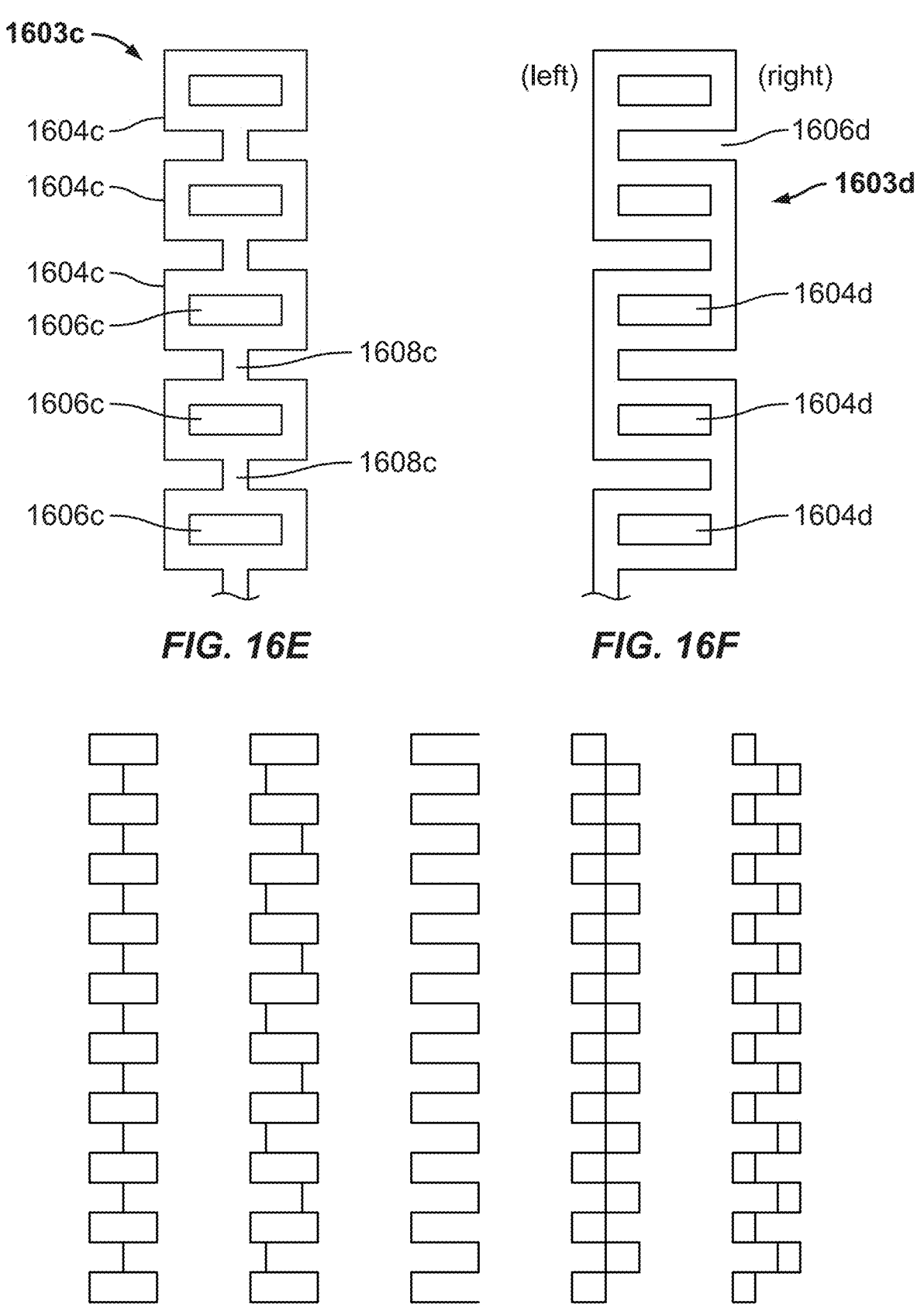
FIG. 16E illustrates a plan view of an alternate embodiment of a metal support frame that can be included in the tubular member shown in FIG. 16A.
FIG. 16F illustrates a plan view of an alternate embodiment of a metal support frame that can be included in the tubular member shown in FIG. 16A.
FIG. 16G illustrates a plan view of an alternate embodiment of a metal support frame that can be included in the tubular member shown in FIG. 16A.

FIG. 16E illustrates the configuration of a stent-like metal frame 1603c that can be cut from a metal tube and used for a tubular member. The frame 1603c comprises a series of box-like sections 1604c each defining a central aperture 1606c. A series of comparatively short longitudinal segments 1608c connect the box-like sections 1604c and provide the longitudinal "spine" of the frame 1603c. The pattern of the frame 1603c can repeat to lengthen the longitudinal dimension of the tubular member formed therefrom, and/or the frame 1603c can be attached end-to-end with one or more additional frames to form an elongate tubular member comprised of a series of individual frames.

The stent-like frame 1603d illustrated in FIG. 16F also defines a series of box-like structures 1604d, but with lateral gaps 1606d therebetween. Successive gaps 1606d alternate between opening to the left or right of the structure 1603d with respect to the orientation of the illustrated plan view.

FIG. 16G shows five additional examples of stent-like frames that may be utilized to form the tubular member of a support catheter in accordance with the present disclosure. The particular configuration of each frame may vary, and as evidenced by FIG. 16G, the frames may comprise a series of repeating features that together define a unitary structure. The frames may include or lack a distinct spine feature extending substantially parallel to the longitudinal axis of the resulting tubular member.

Figures 16H, 16I, 16J, 16K:
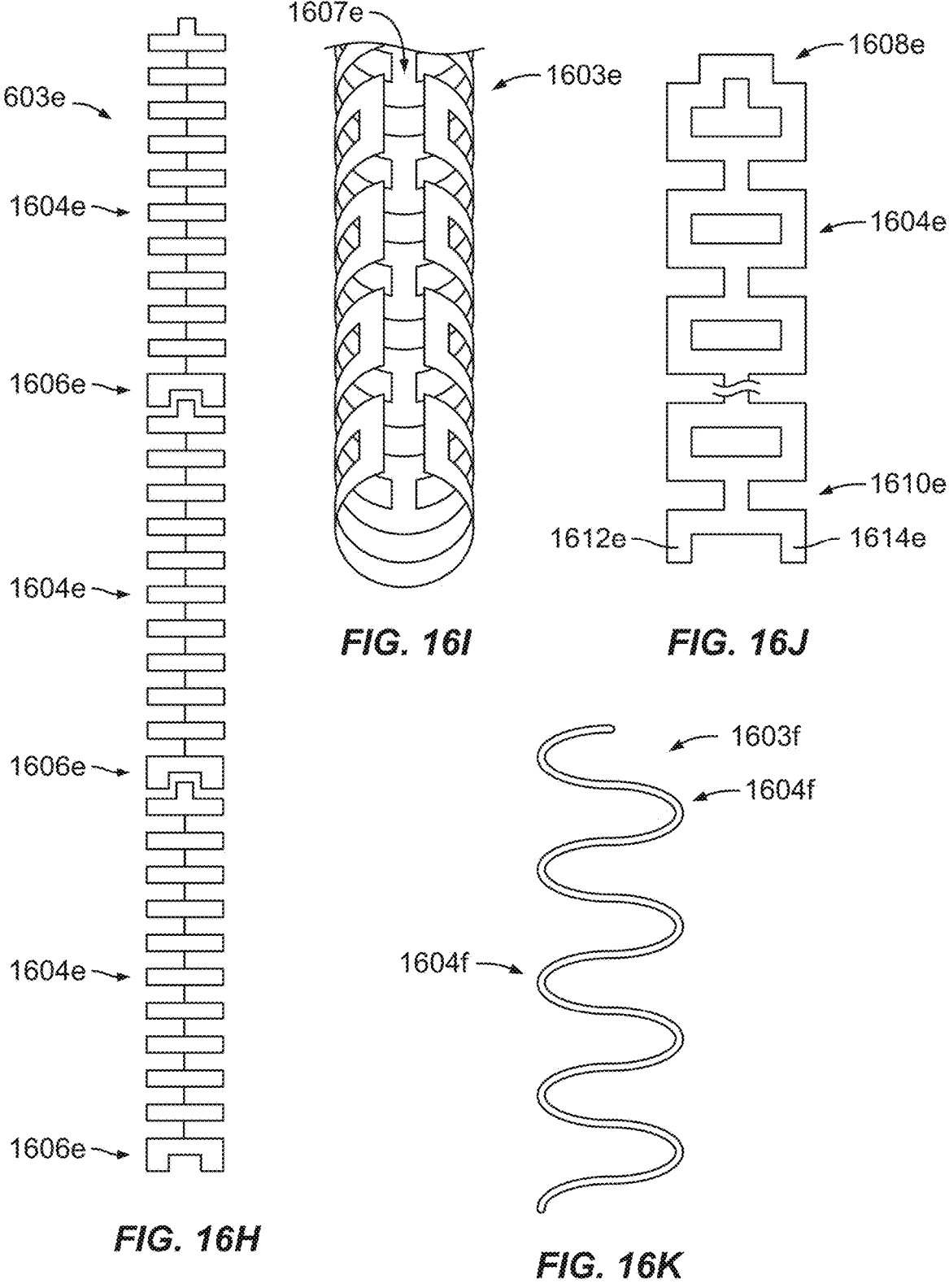
FIG. 16H illustrates a plan view of an alternate embodiment of a metal support frame that can be included in the tubular member of a support catheter.
FIG. 16I illustrates an enlarged perspective view of a portion of a tubular member that comprises the metal support frame shown in FIG. 16H.
FIG. 16J illustrates a fragmentary plan view of a portion of the metal support frame shown in FIG. 16H.
FIG. 16K illustrates a plan view of an alternate embodiment of a metal support frame that can be included in the tubular member of a support catheter.

FIGS. 16H-16J illustrate an embodiment of a stent-like frame that includes interdigitating features. The frame 1603e illustrated in FIG. 16H comprises a series of stent-like sections 1604e arranged in a row. The sections 1604e are connected via interdigitating features 1606e, which align the stent-like sections 1604e. FIG. 16I shows a perspective view of a distal portion of a distal tubular member 1602a comprised of the frame 1603e formed after curling the frame into a cylindrical shape. The gap 1607e left between opposite lateral ends of each frame section 1604e provide a space for subsequent formation of a longitudinal slit. FIG. 16J is a magnified view of a section 1604e of the frame 1603e, showing a first interdigitating component 1608e opposite a complementary interdigitating component 1610e. To stack two or more sections 1604e in series, the first interdigitating component 1608e may be inserted between the two parallel prongs 1612e, 1614e constituting the complementary interdigitating component 1610e.

FIG. 16K illustrates yet another configuration of a patterned frame 1603f that can be used to form the distal tubular member of a support catheter. The frame 1603f comprises opposing rounded ends 1604f collectively resembling a coiled wire or spring. These ends, which may be overlapping, may prevent unintentional dislodgment of an interventional device through the longitudinal slit of a support catheter. The frame 1603f, by way of non-overlapping slit sides, may also increase or maximize the inner diameter of the tubular member formed therefrom, unlike frame designs featuring overlapping sides of the longitudinal slit, for example. The design of FIG. 16K is similar to that of FIG. 16D, in that it may be a continuous material (or discontinuous, as appropriate), but it may be formed from a metal wire formed into a serpentine configuration, or cut or formed from a nylon or other polymeric material, which then is wrapped, folded, or otherwise formed into the distal tubular member.

Figure 17:
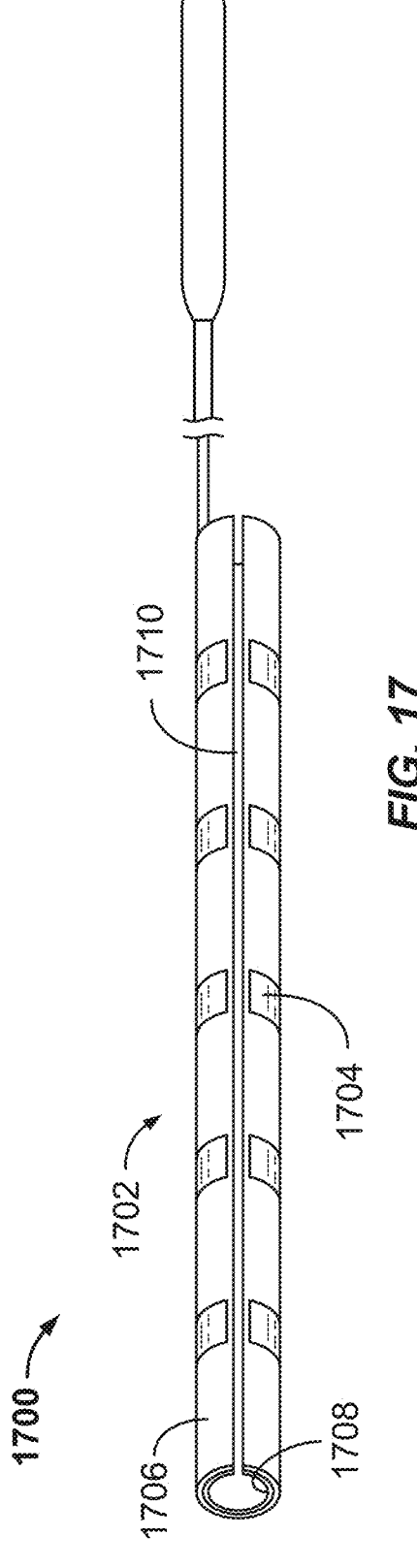
FIG. 17 illustrates a perspective view of a tubular member of a support catheter comprising embedded metal bands, as constructed in accordance with at least one embodiment.

In some embodiments, the support catheters of the present disclosure can incorporate one or more metal split bands of any desired flexibility (or rigidity) throughout the length of the distal tubular member, as shown for example in FIG. 17. Support catheter 1700 includes a distal tubular member 1702 comprised of a plurality of steel bands 1704 embedded within an outer polymer layer 1706, which radially surrounds an inner liner 1708. The bands 1704 can comprise a radiopaque material such as platinum-iridium, steel (e.g., 316 SS), or a combination thereof to ensure visibility in some regions and greater clamshell (radial) force in others. Applying metal bands to the tubular member 1702 may improve its radial force (ensuring the tubular member resists buckling or kinking) and bias the slit 1710 into the closed configuration. By adding one or more bands 1704 to the length of the tubular member 1702, the manufacturer can advantageously control areas where more radial force or force to keep the slit closed is required.

As further disclosed herein, a push member can be included in a support catheter, such as the support catheter 1800a depicted in FIG. 18A, which includes a distal tubular member 1802a and a push rod 1804a. The push rod 1804a can generally be a metallic, polymeric, or other suitably rigid structure, or combinations of these, integral with and/or connected to the distal tubular member 1802a, and can optionally include one or more of the features described in greater detail herein.

Figure 18H:
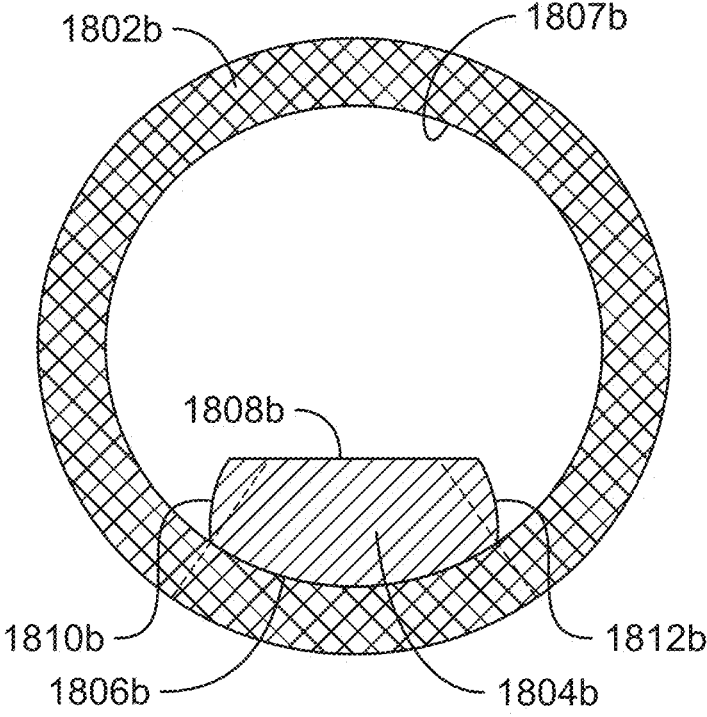
FIG. 18H illustrates an enlarged cross-sectional view of a push member that can be included in the support catheter of FIG. 18A, taken along line A-A.

The transverse cross-sectional shape of the push rod 1804a may be substantially round (FIG. 18B), oval (FIG. 18C), square (FIG. 18D), rectangular (FIG. 18E), half-moon concave (FIG. 18F), or flat (18G). A possible goal is to allow adequate force for push, but still allow flexibility for the tubular member 1802a to track through curves and turns of various blood vessels. It may also be a goal to allow as much cross-sectional space as possible between the outer diameter of the interventional device and the inside of the guide catheter. The cross-sectional shape of the push rod 1804a may vary along the length of the push rod 1804a, e.g., the push rod 1804a may be round (as shown in FIG. 18B) at a proximal portion and concave at a distal portion (as shown in FIG. 18F). Other configurations and combinations may be used (e.g., a portion or portions of the push rod 1804a could be of the configuration discussed below from FIG. 18H).

FIG. 18H illustrates another potential cross-sectional shape of at least a portion of a push member, a proximal portion of which is shown together with a guide catheter 1802b. The cross-sectional shape of the illustrated push member 1804b can be defined by an arcuate first surface 1806b and a second surface 1808b positioned opposite the first. The arcuate first surface 1806b may have an outer curvature that matches the inner surface 1807b of the guide catheter. The second surface 1808b may be flat or substantially flat and it may be spaced furthest from the first surface 1806b at its center point. Two side arcuate surfaces 1810b, 1812b connect the first and second surfaces. As further set forth in U.S. Pat. No. 10,751,514, the arcuate or curved shape of the first surface 1806b follows the inner surface 1807b of the guide catheter 1802b to provide smooth relative movements between the two components. The arcuate shape of the first surface 1806b can also increase or maximize axial or column strength of the push member 1804b. As a whole, the illustrated cross-sectional configuration of the push member 1804b can increase push force capability and torque control relative to flat, rectangular push members.

Figure 18I:
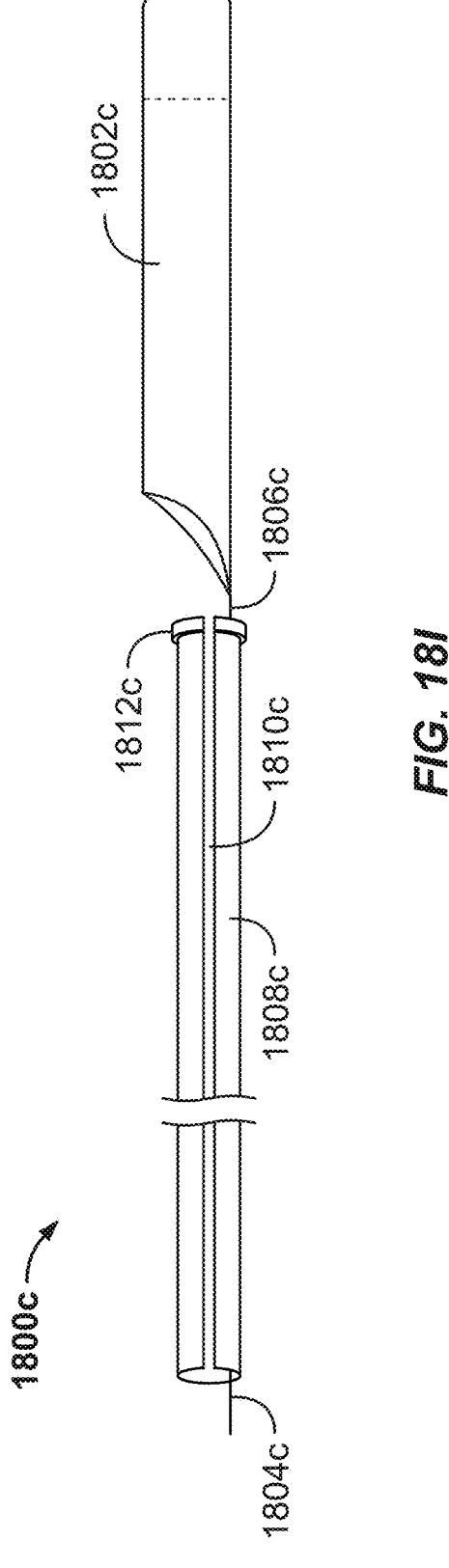
FIG. 18I illustrates a perspective view of a support catheter comprising another embodiment of a push member, as constructed in accordance with at least one embodiment.

FIG. 18I illustrates a perspective view of a support catheter 1800c having a distal tubular member 1802c coupled with a push member 1804*c* at the push member's distal end 1806*c*. Surrounding the push member 1804*c* is a removable support member 1808*c*, which may include a longitudinal slit 1810*c* extending along its length. The slit 1810*c* can be formed to be resiliently closed, such that it can be forcibly peeled open to remove the removable support member 1808*c* from the push member 1804*c*. A distal end of the removable support member may include a stop or lip member 1812*c*, which may comprise a substantially soft, elastic or otherwise depressible material configured to impact the tubular member 1802*c* without damaging it during insertion of the support catheter 1800*c* into a vessel, as further set forth in U.S. Pat. No. 10,953,197, which is incorporated by reference in its entirety herein. In some embodiments, the push member can be attached to the distal tubular member of a support catheter at least in part using adhesive bonds, thermal bonds, welds, brazes, etc. Generally, the tubular member and push member can be coupled in a manner that provides a smooth transition therebetween. The arrangement or configuration of this coupling can vary. For example, a tubular member can include an opening formed in its peripheral wall and the push member can be disposed within the opening. Inserting the push member into the opening can result in a mechanical coupling between the members and additional or alternative bonds can be utilized.

In some embodiments, the push member may change dimensions and/or properties (e.g., rigidity) in the region interfacing with the tubular member. For example, it may be desired to have the push member increase in flexibility and extend into the polymer tubular member wall as reflected, for example, by the views of FIGS. 19A and 19B. The support catheter 1900*a* shown in FIG. 19A includes a tubular member 1902*a* and a push member 1904*a*. An embedded portion 1906*a* of the push member 1904*a* is embedded within the circumferential wall of the tubular member 1902*a*, radially separated from a longitudinal slit 1908*a*. The length of the embedded portion can vary, extending less than about 5% of the length of the tubular member 1902*a*, or about any of 5%, 10%, 15%, 20%, 25%, 30%, 35%, 40%, 45%, 50%, or more, or any portion therebetween.

Figures 19A, 19B:
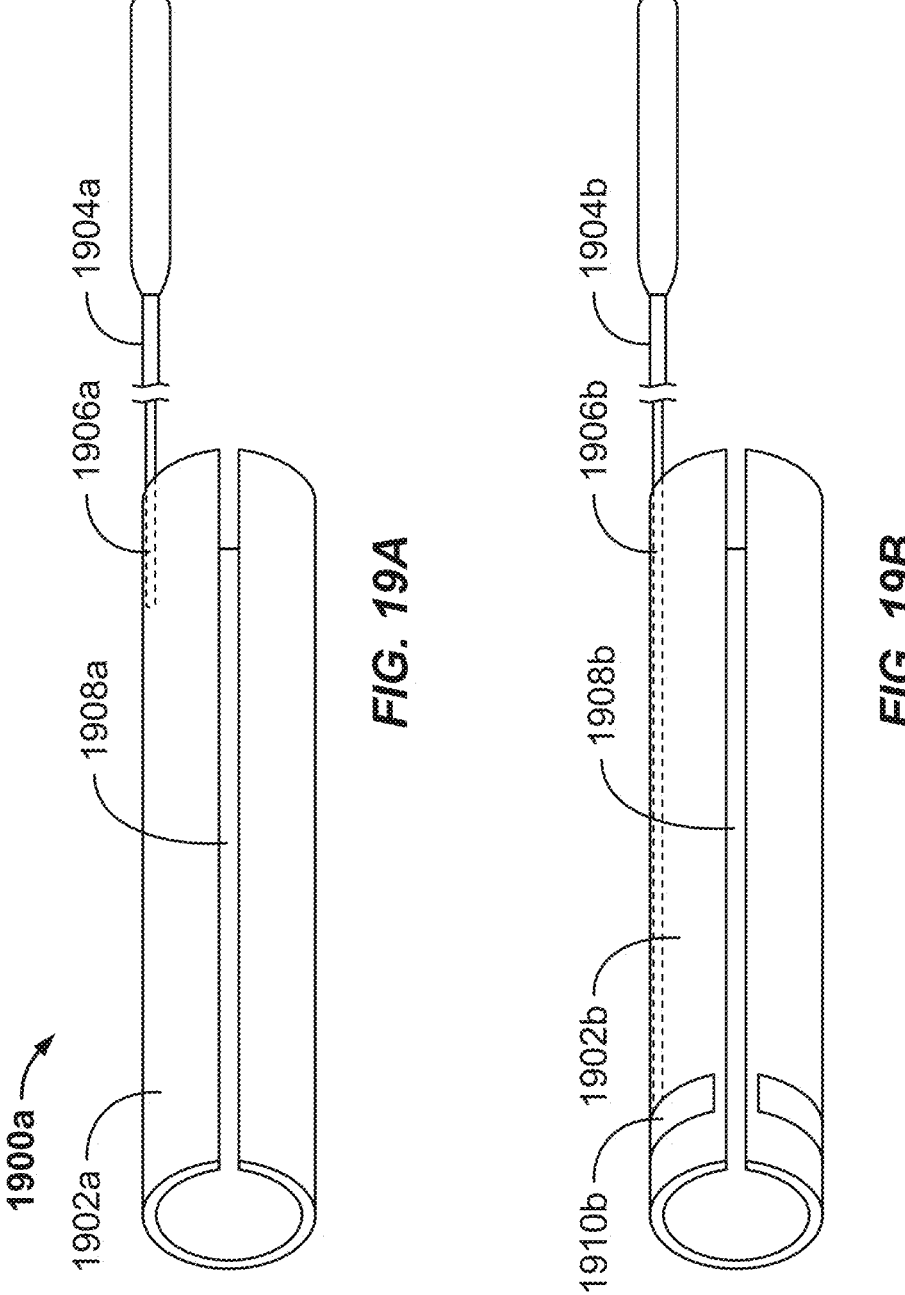
FIG. 19A illustrates a perspective view of a support catheter comprising a partially embedded push member, as constructed in accordance with at least one embodiment.
FIG. 19B illustrates a perspective view of another support catheter comprising a partially embedded push member, as constructed in accordance with at least one embodiment.

In the embodiment shown in FIG. 19B, a support catheter 1900*b* may also include a push member 1904*b* having a substantially flat portion 1906*b* radially separated from a longitudinal slit 1908*b*. The flat portion 1906*b* extends nearly the entire length of the tubular member 1902*b*, ending at a distally positioned marker band 1910*b*. The flat portion 1906*b* of the push member 1904*b* can be attached directly to the marker band 1910*b* or another metal component of the tubular member 1902*b*.

Figure 20A:
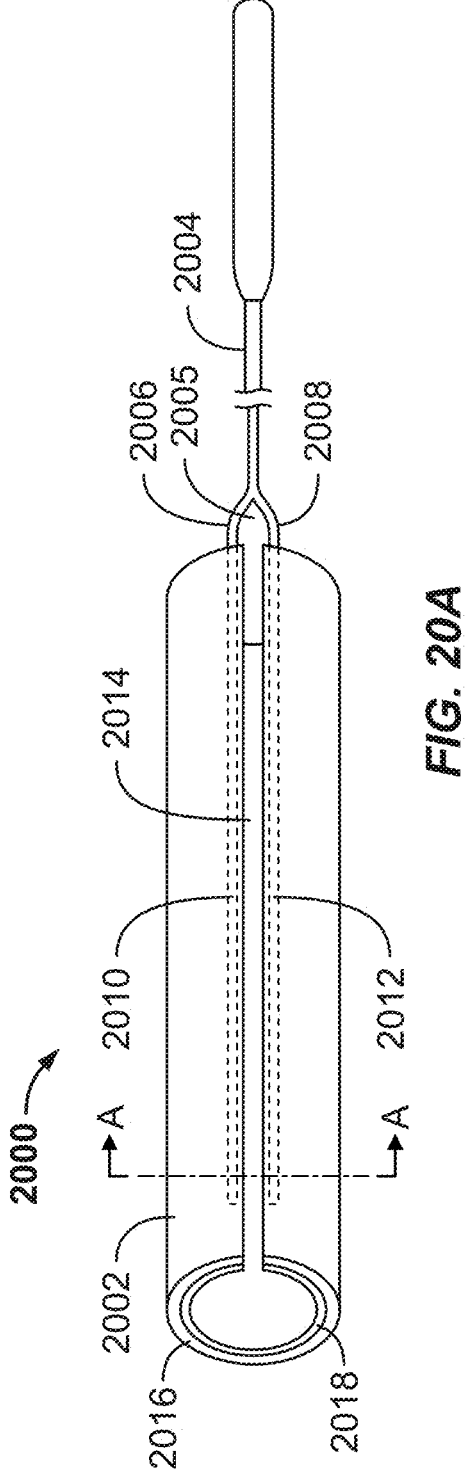
FIG. 20A illustrates a perspective view of a support catheter comprising a bifurcated push member, as constructed in accordance with at least one embodiment.
Figure 20B:
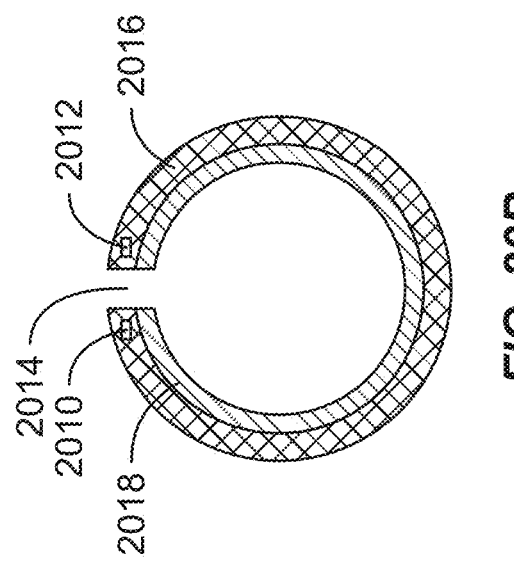
FIG. 20B illustrates an enlarged cross-sectional view of the support catheter shown in FIG. 20A, taken along line A-A.

The push member may be attached to any of the reinforcements described above that reside in the tubular member. Generally, it is desirable to have the push member attached to the distal tubular member opposite the slit, but alternatively it can be attached in a way to allow the push member to be made on the same side as the slit, or at another radial position. FIGS. 20A and 20B for example, show a perspective and transverse cross-sectional view, respectively, of a support catheter 2000 comprising a tubular member 2002 and a push member 2004. Near the proximal end of the tubular member 2002, the push member 2004 splits longitudinally, thereby forming a fork 2005 comprised of a first prong 2006 and a second prong 2008, both of which may be extended and attached or embedded within the tubular portion 2002, forming a first embedded prong 2010 and a second embedded prong 2012. Each embedded prong 2010, 2012 can support a side of the longitudinal slit 2014 defined by the tubular member 2002. As more clearly shown in the cross-sectional view of FIG. 20B, the first embedded prong 2010 can be adjacent to one side of the slit 2014, and the second embedded prong 2012 can be adjacent to the opposite side of the slit 2014, both prongs embedded within an outer polymer layer 2016 surrounding an inner liner 2018. Alternatively, or in addition, the push member 2004 may be made of separate longitudinal members that are fused, bonded, or held or secured together along the length of the push member 2004 until the push member 2004 is sufficiently close to the tubular member 2002 for the longitudinal members to separately attach to the tubular member 2002. The length of each embedded prong 2010, 2012 may vary. Generally, the integrity of the slit 2014 can be enhanced by increasing the length of the prongs 2010, 2012 within the tubular member 2002. It should be noted that the slit in this embodiment can be used to further increase the force to keep the slit closed by material memory, relying on magnetism, or by mechanical interlocking features that ensure that the slit and/or both sides of the split push member can be interlocked together. In some embodiments, one or more reinforcement structures, e.g., braids, coils, and/or marker bands, can be attached to the embedded prongs 2010, 2012. The fork 2005 can be configured to provide a radial closing force on the slit 2014 to prevent the slit from expanding when undesired. The cross-sectional shape and width of the push member 2004, including the prongs 2006, 2008, 2010, 2012, can vary. In some examples, all or at least a portion of the push member 2004 can have a flattened and/or tapered cross-sectional configuration.

Figure 21:
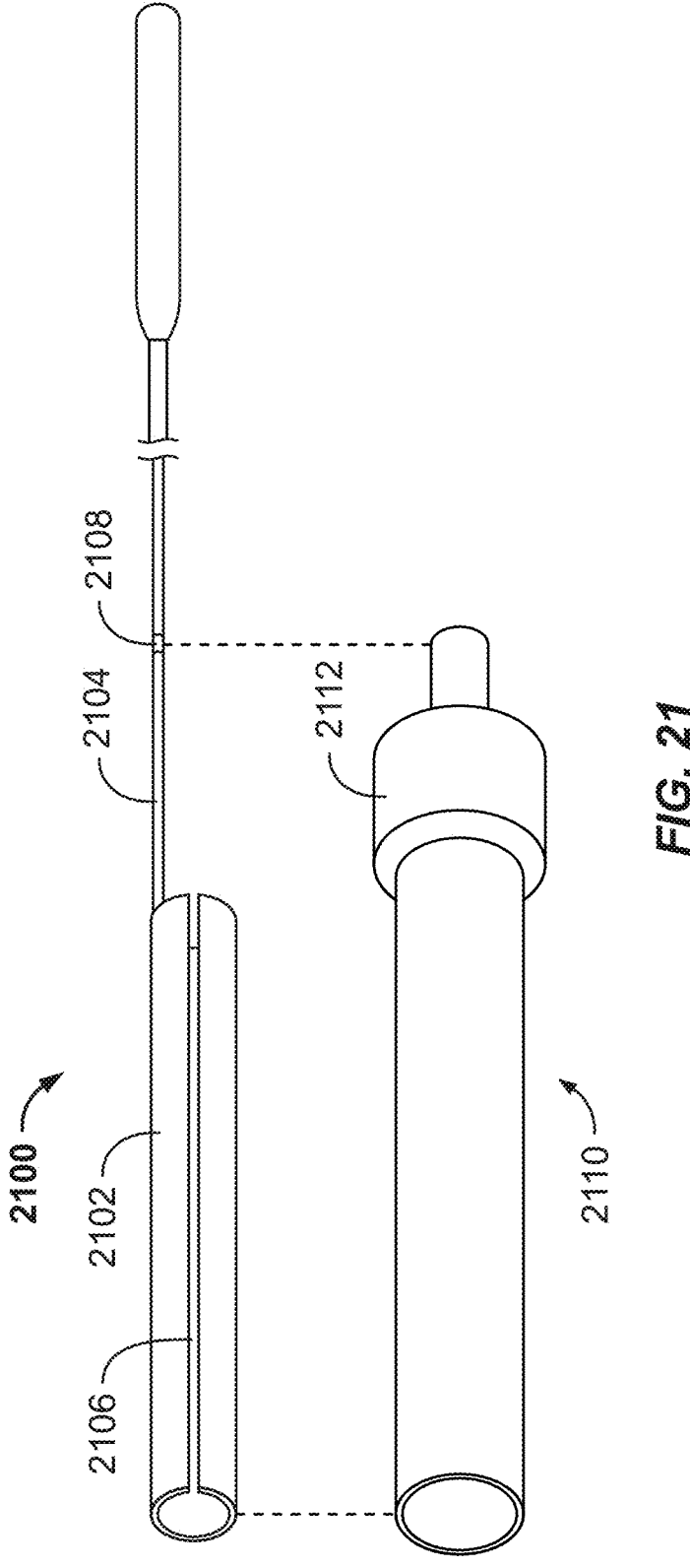
FIG. 21 illustrates a perspective view of a support catheter and compatible interventional device, as constructed in accordance with at least one embodiment.

The push member may or may not have or be attached to a handle member located on the proximal portion or end. Preferably, a handle member would have a larger diameter or other dimension than the push member alone. Optionally, the handle member can be positioned to allow at least about 110 cm of working length (length from distal tip of the tubular member to the start of the handle), in accordance, for example, with the non-limiting embodiments of FIGS. 1A and 1B. In some embodiments, the push member can have at least one marker located along its shaft that indicates to the user that once the mark is approaching the proximal end of the guide catheter, the distal tip of the support catheter is near the distal tip of the inserted guide catheter. In such embodiments, the marker may preferably be located about 100 to about 110 cm from the distal-most tip of the support catheter as reflected, for example, by FIG. 21, which shows a support catheter 2100 comprised of a distal tubular member 2102 and proximal push member 2104. The tubular member 2102 defines a longitudinal slit 2106 and the push member 2104 includes a marker 2108. An interventional device 2110 compatible with the support catheter 2100 is shown adjacent thereto. The marker 2108 of the support catheter 2100 is positioned such that when the distal tips of the support catheter 2100 and interventional device 2110 are aligned, the marker 2108 aligns approximately with the proximal end of the interventional device 2110, which may be defined by the proximal end of a luer/valve 2112.

Some aspects of the present disclosure relate to various techniques and/or tools useful for loading and unloading the disclosed support catheters onto and from various interventional devices, respectively. It will be understood that one or more combinations of the loading/unloading features described herein can be used together in some examples. In accordance with this disclosure, loading a support catheter refers to coupling the support catheter with an interventional device. Coupling may involve inserting the interventional device through the longitudinal slit of the support catheter's tubular member into the lumen defined by the tubular member. Unloading a support catheter refers to uncoupling the support catheter from an interventional device by removing the interventional device from the lumen of the support catheter's tubular member via the longitudinal slit. Advantageously, loading and/or unloading the disclosed support catheters can be achieved without first removing an interventional device from a blood vessel. The loading tools described below can facilitate the loading and unloading processes.

With respect to unloading methodologies, and as described previously, the expandable slit support catheter can be unloaded from a guidewire by first withdrawing the interventional device from a guide catheter, then withdrawing the interventional device off the guidewire, and subsequently withdrawing the expandable slit support catheter off the guidewire. Alternatively, the expandable slit support catheter and interventional device can be removed together at the same time, or the support catheter could be removed from the interventional device while the interventional device remains fully or partially positioned within the guide catheter.

Figure 22A:
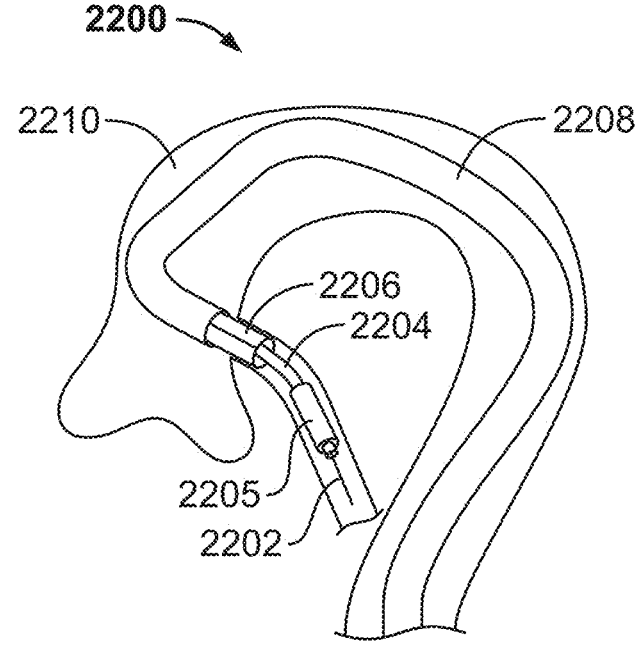
FIG. 22A illustrates a schematic snapshot of a method of using a support catheter and associated interventional devices, as constructed in accordance with at least one embodiment.
Figure 22B:
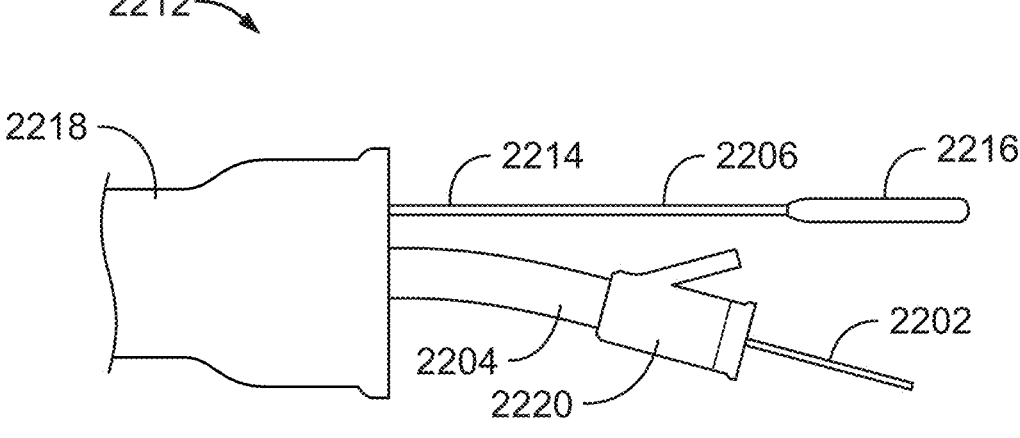
FIG. 22B illustrates a schematic snapshot of a proximal portion of the support catheter and associated interventional devices during the method shown in FIG. 22A.

One non-limiting example of an arrangement of these devices prior to implementing these techniques is reflected by the views of FIGS. 22A and 22B. FIG. 22A shows the distal end 2200 positioning of a guidewire 2202, interventional device 2204, support catheter 2206, and guide catheter/sheath 2208 within a blood vessel 2210 while performing a medical procedure. The guide catheter/sheath 2208 can surround the support catheter 2206, which can surround a portion of the interventional device 2204, which has been inserted over the guidewire 2202. FIG. 22B shows the proximal end 2212 positioning of the guidewire 2202, interventional device 2204, and support catheter 2206. The proximal end of the support catheter 2206, including a portion of the push member 2214 and the optional handle 2216, protrude from a proximal end of an access sheath 2218. A proximal end of the guidewire 2202 protrudes from a proximal end of the interventional device 2204, which may include a proximal luer or hub 2220.

Figure 23:
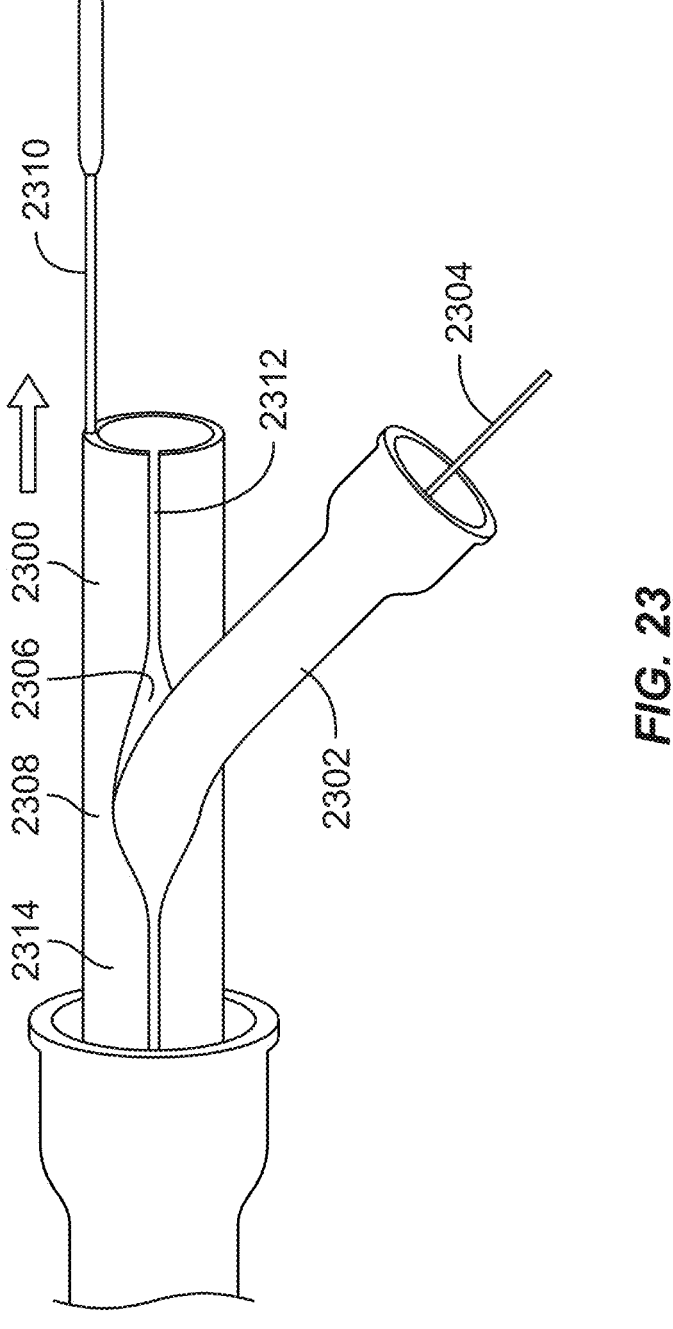
FIG. 23 illustrates a perspective view of a support catheter uncoupling from an interventional device, as constructed in accordance with at least one embodiment.

In other embodiments, the longitudinal slit of a disclosed support catheter provides the additional option of unloading the support catheter from an interventional device, e.g., a therapeutic delivery catheter shaft and/or guidewire, that is already in position in the guide catheter and/or coronary artery. Because of the large hub on the proximal end of some interventional devices, as shown in FIG. 23, the support catheter 2300 can be unloaded by peeling the support catheter 2300 off the side of the shaft of the interventional device 2302 and/or guidewire 2304 through the longitudinal slit 2306 of the support catheter 2300. This can be done by simply urging the slit 2306 open and withdrawing the support catheter 2300 from the shaft of the interventional device 2302 and/or shaft of the guidewire 2304 until the component(s) are fully removed. More specifically, it may be advantageous to remove the support catheter 2300 from the interventional device 2304 by pulling the tubular member 2308 and push member 2310 of the support catheter 2300 away from the shaft of the interventional device 2302 so that the shaft of the interventional device 2302 first exits the proximal-most portion 2312 of the slit 2306 and then continues to be removed proximally to distally, resulting in full removal when the distal-most portion 2314 of the slit 2306 is removed. This sequence can be implemented for one or more versions of the support catheters disclosed herein, including embodiments where the slit is not initially cut through the entire wall of the tubular member (e.g., FIGS. 8A-8C). In that case, by first pulling from the proximal end of the tubular member, the slit can be torn through the entire wall of the tubular member until the interventional device can be removed, and the tearing will run in the distal direction until the support catheter is fully separated.

Figure 24A:
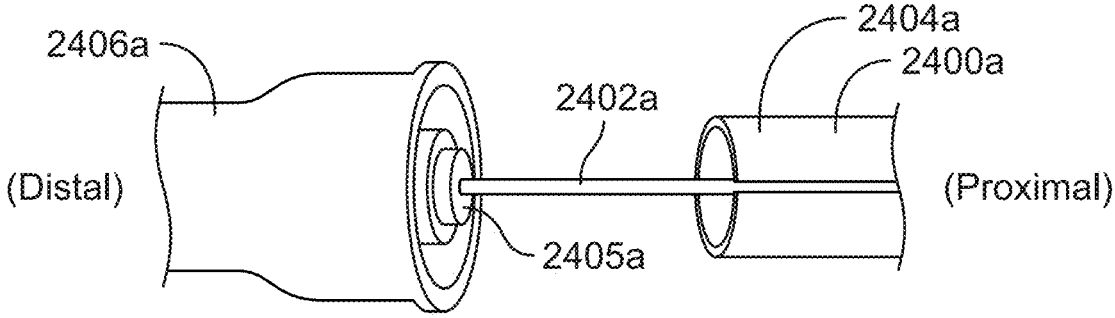
FIG. 24A illustrates a perspective view of a technique for loading a support catheter with an interventional device, as constructed in accordance with at least one embodiment.
Figure 24B:
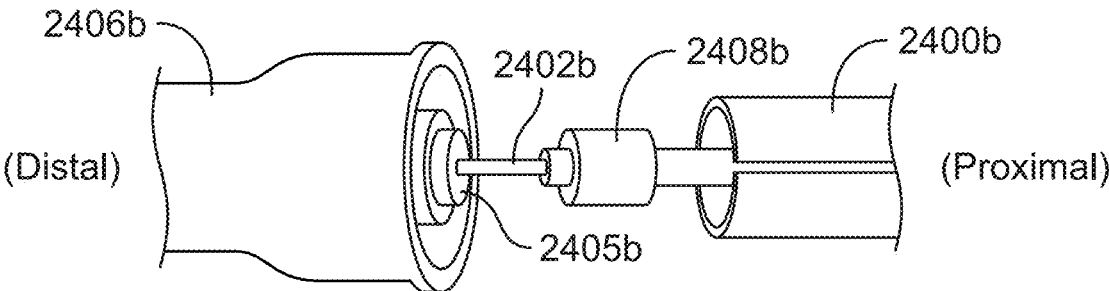
FIG. 24B illustrates a perspective view of another technique for loading a support catheter with an interventional device, as constructed in accordance with at least one embodiment.

FIGS. 24A and 24B illustrate two loading techniques that can be implemented using the disclosed devices. As shown in FIG. 24A, an expandable slit support catheter 2400a can be loaded onto a guidewire 2402a by threading the distal tubular member 2404a over the proximal end of the guidewire 2402a, advancing the tubular member 2404a through a hemostasis valve 2405a coupled to a guide catheter 2406a, and moving the support catheter 2400a distally through the guide catheter/sheath 2406a. This can be done if it is known in advance that a support catheter will be needed. Alternatively, and as shown in FIG. 24B, the distal end and/or treatment structure of an interventional device 2408b can be pre-loaded into the proximal end of the support catheter 2400b, and the assembly extended in unison over the guidewire 2402b and through the guide catheter/sheath 2406b, which may be coupled with a proximal hemostasis valve 2405b, to a target position in a blood vessel.

Figure 25A:
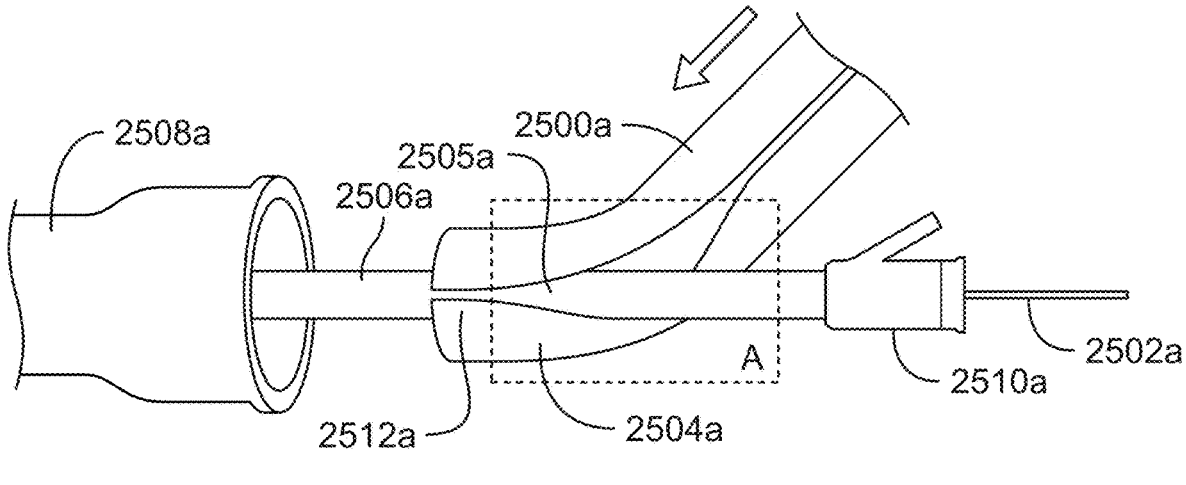
FIG. 25A illustrates a schematic view of a support catheter coupling with an interventional device, as constructed in accordance with at least one embodiment.
Figure 25B:
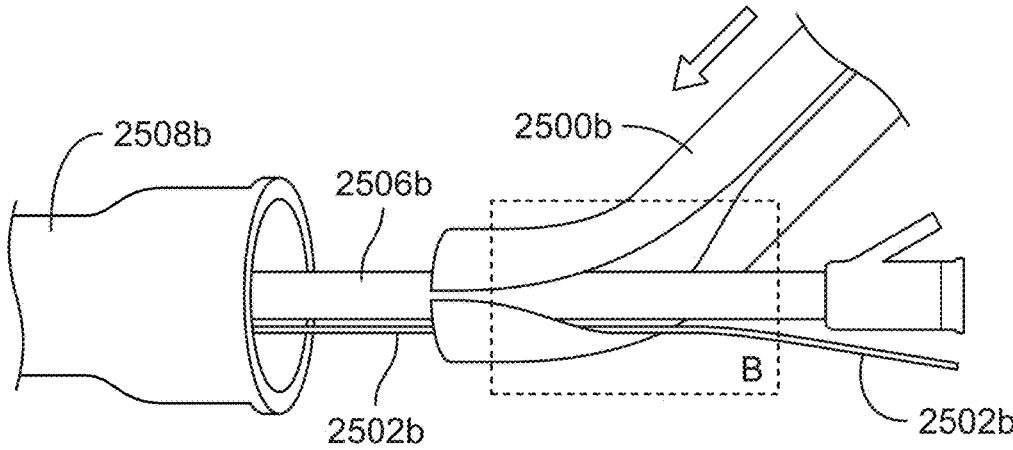
FIG. 25B illustrates a schematic view of a support catheter coupling with an interventional device, as constructed in accordance with at least one embodiment.

In other embodiments, the longitudinal slit provides the additional option of loading the expandable slit support catheter onto an interventional device, e.g., balloon/stent delivery catheter shaft and guidewire, already in position in the coronary artery as reflected, for example, by the views of FIGS. 25A and 25B. A support catheter 2500a and guidewire 2502a are shown, the support catheter 2500a having a distal tubular member 2504a and longitudinal slit 2505a expanding over an interventional device 2506a as the support catheter 2500a is pushed distally toward a guide catheter/sheath 2508a. Because of the large hub 2510a on the proximal end of the interventional 2506a, the slit expandable support catheter 2500a must be loaded onto the side of the shaft of the interventional device 2506a and/or guidewire 2502a. This can be done by simply urging open the slit 2505a and advancing the expandable slit support catheter 2500a onto the shaft of the interventional device 2506a and/or shaft of the guidewire 2502a until the components are fully within the tubular member 2504a. More specifically, it is advantageous to load the support catheter 2500a onto the interventional device 2506a by advancing the tubular member 2504a and push member proximally so that the shaft of the distal end 2512a of the support catheter 2500a is first loaded onto the interventional device 2506a and advanced, resulting in full loading when the proximal most region of the slit 2505a is loaded. Note that this loading can be performed on both over-the-wire interventional devices, where the guidewire is positioned inside the interventional device from tip to hub, or on rapid-exchange interventional devices, where the guidewire is positioned inside the distal end of the interventional device but exits and is outside on the proximal end. FIG. 25B illustrates a support catheter being loaded onto a rapid-exchange device, such as an interventional device. The support catheter 2500b is being loaded onto a guidewire 2502b via the tubular member 2504b. A distal portion of the guidewire 2502b is inserted into the rapid-exchange interventional device 2506b, which is inserted into a guide catheter/sheath 2508b.

FIGS. 25A and 25B also illustrate optional loading tool zones A, B. In some embodiments, a dedicated loading tool can be a useful adjunctive device for facilitating the loading process of a support catheter onto one or more interventional devices. Where provided, a loading tool of the present disclosure can facilitate clipping an expandable split support catheter onto the shaft of an interventional device (balloon, stent, etc.) and optionally over a guidewire (for interventional devices that are a rapid-exchange design). The loading tool is designed to make loading fast and easy and to ensure that this operation can be performed by one user. Generally, all versions of loading tool design of the present disclosure facilitate one or more of the following.

Figure 26:
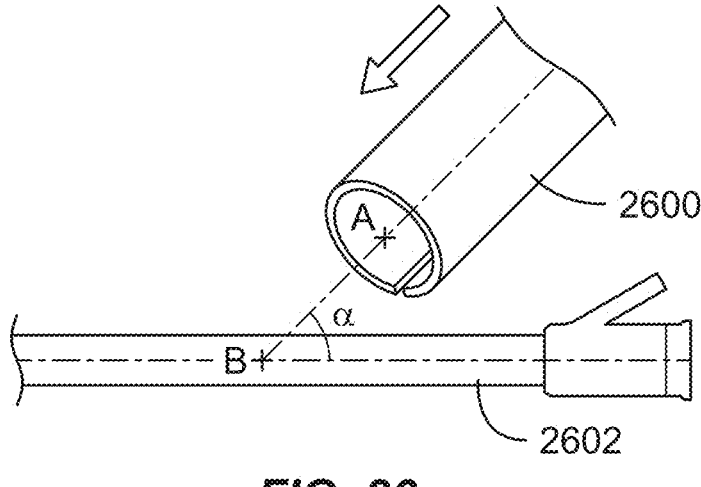
FIG. 26 illustrates an enlarged view of a distal portion of a support catheter approaching a portion of an interventional device, as constructed in accordance with at least one embodiment.

Some loading tools of the present disclosure can facilitate alignment by providing an axial or coaxial rail that introduces the lumen of an expandable split support catheter to the shaft of the interventional catheter (and optionally the shaft of the guidewire) so that all the lumens and shafts are supported and introduced in similar planes. It can be beneficial to introduce the lumen of the expandable split support catheter to the shaft of the interventional catheter so that the radial center of the lumen is in line with the radial center of the shaft. It can also be beneficial to introduce the lumen to the shaft at an angle less than 90° but greater than 0° as shown for example in FIG. 26, which illustrates a support catheter 2600 approaching an interventional device 2602 in the direction of the arrow at an angle α of less than 90°. The radial center A of the support catheter 2600 and the radial center B of the interventional device 2602 are preferably in the same plane to align the two devices and facilitate the loading process.

Figure 27:
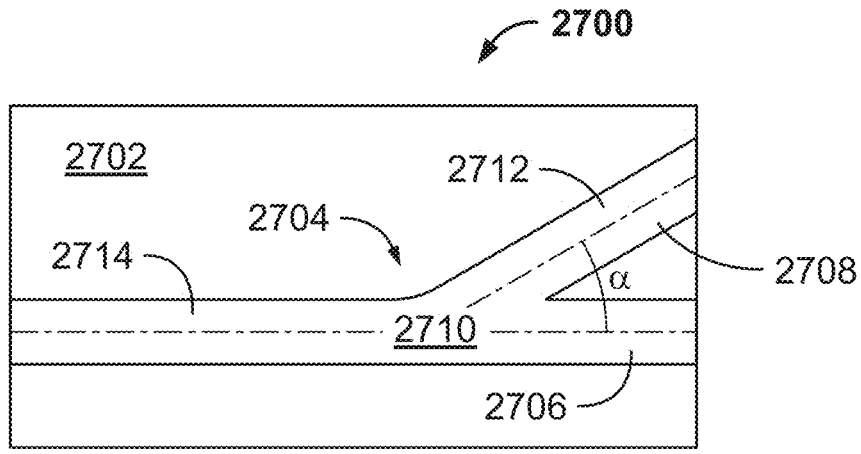
FIG. 27 illustrates a loading tool configured to facilitate coupling of a support catheter with an interventional device, as constructed in accordance with at least one embodiment.

Embodiments of the loading tools described herein can comprise several variations of an axial or coaxial rail guide. For example, a rail guide can take the form of at least one loading structure, such as a channel, rod, or trough, that provides external support and guiding to the support catheter and interventional device(s). As shown in FIG. 27, a loading tool 2700 can comprise a block or body member 2702 defining a bifurcated channel 2704 comprised of a straight delivery channel 2706 intersecting an angled loading channel 2708, the former configured to receive and guide an interventional device(s) and the latter configured to receive and guide a support catheter. The intersection 2710 of the two channels, where the support catheter is loaded onto the interventional device(s), demarcates a proximal portion 2712 of the loading channel and a distal portion 2714 of the loading channel. In some embodiments, the delivery channel 2706 intersects the midpoint of the loading channel 2708, such that length of the proximal portion 2712 of the loading channel is equal or substantially equal to the length of the distal portion 2714. The angle α defined by the proximal side of the intersection 2710 between the delivery and loading channels may vary, ranging from about 5° to about 85° or any angle therebetween, for example about 10°, 15°, 20°, 25°, 30°, 35°, 40°, 45°, 50°, 55°, 60°, 65°, 70°, 75°, or 80°.

Figures 28A, 28B, 28C, 28D, 28E, 28F:
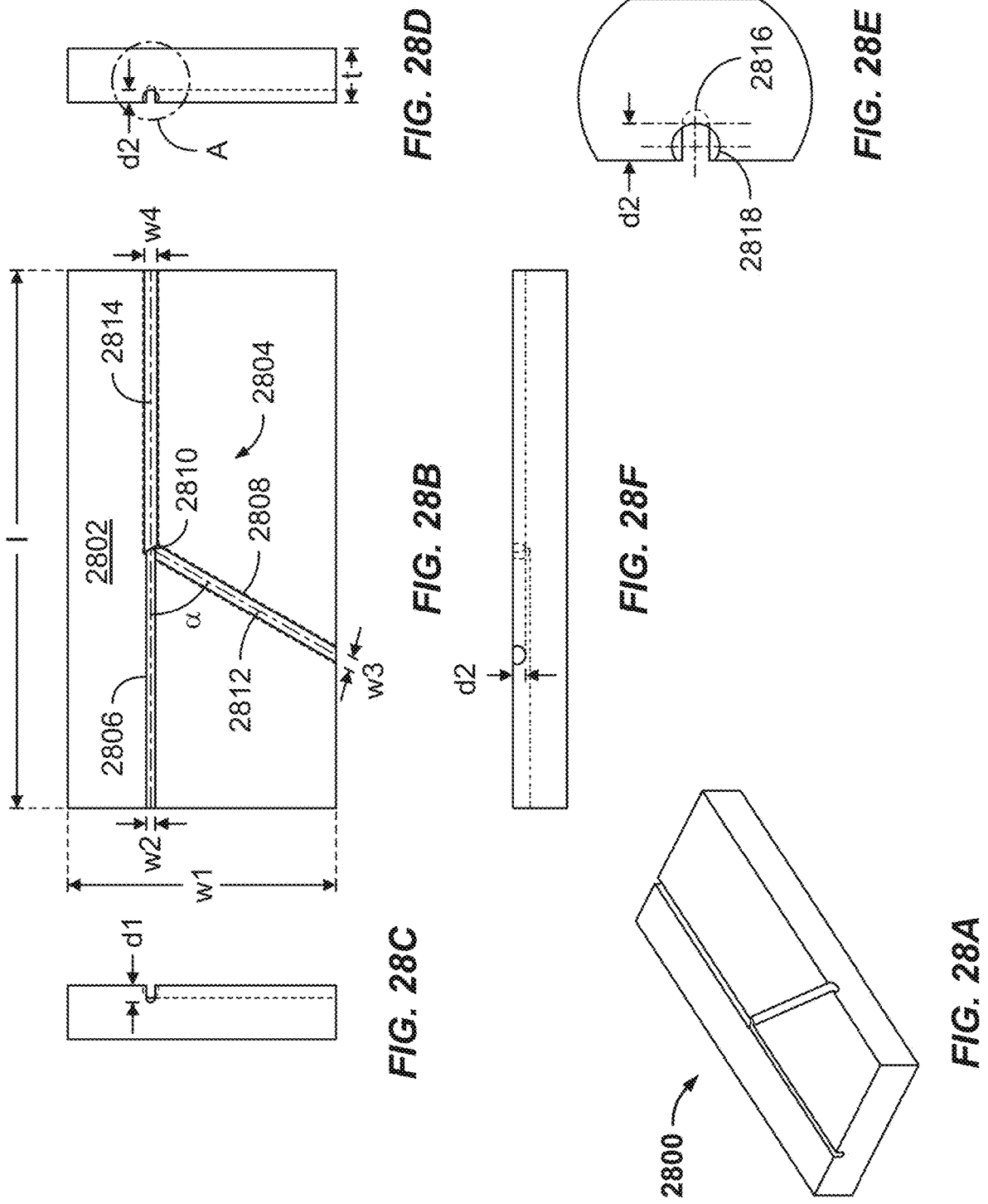
FIG. 28A illustrates a perspective view of a loading tool configured to facilitate coupling of a support catheter with an interventional device, as constructed in accordance with at least one embodiment.
FIG. 28B illustrates a plan view of the loading tool shown in FIG. 28A.
FIG. 28C illustrates a side view of the loading tool shown in FIG. 28A.
FIG. 28D illustrates another side view of the loading tool shown in FIG. 28A.
FIG. 28E illustrates an enlarged side view of the loading tool shown in FIG. 28A, taken at Detail A of FIG. 28D.
FIG. 28F illustrates a longitudinal side view of the loading tool shown in FIG. 28A.

For instance, the loading tool 2800 shown in FIGS. 28A and 28B includes a body 2802 defining a bifurcated channel 2804 comprised of a straight delivery channel 2806 and an angled loading channel 2808. The angle α defined by the intersection 2810 of the delivery channel 2806 and loading channel 2808 is about 60°, though any suitable angle may be used. The loading channel 2808 includes a proximal portion 2812 and a distal portion 2814, as defined by the location of the intersection 2810.

As further shown in FIGS. 28B and 28D, the width w1 of the body member 2802 may be about 1.25 cm, the length/ may be about 2.5 cm, and the thickness/may be about 0.25 cm. The cross-sectional width w2 of the delivery channel 2806 may be about 0.04 cm to accommodate the interventional device(s), and the width w3 of the loading channel 2808 may be about 0.07 cm to accommodate a support catheter. Because the cross-sectional width of the support catheter may be greater than the combined cross-sectional width of the other interventional devices, the width w4 of the distal portion 2814 of the loading channel 2808 may be the same or substantially the same as the proximal portion 2812, which is 0.07 cm the embodiment shown.

As illustrated in FIG. 28C, the depth d1 of the delivery channel 2806 may be about 0.07 cm, and the depth d2 of the distal portion 2814 of the loading channel 2808 may be less. In particular, the enlarged view of Detail A illustrated in FIG. 28E shows that the delivery channel 2806 defines a trench-like rail 2816 having a greater depth than the shallower, wider rail 2818 of the loading channel 2808. As further shown in FIGS. 28E and 28F, the depth d2 of the wider rail 2818 of the loading channel 2808 can be approximately 0.015 cm shallower than the trench-like rail 2816 of the delivery channel 2806. Both the delivery channel and the loading channel may have variations of an arcuate cross-sectional shape. In addition, for this and other loading tools described here, any suitable dimensions may be used.

Figures 29A, 29B, 29C, 29D:
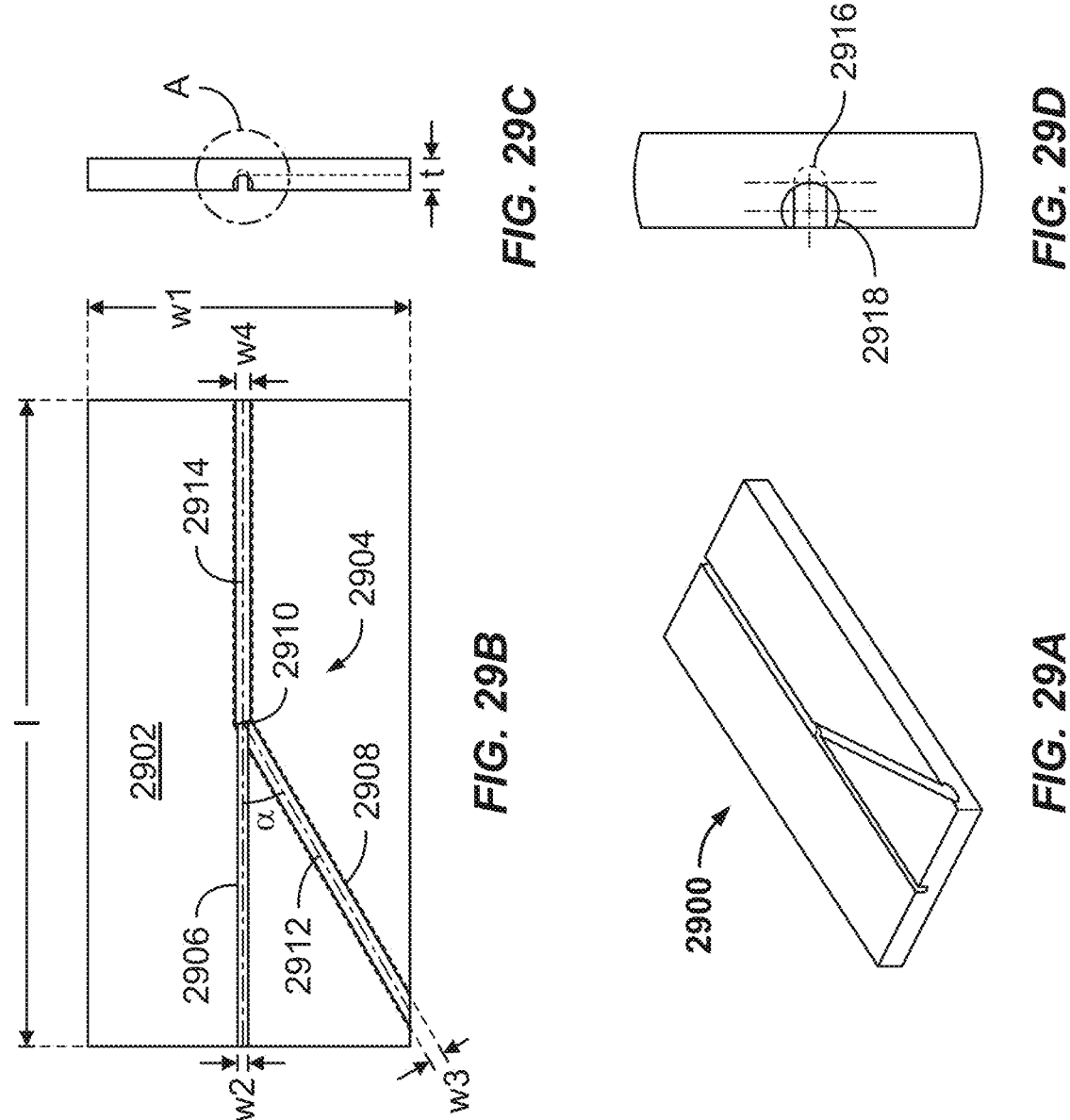
FIG. 29A illustrates a perspective view of a loading tool configured to facilitate coupling of a support catheter with an interventional device, as constructed in accordance with at least one embodiment.
FIG. 29B illustrates a plan view of the loading tool shown in FIG. 29A.
FIG. 29C illustrates a side view of the loading tool shown in FIG. 29A.
FIG. 29D illustrates an enlarged side view of the loading tool shown in FIG. 29A, taken at Detail A of FIG. 29C.

FIGS. 29A and 29B provide different views of another loading tool 2900 comprising a body 2902 defining a bifurcated channel 2904 comprised of a straight delivery channel 2906 and an angled loading channel 2908, the former configured to receive and guide the interventional device(s) and the latter configured to receive and guide the support catheter. The intersection 2910 of the two channels, where the support catheter is loaded onto the interventional device(s), demarcates a proximal portion 2912 of the loading channel and a distal portion 2914 of the loading channel. The angle α defined by the proximal side of the intersection 2910 may vary and is about 30° in this particular embodiment. In additional embodiments, the angle α may range from about 5° to about 85° or any angle therebetween, for example about any of 10°, 15°, 20°, 25°, 30°, 35°, 40°, 45°, 50°, 55°, 60°, 65°, 70°, 75°, or 80°.

As further shown in FIGS. 29B and 29C, the width w1 of the body member 2902 may be 1.25 cm, the length/may be 2.5 cm, and the thickness/of the body member 2902 may be 0.125 cm. The width w2 of the delivery channel 2906 may be about 0.04 cm to accommodate the interventional device(s), and the width w3 of the loading channel 2908 may be about 0.07 cm to accommodate the support catheter. Because the cross-sectional width of a support catheter inserted into the loading channel 2908 may be greater than the combined cross-sectional width of the other interventional devices inserted into the delivery channel 2906, the width w4 of the distal portion 2914 of the loading channel 2908 may be the same or substantially the same as the proximal portion 2912, which is 0.07 cm the embodiment shown.

As further shown in FIGS. 29C and 29D, the depth of the delivery channel 2906 may be greater than the depth of the loading channel 2908. The enlarged view of Detail A illustrated in FIG. 29D shows that the delivery channel 2906 defines a trench-like rail 2916 having a greater depth than the shallower, wider rail 2918 of the loading channel 2908. Both the delivery channel and the loading channel may have variations of an arcuate cross-sectional shape.

The length of the proximal portion 2912 of the loading channel 2908 may be about 1.287 cm, and the lengths of the delivery channel 2906 and distal portion 2914 of the loading channel may both be about 1.25 cm. The length of each channel may vary, and may depend at least in part on the angle α of the intersection 2910.

Figures 30A, 30B, 30C, 30D, 30E, 30F:
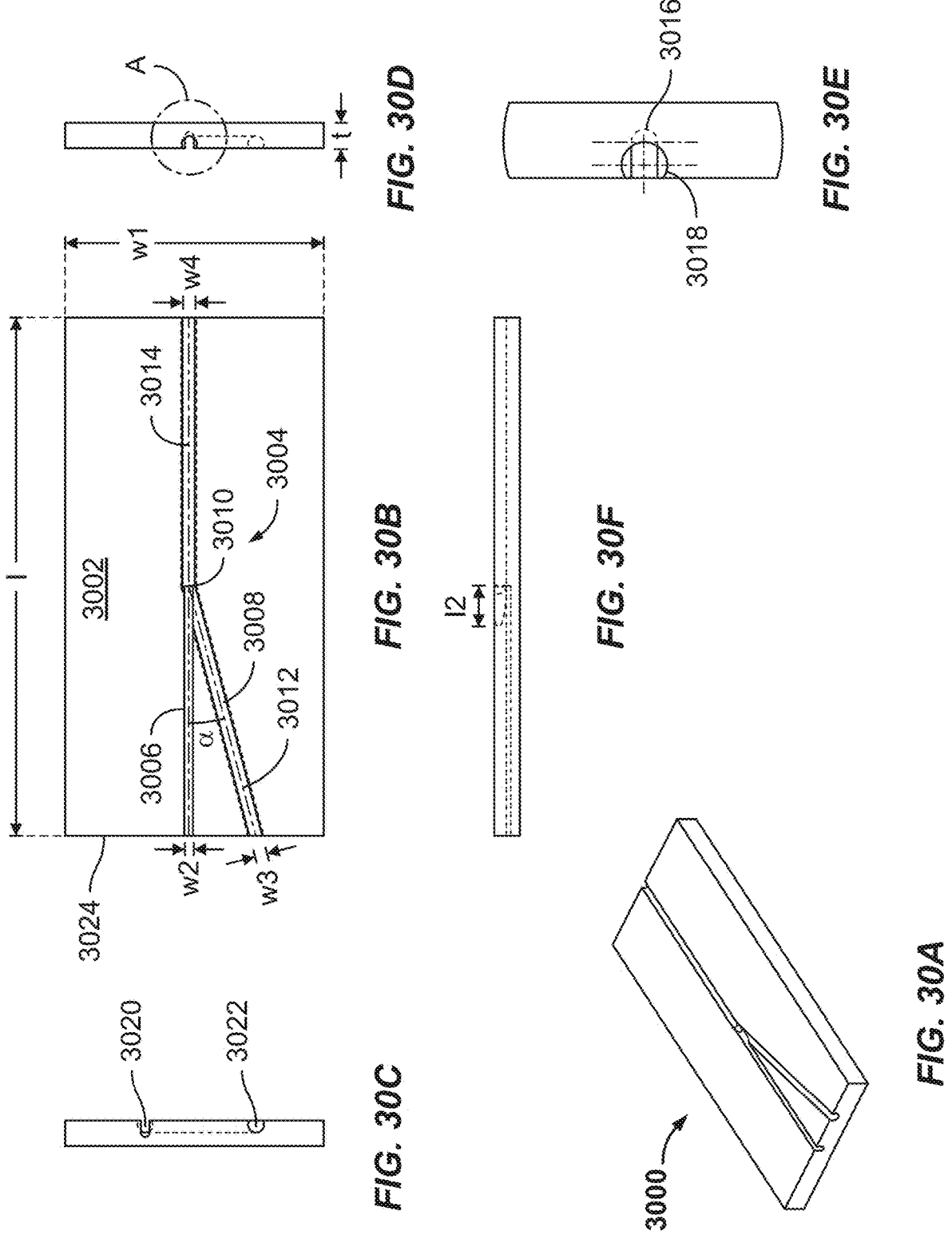
FIG. 30A illustrates a perspective view of a loading tool configured to facilitate coupling of a support catheter with an interventional device, as constructed in accordance with at least one embodiment.
FIG. 30B illustrates a plan view of the loading tool shown in FIG. 30A.
FIG. 30C illustrates a side view of the loading tool shown in FIG. 30A.
FIG. 30D illustrates another side view of the loading tool shown in FIG. 30A.
FIG. 30E illustrates an enlarged side view of the loading tool shown in FIG. 30A, taken at Detail A of FIG. 30D.
FIG. 30F illustrates a longitudinal side view of the loading tool shown in FIG. 30A.

FIGS. 30A and 30B provide different views of another loading tool 3000 comprising a body 3002 defining a bifurcated channel 3004 comprised of a straight delivery channel 3006 and an angled loading channel 3008. The intersection 3010 of the two channels demarcates a proximal portion 3012 of the loading channel and a distal portion 3014 of the loading channel. The angle α defined by the intersection 3010 of the two channel portions, as measured from the proximal side, is about 15° in this particular example. In additional embodiments, the angle α may range from about 5° to about 85° or any angle therebetween, for example about any of 10°, 15°, 20°, 25°, 30°, 35°, 40°, 45°, 50°, 55°, 60°, 65°, 70°, 75°, or 80°.

As further shown in FIGS. 30B-30D, the width w1 of the body 3002 may be about 1.25 cm, the length/may be about 2.5 cm, and the thickness/may be about 0.125 cm. The cross-sectional width w2 of the delivery channel may be about 0.045 cm to accommodate the interventional device(s), and the width w3 of the loading channel may be 0.08 cm to accommodate a support catheter. The width w4 of the distal portion 3014 of the loading channel 3008 may be the same or substantially the same as the proximal portion 3012.

Like loading tools 2800 and 2900, the delivery channel 3006 defines a narrow, trench-like rail 3016, the bottom of which has a greater depth than a shallower, wider rail 3018 of the loading channel 3008. As shown in the cross-sectional view of FIG. 30F, the depth of the rail 3016 of the delivery channel 3006 may extend about 0.01 cm below the bottom of the rail 3018 of the loading channel 3008.

The length of the proximal portion 3012 of the loading channel 3008 may be about 1.223 cm, the length of the distal portion 3014 may be about 1.319 cm, and the length of the delivery channel 3006 may be about 1.19 cm. The lengths of each channel may vary, and may depend at least in part on the angle α of the intersection 3010.

As further shown in FIG. 30C, the proximal end 3020 of the delivery channel 3006 and the proximal end 3022 of the loading channel 3008 can both be exposed on the proximal side 3024 of the body member 3002. The length l2 of the intersection 3010 is notably greater in this embodiment due to the smaller angle α between the delivery channel 3006 and proximal portion 3012 of the loading channel 3008. The greater length l2 may facilitate smooth loading and unloading between a support catheter and one or more interventional devices.

FIGS. 31A-31D provide views of another loading tool 3100 comprising a body member 3102 defining a bifurcated channel 3104, this time comprised of a curved delivery channel 3104, this time comprised of a curved delivery channel 3106 and a curved loading channel 3108. The intersection 3110 of the two channels, where the support catheter is loaded onto the interventional device(s), demarcates a proximal portion 3112 of the loading channel 3108 and a distal portion 3114 of the loading channel. In some embodiments, a proximal portion 3116 of the loading channel 3108 may be straight or substantially straight as can a distal portion 3118 of the loading channel.

Figures 31A, 31B, 31C, 31D:
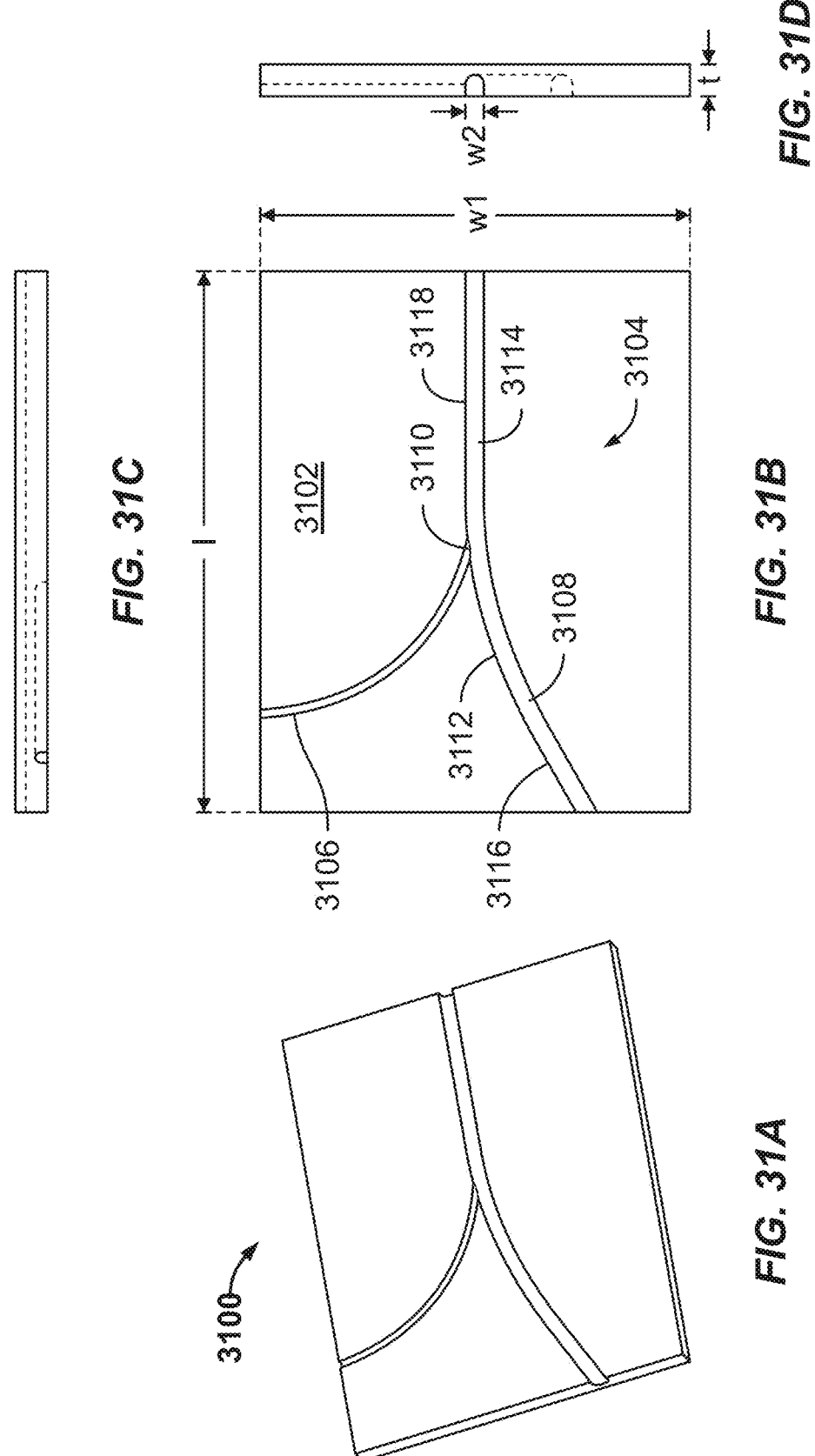
FIG. 31A illustrates a perspective view of a loading tool configured to facilitate coupling of a support catheter with an interventional device, as constructed in accordance with at least one embodiment.
FIG. 31B illustrates a plan view of the loading tool shown in FIG. 31A.
FIG. 31C illustrates a longitudinal side view of the loading tool shown in FIG. 31A.
FIG. 31D illustrates another side view of the loading tool shown in FIG. 31A.

As further shown in FIGS. 31B-31D, the width w1 of the body member 3102 may be about 2.0 cm, the length l may be about 2.5 cm, and the thickness t may be about 0.125 cm. The cross-sectional width w2 of the distal portion of the loading channel 3114 may be the same or substantially the same as that of the proximal portion 3112, which is 0.08 cm in the embodiment shown.

FIGS. 32A-32C provide views of another loading tool 3200 comprising a body 3202 defining a bifurcated channel 3204 comprised of a curved delivery channel 3206 and a curved loading channel 3208. The intersection 3210 of the two channels defines a proximal portion 3212 of the loading channel 3208 and a distal portion 3214 of the loading channel. In some embodiments, a proximal portion 3216 of the loading channel 3208 may be straight or substantially straight as can a distal portion 3218 of the loading channel.

As further shown in FIGS. 32A-32C, the proximal portion 3212 of the loading channel 3208 may comprise an internal lip or rail 3220 protruding into the lumen of the channel 3208, where it can maintain the longitudinal slit 3222 of a support catheter 3224 in an open configuration as the support catheter 3224 slides along the rail, ready to receive an interventional device at the intersection 3210. The cross-sectional width of the distal portion 3214 may taper in the distal direction. In some embodiments, tapering may occur over an approximately 1-inch stretch. Such an internal lip or rail 3220 also may be used on any loading tool, as described herein.

FIGS. 33A-33D provide views of another loading tool 3300 comprising a body member 3302 defining a bifurcated channel 3304 comprised of a curved delivery channel 3306 and a curved loading channel 3308. The intersection 3310 of the two channels defines a proximal portion 3312 of the loading channel 3308 and a distal portion 3314 of the loading channel. In some embodiments, a proximal portion 3316 of the loading channel 3308 may be straight or substantially straight, as can a distal portion 3318 of the loading channel. Any desired curvature, angles, straightness, or combinations of these may be used.

Figures 33A, 33B, 33C:
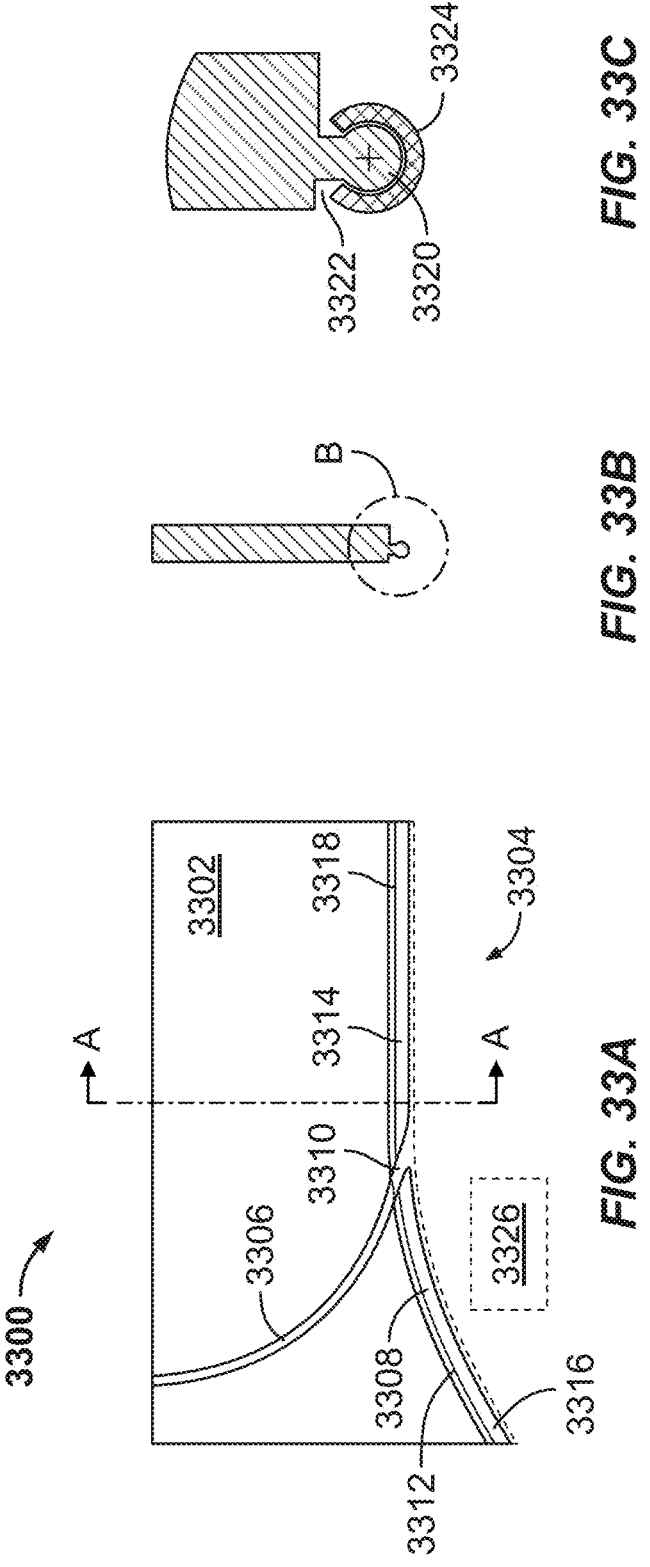
FIG. 33A illustrates a plan view of a loading tool configured to facilitate coupling of a support catheter with an interventional device, as constructed in accordance with at least one embodiment.
FIG. 33B illustrates a cross-sectional view of the loading tool shown in FIG. 33A, taken along line A-A.
FIG. 33C illustrates an enlarged cross-sectional view of the loading tool shown in FIG. 33B, taken at Detail B.

As further shown in FIGS. 33A-33C, the proximal portion 3312 of the loading channel 3308 may comprise a rail 3320 comprising a lip, which may be an internal ball-shaped lip or other suitable structure, extending into the lumen of the channel. The longitudinal slit 3322 of a support catheter 3324 may slide along the rail 3320, thereby maintaining the slit 3322 in an expanded position configured to readily receive one or more interventional devices upon contacting such devices at the intersection 3310. The rail 3320 may taper along the distal portion 3314 of the loading channel 3308 until it no longer protrudes from the inner wall of the channel. In some embodiments, full tapering may occur over an approximately 1-inch stretch of the distal portion 3314 of the loading channel. Because the rail 3320 fits within the support catheter, the maximum outer diameter of the rail 3320 is at least slightly smaller than the inner diameter of the support catheter. In some examples, the outer diameter of the rail 3320 can be about 0.05 inches. Inclusion of the protruding rail 3320 may eliminate the need for the quadrant 3326 of the body member, as included in the aforementioned loading tools.

The cross-sectional diameter of the channels may be roughly the same as or slightly greater than the outside diameter dimensions of the expandable split support catheter and interventional device (optionally including a guidewire and wire-bundling feature). Similarly, an internal support feature may have an outer diameter similar to or greater than the inner diameter of the split support catheter lumen (or greater, to facilitate opening of the slit). It may also be desirable to have a loading structure, e.g., an elongate shaft or rod, taper and/or have an elongate, wedge-shaped protrusion (other shapes may also be used) so that a support catheter can be easily loaded onto the loading structure, after which the longitudinal slit can be expanded as the slit tubular member nears the shaft of the interventional device, as reflected, for example, by FIG. 34.

Figures 34, 35:
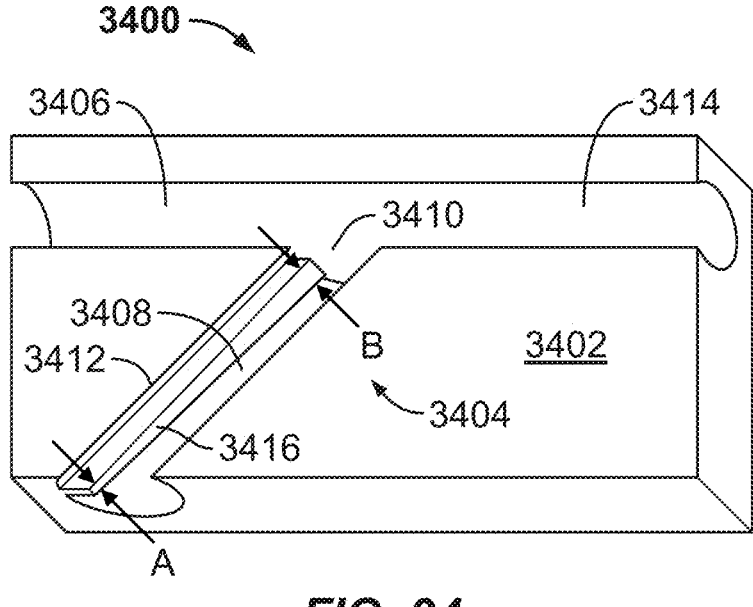
FIG. 34 illustrates a perspective view of another loading tool configured to facilitate coupling of a support catheter with an interventional device, as constructed in accordance with at least one embodiment.
FIG. 35 illustrates a perspective view of another loading tool configured to facilitate coupling of a support catheter with an interventional device, as constructed in accordance with at least one embodiment.

FIG. 34 shows a loading tool 3400 comprising a body member 3402 that defines a bifurcated channel 3404 again featuring a delivery channel 3406 and a loading channel 3408 connecting at an intersection 3410, which demarcates a proximal portion 3412 of the loading channel 3408 and a distal portion 3414 of the loading channel. The proximal portion 3412 of the loading channel defines an inner protrusion or wedge 3416 that is thinner at point A than at point B. In operation, the longitudinal slit of a support catheter expands open as it is advanced toward point B along the inner wedge 3416 so that the slit opens to an equal or greater diameter than the shaft of an associated interventional device being inserted through the delivery channel 3406.

FIG. 35 shows a loading tool 3500 comprising a body member 3502 that defines a bifurcated channel 3504 again featuring a delivery channel 3506 and a loading channel 3508 connecting at an intersection 3510, which demarcates a proximal portion 3512 of the loading channel 3508 and a distal portion 3514 of the loading channel. As shown, the cross-sectional diameter of the distal portion 3514 of the loading channel 3508 tapers down in the distal direction to close the longitudinal slit of a support catheter around an interventional device and tighten the coupling of the two components as they are extended through the distal portion 3514 of the loading channel.

Figure 36:
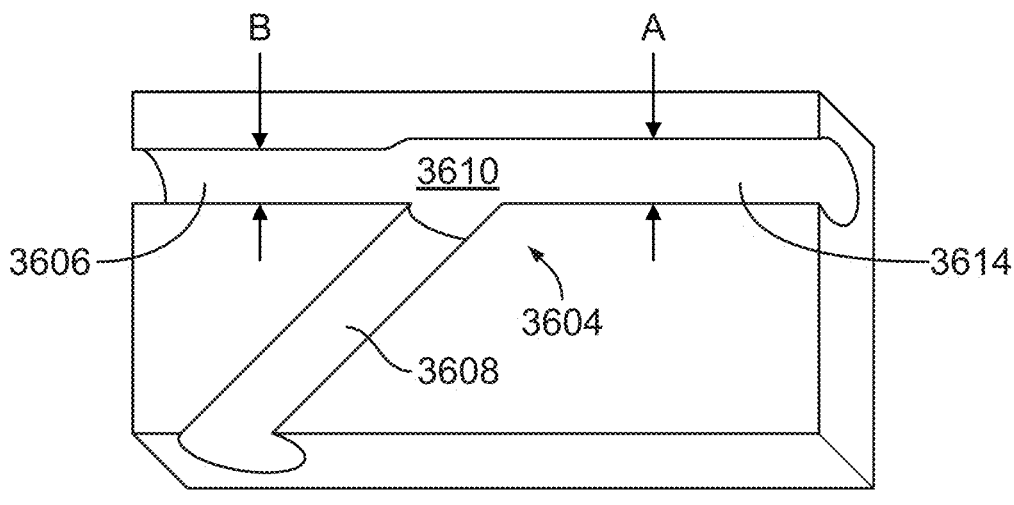
FIG. 36 illustrates a perspective view of a portion of a loading tool configured to facilitate coupling of a support catheter with an interventional device, as constructed in accordance with at least one embodiment.

In an embodiment, the trough or channel of a loading tool may be larger at the intersection between the loading channel and the delivery channel, which may provide room for the support catheter to wrap around the interventional device in an unobstructed way as reflected, for example, by FIG. 36. The depicted channels of a loading tool include a bifurcated channel 3604 having a delivery channel 3606 and a loading channel 3608 meeting at intersection 3610. As shown, the diameter of the delivery channel 3606 at point B is smaller than the diameter of the distal portion 3614 of the loading channel 3608 at point A.

Figure 37:
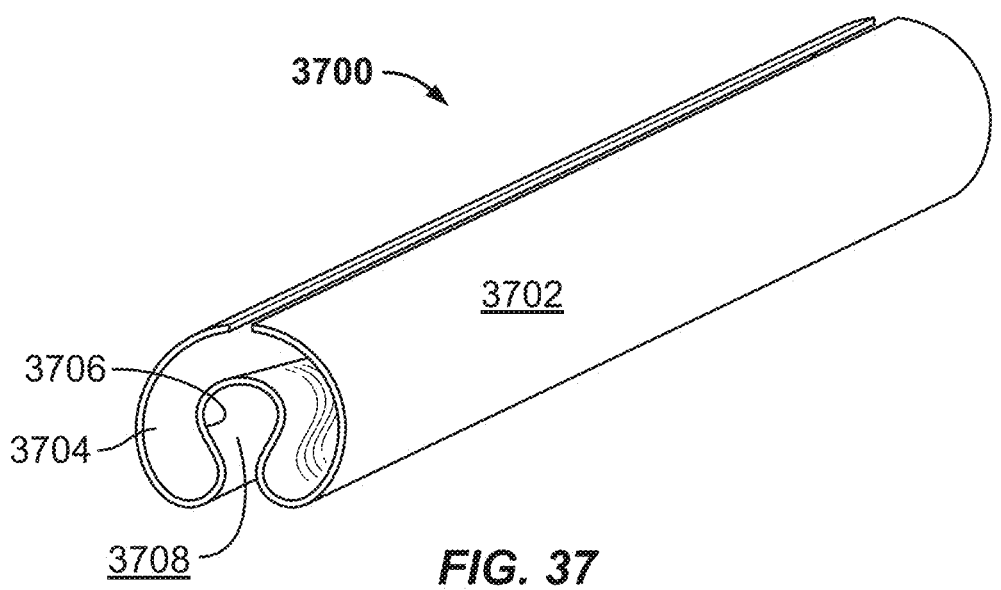
FIG. 37 illustrates a perspective view of another loading tool configured to facilitate coupling of a support catheter with an interventional device, as constructed in accordance with at least one embodiment.

FIG. 37 is a perspective view of another loading tool 3700, this time featuring an elongate body 3702 or rod defining a longitudinal gap 3704 configured to receive a support catheter. The body 3702 includes an arcuate wall 3706 defining a receiving space 3708 configured to receive one or more interventional devices. Unidirectional extension of a support catheter and interventional device along the length of the body 3702 facilitates coupling of the two components as the two components are extended beyond an end of the body 3702 toward a treatment site. This configuration can also facilitate detachment of the loading tool from a guide extension wire shaft.

Figure 38A:
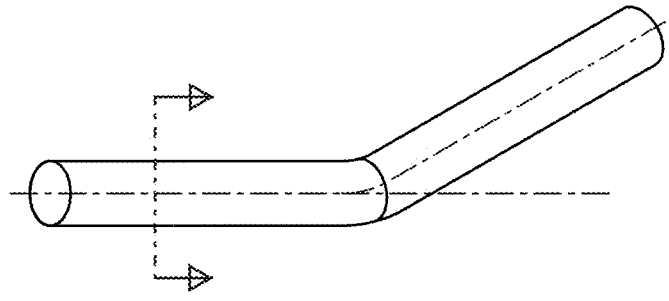
FIG. 38A illustrates a loading tool configured to facilitate coupling of a support catheter with an interventional device, as constructed in accordance with at least one embodiment.
Figure 38B:
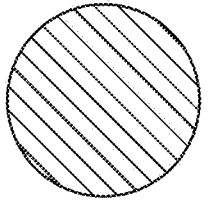
FIG. 38B illustrates a cross-sectional view of a portion of the loading tool shown in FIG. 38A.
Figure 38C:
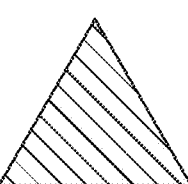
FIG. 38C illustrates a cross-sectional view of a portion of an alternate version of the loading tool shown in FIG. 38A.
Figure 38D:
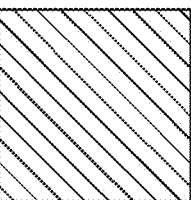
FIG. 38D illustrates a cross-sectional view of a portion of an alternate version of the loading tool shown in FIG. 38A.
Figure 38E:
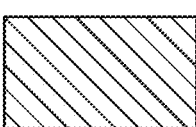
FIG. 38E illustrates a cross-sectional view of a portion of an alternate version of the loading tool shown in FIG. 38A.
Figure 38F:
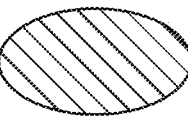
FIG. 38F illustrates a cross-sectional view of a portion of an alternate version of the loading tool shown in FIG. 38A.
Figure 38G:
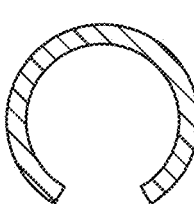
FIG. 38G illustrates a cross-sectional view of a portion of an alternate version of the loading tool shown in FIG. 38A.

An axial or coaxial rail guide can also take the form of a shaft or rod that provides internal support and guiding as reflected by the view, for example, of FIG. 38A. The shaft or rod cross-section can be circular, as shown, but can also be non-circular (e.g., triangular wedge-shaped, square, rectangular, oval, C-shaped or any desired regular or irregular configuration or the like, or combinations of these, as reflected by FIG. 38B-38G). A combination of cross-sectional shapes can be included in a single loading device. The cross-sectional shapes can also change along the length of a channel or rod of a loading tool.

Figure 39:
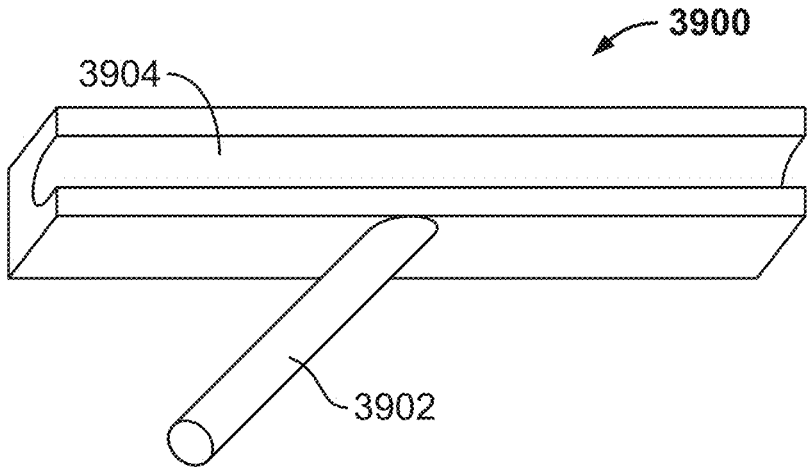
FIG. 39 illustrates a loading tool comprising a trough and a rod configured to facilitate coupling of a support catheter with an interventional device, as constructed in accordance with at least one embodiment.

The loading tools of the present may have a combination of loading structures. Embodiments can include at least one elongate rod, channel, and/or trough configured to receive and accommodate axial or coaxial sliding of a tubular member of a support catheter. In addition, the loading tool embodiments can include a combination of features, e.g., channels, troughs, rods, wedges, elongate protrusions, rails, or inner shafts/rods, configured specifically to open the longitudinal slit of a support catheter, for example as shown in FIG. 39, which depicts a loading tool 3900 having a combination of internal and external support and guiding, e.g., a rod and a trough. The loading tool 3900 includes a loading rod 3902 attached to a delivery channel or trough 3904. The delivery trough 3904 is configured to receive and guide one or more interventional devices and the loading rod 3902 is configured to receive and guide a support catheter. The delivery trough 3904 and loading rod 3902 can be sized to receive and accommodate axial or coaxial sliding of an interventional device and support catheter, respectively. In some embodiments, it may be beneficial to provide the loading tool 3900 as a multi-component, unassembled device. For example, it may be beneficial to have an internal rod insertable into the distal end of the support catheter until its longitudinal slit flares open, and then have this assembly fit into a body member or block defining one or more delivery troughs.

Figure 40:
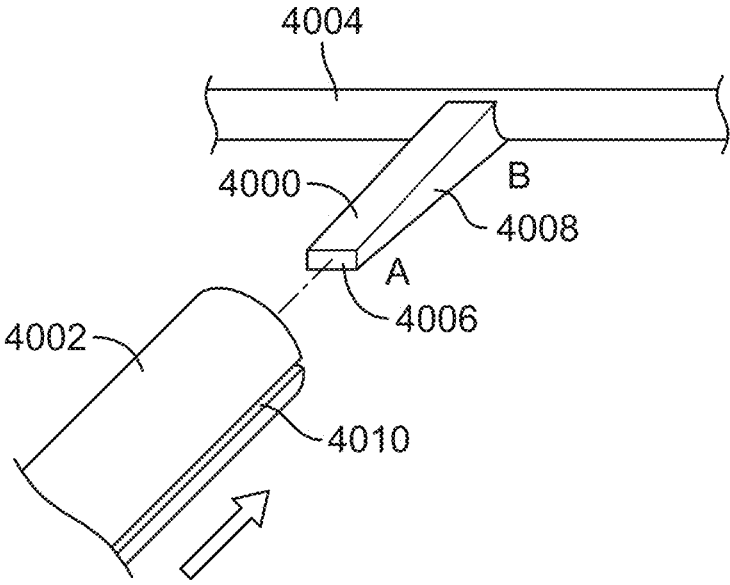
FIG. 40 illustrates a support catheter approaching a loading tool comprising a rod, as constructed in accordance with at least one embodiment.

Another optional feature provided by some of the loading tools of the present disclosure is a feature to open the slit of the support catheter. It is possible to add features to the tool so that the slit is opened up so that it can easily slip onto the shaft of the interventional device (e.g., balloon, stent, plus the guidewire and optional wire bundling feature (described below)). An example of this is a wedge that is designed into the trough of the axial or coaxial rail so that when the slit interacts with the wedge, it is expanded wider so that it can slide onto the shaft of the interventional device (e.g., balloon, stent, plus the guidewire and option wire bundling feature (described below)). Similarly, an internal support feature may have an outer diameter shaft or rod sized similar to the inner diameter of the split support catheter lumen or greater to facilitate opening of the slit. It may also be desirable to have the shaft or rod tapered so that it can be easily loaded and then start to expand the slit. The loading tool shown in FIG. 40, for example, comprises a loading rod 4000 having a proximal end 4006 and a distal end 4008. The proximal end 4006 has a smaller cross-sectional diameter than the distal end 4008. As a support catheter 4002 is advanced distally down the rod 4000, the longitudinal slit 4010 expands until intersecting with an interventional device 4004. The tip of the wedge could start small (similar to the width of the slit feature) and the largest portion of the wedge can be equivalent or larger that the diameter of the interventional device (optionally including a guidewire and option wire bundling feature (described below)).

In some embodiments, because the loading tool is designed to allow for one single operator to use it, it can be beneficial to have features to free up hands and provide stability during loading. For example, the loading tools of the present disclosure can have a flat base for stability. Some of the block style are designed to sit flat on a table and be of sufficient length, width, and thickness to ensure stability, for example as in FIGS. 34, 35, and 39.

Figure 41:
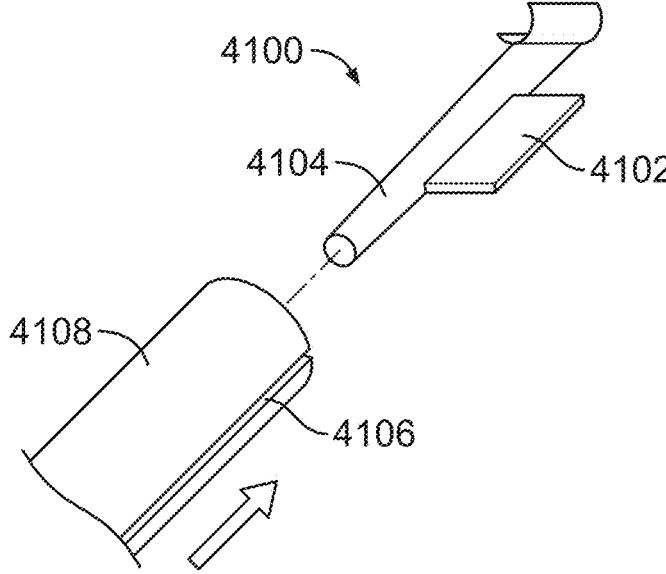
FIG. 41 illustrates a support catheter approaching a loading tool comprising a rod and a handle, as constructed in accordance with at least one embodiment.

In some embodiments, the tools of the present disclosure can incorporate handles or other grasping features so that the user can stabilize the tool with one hand while using the other to advance the support catheter. This can be particularly useful with designs that rely on an inner rail to track the slit tubular member over. For this design it may be useful to have a member protrude from a region where the slit is opened so that the tool can be grasped. FIG. 41 provides an example where the loading tool 4100 includes a handle 4102 protruding from the side of a loading rod 4104. The handle 4102 can be substantially flat or wedge-shaped, or any other desired shape, and can pass through the longitudinal slit 4106 defined by a tubular member 4108 of a support catheter as the tubular member 4108 is inserted onto the rod 4104, provided the slit 4106 and handle 4102 are on the same plane.

Figure 42:
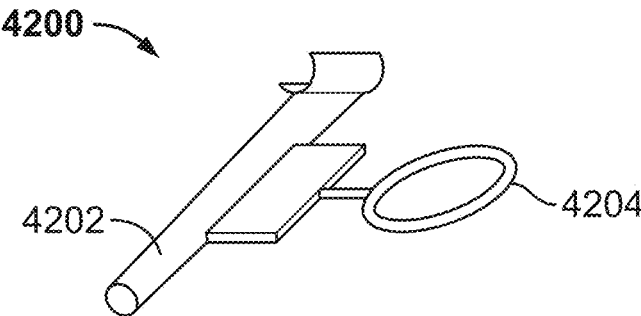

A loading tool can also be configured for mounting on a user's finger using a ring-like device attached to the tool. For example, FIG. 42 shows a loading tool 4200 comprising an elongate rod 4202 and a ring feature 4204 protruding therefrom.

Figure 43:
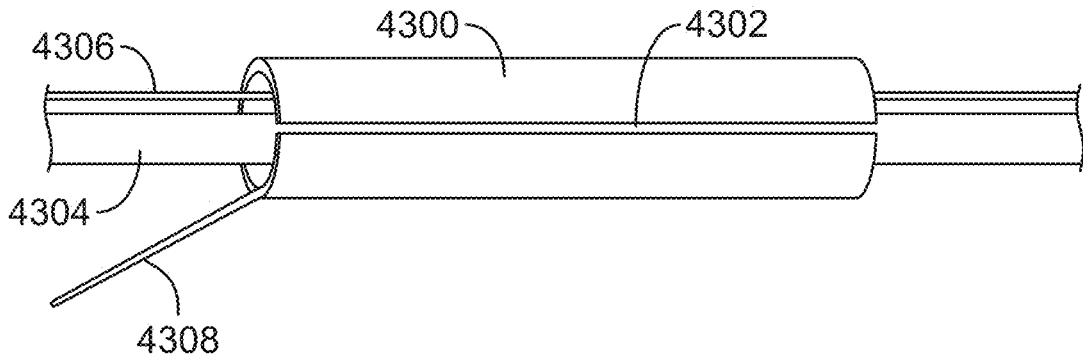

As previously described, there are instances when the expandable split support catheter is loaded over both a balloon shaft and a wire. Interventional procedures may also involve concurrent employment of two or more rapid-exchange devices. For these applications, a separate, temporary split-tube may bundle the balloon shaft and wire together, so that the split support catheter can be loaded over the bundle before removing and optionally discarding the temporary tube as reflected, for example, by FIG. 43, which shows a temporary bundling sleeve 4300 comprising a longitudinal slit 4302. The bundling sleeve 4300 can be loaded over an interventional device 4304 and guidewire 4306, and may further include a handle 4308 to facilitate its removal.

Figure 44:
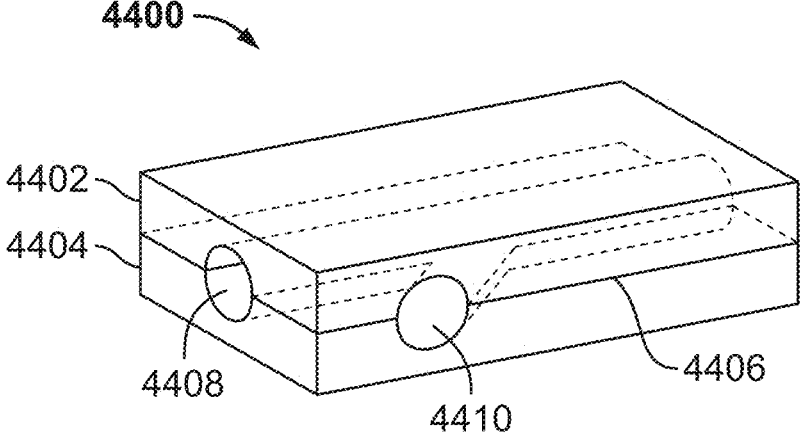
Figure 45:
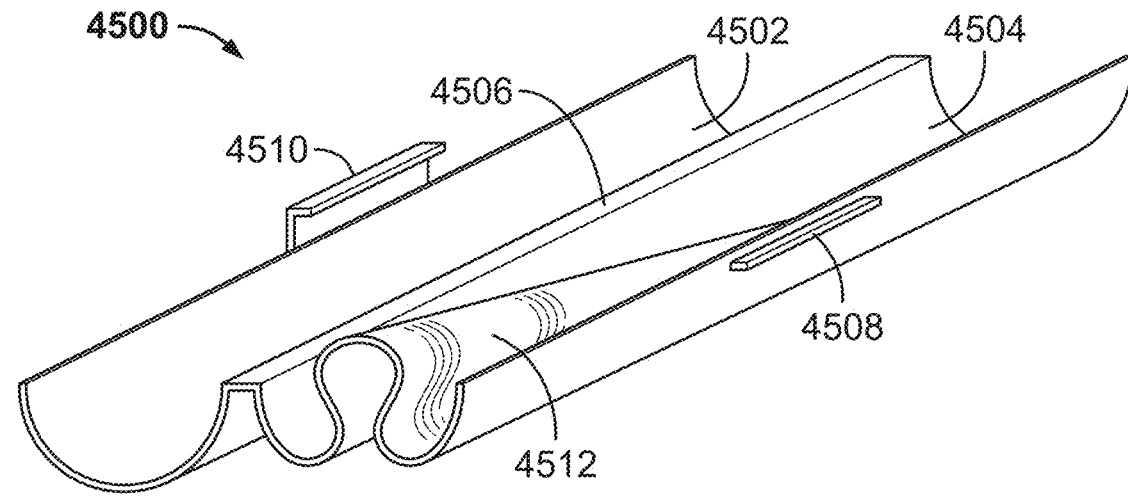

Optionally, a bundling device may have a clam-shell design as shown, for example, in FIGS. 44 and 45. The bundling device 4400 of FIG. 44 includes a first lid 4402, a second lid 4404, and an interface 4406 therebetween. When sandwiched together or otherwise closed, the first and second portions 4402, 4404 form an internal delivery tube 4408 and an intersecting loading tube 4410 for receipt of an interventional device and support catheter, respectively.

The bundling device 4500 shown in FIG. 45 has a "clam-shell" configuration featuring a first lid 4502 and a second lid 4504 connected at a longitudinal hinge 4506. The bundling device 4500 also includes a locking mechanism comprised of a lip 4508 configured to engage a corresponding overhang feature 4510 upon folding the first portion 4502 and second portion 4504 together via the hinge 4506. The particular locking mechanism may vary and may include, for example, a snap-fit, clamping or lock-and-key mechanism.

As further shown in FIG. 45, the bundling device 4500 can include an interior sloping surface 4512 configured to expand the longitudinal slit of a support catheter as the catheter approaches an interventional device. Viewing the exterior of the device, the sloping feature 4512 may resemble a valley of variable width extending into the interior of the device 4500. The configuration of the bundling device 4500 may facilitate removal of the device from a wire shaft and from a production standpoint, it may be easier to manufacture, for example via injection molding. An optional cover or clam-shell style lid may also be used to help ensure that the devices stay within the troughs.

Figure 46:
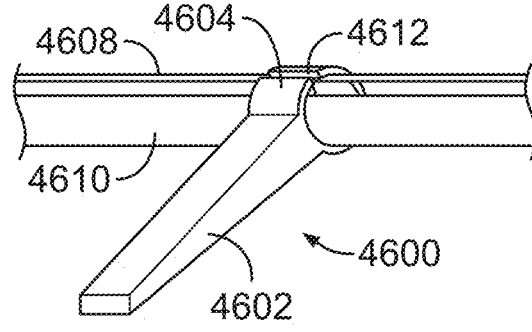

A bundling device may be a separate tool (completely separate from the main loading tool) or an integrated part of the loading tool as shown, for example, in FIG. 46. As shown, a loading tool 4600 can include an elongate shaft or rod 4602 that defines, at its distal end, a bundling tube 4604. The bundling tube 4604 is configured to receive and hold together various interventional devices, such as a guidewire 4608 and a therapeutic device 4610. The bundling device can be loaded onto the wire and shaft of the interventional device and can be removable. Thus, the bundling tube 4604 can contain a slit 4612 running parallel to the interventional device(s), which can be clipped onto the interventional device(s) and subsequently removed in a similar fashion. Loading and unloading a slit bundling tube can be performed in a similar manner as the loading/unloaded processes used to load/unload the slit support catheters described herein, but at a much smaller scale. The inner diameter of a bundling tube can be approximately 0.020 inches to 0.070 inches. The outer diameter can be approximately 0.030 inches to 0.080 inches. The length of the portion on the slit bundling tube that is loaded onto the guidewire and therapeutic device is approximately 0.050 cm minimum to approximately 35 cm maximum, which the preferred length being approximately 0.5 cm to 10 cm.

Figure 47:
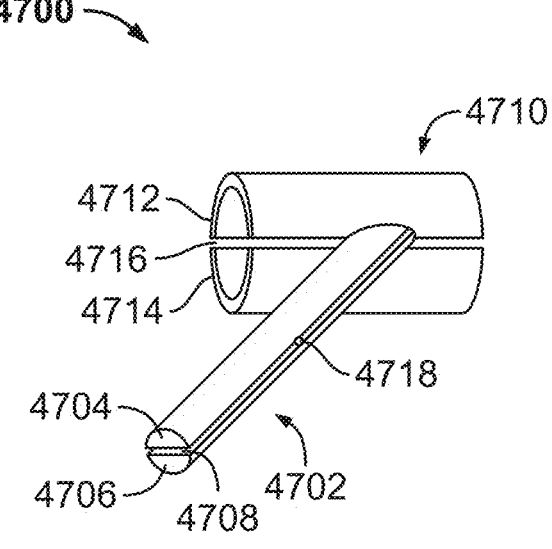

In some embodiments, there may be features that clip the loading tool temporarily onto the therapeutic device shaft (and guidewire shaft or bundle). This can include clips, magnets, or apposing features that result in locking the loading tool to the shaft in a temporary fashion, some examples of which are shown as components of the loading tool 4700 of FIG. 47. The loading tool 4700 includes a clam-shell loading rod 4702 comprised of a first portion 4704 and a second portion 4706, with an interface 4708 therebetween. A bundling tube 4710 is coupled or integrally formed with the loading rod 4702. The bundling tube 4710 can also have a clam-shell configuration featuring a first portion 4712 and a second portion 4714 with a gap or interface 4716 therebetween. A locking mechanism 4718 configured to lock the first and second portions of the rod and bundling tube together. Non-limiting examples of the locking mechanism 4718 may include a magnetic mechanism, a spring force clip, a mechanical lock, or a combination thereof.

Figure 48:
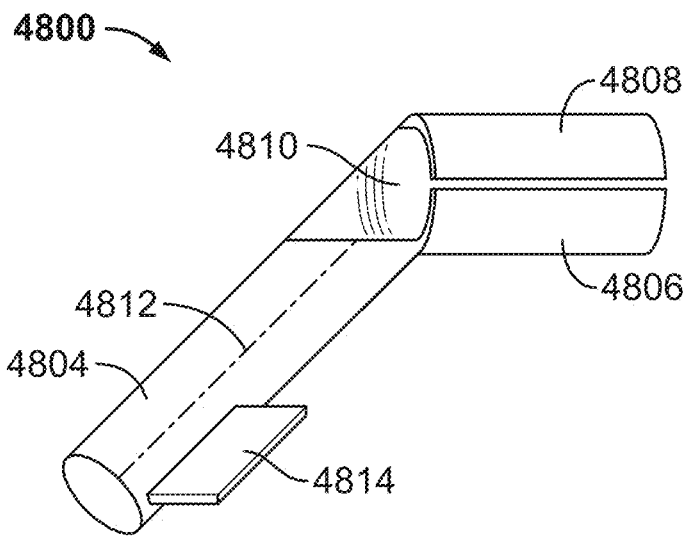

In some embodiments, a loading tool can be include a single tube that is slit and contains a hole and an optional handle (e.g., a single tubular loading tool). The loading tool 4800 shown in FIG. 48, for example, includes an angled tube 4802 comprised of proximal loading tube 4804 and a slit tube 4806 defining a longitudinal slit 4808. The slit tube 4806 can be configured to clip onto an interventional device inserted through the through-hole 4810 defined by the slit tube 4806. The length of the loading tube 4804 can be greater than the slit tube 4806 to allow grasping when the loading tube 4804 extends out of the slit tube 4806. The loading tube 4804 can also include a longitudinal slit 4812. In addition or alternatively, an optional handle 4814 can be included for grasping. The handle 4812 is shown near a proximal end of the loading tube 4804, but in additional embodiments it can be positioned on the slit tube 4806.

Figure 49:
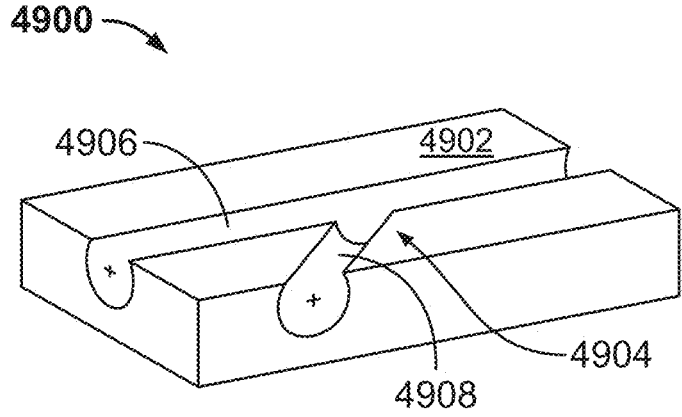

In some embodiments, troughs sized to receive interventional devices and support catheters may each include a countersink configured to prevent the devices from easily migrating out of the troughs. An example of such a device 4900 is shown in FIG. 49. The device 4900 includes a block-like body member 4902 defining a bifurcated trough 4904 comprised of a delivery trough 4906 and a loading trough 4908, both of which may be countersunk.

In additional or alternative embodiments, one or more of the aforementioned accessory devices can be supplemented or replaced by a single-use loading device comprising a clip member, for example. According to such embodiments, a user can use the clip member to clip a support catheter onto an in-place interventional device and then be removed.

The disclosed support catheters can be useful in performing a variety of medical procedures, including minimally invasive cardiac interventions, many of which involve the use of a guidewire and a guide catheter. A guidewire can comprise an elongate, small-diameter member designed to navigate vessels to reach a diseased site or vessel segment of interest. Guidewires can come in various configures, including solid steel or Nitinol core wires and/or solid core wire wrapped in a smaller wire coil or braid, for example. A guide catheter or sheath can comprise an elongate tube member defining a main lumen along its length. A guide catheter can be formed of polyurethane, for example, and can be shaped along its distal portion to facilitate advancement to a coronary ostium (or other region of interest within a patient's body). Any suitably sized guide catheter, such as a 6F, 7F, or 8F guide catheter, can be inserted at a femoral or radial artery and advanced through an aorta to a position adjacent to the ostium of a coronary artery.

One non-limiting example of an interventional medical procedure that can be performed using the devices disclosed herein, related in the pacemaker lead delivery, is described below. Optimal cardiac pacing increasingly requires exact positioning of pacemaker leads within chambers of the right heart and/or branches of the coronary venous system. Pacemaker leads are usually delivered via a regular sheath or a pre-shaped guide sheath placed via the cephalic or subclavian vein. These sheaths are often designed to be cut or split and peeled-away, once the lead is in position. The electrical connection of typical pacemaker leads are often notably larger than the shaft of various preexisting guide extension catheters. An expandable slit support catheter of the present disclosure with its distal end positioned close to the desired point of lead fixation may aid optimal pacemaker lead positioning and fixation. The disclosed support catheters can be especially advantageous when deploying a pacemaker to the left ventricle, through the patient-specific, anatomically variable coronary sinus.

In some embodiments, methods for delivering a pacemaker lead of the present disclosure can involve introducing a guide catheter or sheath 5000 into a blood vessel 5002 and advancing its distal end toward a region of interest 5003, as shown in FIG. 50A. For illustration, the blood vessel 5002 may include the arch of the aorta and the region of interest 5003 may include a chamber of the heart.

The guide sheath 5000, which is an elongate tube member defining a lumen, can have an internal capacity of 8F, 7F, or 6F, which are commonly used in interventional cardiology procedures. An expandable split support catheter 5004, with a full-length longitudinal slit and with or without a distal pre-set shape, can be positioned within the regular or pre-shaped guide sheath 5000 and extended therethrough until the distal end of the support catheter 5004 is at or near the region of interest 5003, as shown in FIG. 50B. At least one guidewire 5006 with a shaped distal end can be advanced through the sheath 5000 and the support catheter 5004, as shown in FIG. 50C. Alternatively, the guidewire 5006 can be preloaded into the support catheter 5004 outside the patient's body and both devices introduced together.

A smaller diameter catheter or "microcatheter" (straight or curved) 5008 can be loaded onto the guidewire 5006 and manipulated into a desired position within the region of interest 5003. The expandable split support catheter 5004 can be advanced over the guidewire 5006 and loaded onto the smaller diameter catheter 5008 close to the desired position as shown in FIG. 50D. The smaller diameter catheter 5008 can also be loaded onto the guidewire 5006 and support catheter 5004 outside the patient's body and the devices introduced together.

Once the target location is reached, the guidewire 5006 and smaller diameter catheter 5008 can be withdrawn and removed as shown in FIG. 50E. The pacemaker lead 5012 can then be advanced through the guide sheath 5000 and expandable split support catheter 5004 to a desired target position 5010 within the region of interest 5003, as shown in FIG. 50F. Further manipulation of the expandable split support catheter 5004 may aid final lead positioning and lead fixation. Once the pacemaker lead 5012 is fixed in position, the expandable split support catheter 5004 can be withdrawn and removed, for example in the peel-away manner described above, as shown in FIG. 50G. The pacemaker lead 5012 can remain seated at the target position 5010 to complete the interventional procedure.

In some embodiments, methods of the present disclosure can relate to bifurcation lesion PCI procedures. With some bifurcation PCI procedures, it is desirable to simultaneously inflate two treatment structures (e.g., balloons) within the coronary artery (or other vessel, in non-coronary procedures) to address vessel constriction at a bifurcation caused by the lesion, which may affect a main artery and an adjacent side branch. Treatment structures can include two angioplasty balloons, two stent delivery balloons, or one angioplasty balloon paired with one stent delivery balloon in some examples. To treat some lesions using at least two treatment balloons, a support catheter may be needed to deliver a first angioplasty or stent delivery balloon to the lesion. Compared to a guide catheter, a support catheter may reduce the cross-sectional lumen area available to deliver and inflate two treatment balloons. For example, two angioplasty or stent delivery balloons may not be advanceable through a current tubular (non-split) 5F-in-6F guide support catheter. Because of the space constraint associated with using a non-split support catheter, once the first angioplasty or stent delivery balloon has been successfully delivered to the lesion via the support catheter, the support catheter must be completely removed from the guide catheter before the second angioplasty or stent delivery balloon can be advanced through the guide catheter. When the first angioplasty or stent delivery balloon is positioned at the lesion, only a short length of proximal balloon shaft may remain outside of the guide catheter. When a non-split support catheter is withdrawn, leaving the first angioplasty or stent delivery balloon positioned at the lesion, there may be insufficient proximal balloon shaft length for the support catheter to be fully withdrawn from the guide catheter. The only way to remove a non-split support catheter (without first withdrawing the angioplasty or stent delivery balloon) and allow advancement of the second angioplasty or stent delivery balloon, may involve cutting the support catheter off the proximal balloon shaft.

A support catheter in the form of a guide extension catheter with a full length longitudinal slit of the present disclosure can solve the aforementioned problems by allowing easy removal of the support catheter between delivery of the first and second angioplasty or stent delivery balloons in a peel-away manner. For example, in some embodiments, methods of the present disclosure can include introducing guide catheter 5100 through an introducer or access sheath 5102 and advancing the guide catheter 5100 through a blood vessel 5104 toward a vessel bifurcation 5106 containing a lesion, as shown in FIG. 51A.

A first guidewire 5108 can be introduced through the access sheath 5102, extended through the guide catheter 5100 to the vessel bifurcation 5106, and extended distally within the main artery 5110 of the bifurcation, as shown in FIG. 51B.

A second guidewire 5112 can be introduced to the guide catheter 5100 and extended distally within a side-branch artery 5114 of the bifurcation 5106, as shown in FIG. 51C. Alternatively, a first guidewire 5108 may be inserted prior to or in conjunction with the guide catheter 5100, with the second guidewire 5112 optionally partially in the guide catheter 5100, or inserted subsequently.

A first balloon or stent delivery catheter 5116, which may not be configured to easily advance to the target site, can then be extended over the first guidewire 5108, as reflected by FIG. 51D.

An expandable split support catheter 5118 can be introduced and inserted distally within the artery 5104 over both wires 5108, 5112 and the first balloon or stent delivery catheter 5116 until the distal end of the support catheter 5118 is close to the bifurcation 5106, as shown in FIG. 51E.

A second balloon or stent delivery catheter can be introduced over one of the guidewires (the first guidewire 5108 in this example) and extended distally to the bifurcation lesion of the main artery 5110, which is shown ready for inflation or stent deployment in FIG. 51F. If simultaneous inflation of two balloons, two stent delivery catheters or one balloon and one stent delivery catheter is desired, the second balloon or stent delivery catheter cannot be advanced with the guide extension catheter 5118 in situ because of guide extension internal diameter constraints. Advantageously, the guide extension catheter 5118 can be withdrawn from the guide catheter 5100 and completely removed by detaching via the slit from the proximal catheter shaft of the first balloon or stent delivery catheter 5116 and first guidewire 5108 as shown in FIG. 51G. The second balloon or stent delivery catheter 5120 can be advanced over the second guidewire 5112 and extended distally to the bifurcation lesion as shown in FIG. 51H. Simultaneous balloon inflation is performed as shown in FIG. 51I. Both balloons 5116, 5120 can then be withdrawn.

Methods of the present disclosure can further relate to PCI or peripheral intervention to treat one or more lesions. In some embodiments, methods of the present disclosure can provide for treatment of lesions where need for a support catheter is not anticipated before the procedure begins. Such methods can include first introducing a guide catheter 5200 through an access sheath 5202 and into a blood vessel 5204, as shown in FIG. 52A. A guidewire 5206 can be placed and extended near or beyond a targeted lesion 5208, as shown in FIG. 51B. A therapeutic device 5210 can be inserted over the guidewire 5206 and therapy attempted as reflected by FIG. 52A.

The expandable split support catheter 5212, with a full length longitudinal slit 5214 and with or without a distal pre-set shape, can be loaded onto the therapy catheter shaft 5216 that extends proximal to the guide catheter 5200 or sheath 5202 as shown in FIG. 52B, without first needing to remove the therapeutic device 5210. Loading the expandable support catheter 5212 can be performed by urging open the slit 5214 and loading the entire tubular member 5218 of the support catheter onto the therapeutic device shaft 5216 via the slit. If the therapeutic device is a rapid-exchange device, the expandable split support catheter may need to be loaded over both the therapeutic device and the guidewire. A loading tool can be used during this process.

The support catheter 5212 is extended to the target lesion 5208 so that the proximal end 5220 of the tubular member 5218 remains in the guide catheter 5200. The distal end 5222 of the tubular member 5218 can be positioned near or across the lesion 5208, e.g., at the proximal side of the lesion, and the distal end 5224 of therapeutic device 5210 pushed across lesion 5208 as shown in FIG. 52C. If the distal end 5222 of the tubular member 5218 is advanced through and across the lesion 5208, it is withdrawn partially, with the therapeutic device 5210 remaining across the lesions. Therapy is then performed as in FIG. 52D, e.g., by expanding a balloon (with an optional stent) at a distal end of the interventional device. The expandable split support catheter 5212 can be withdrawn so that the split tubular member 5218 is partially or completely extending outside the proximal end of the guide catheter 5200 or sheath and support catheter is peeled off or removed from the therapeutic shaft 5216 and guidewire 5206 as shown in FIG. 52E. The therapeutic device 5210 can be used again (at the same lesion or another) or removed. At the end of the procedure, the guidewire 5206, guide catheter 5200 and access sheath 5202 are removed (or the guiding sheath is removed).

In other embodiments, methods of the present disclosure can provide for treatment of lesions where use of a support catheter is expected and can include first introducing an access sheath/guiding catheter or guiding sheath as shown in FIG. 51A. A guidewire is placed and extended near or beyond the lesion as shown in FIG. 51B.

The support catheters described herein can provide flexibility to interventional medical procedures in a manner that can enhance procedural efficiency and speed, while also reducing the difficulty commonly associated with procedures requiring navigation through tortuous portions of a patient's vasculature. Generally, a disclosed support catheter can be deployed during procedures that involve inserting a treatment device through a guide catheter after a guidewire has been extended across a blood vessel lesion, for example. The user performing the medical procedure may then realize that backup support is needed. Instead of removing the treatment device from the patient to make room for a support catheter, as done previously, a disclosed support catheter can be inserted over the shaft of the treatment device, advanced through the guide catheter, and optionally fully or partially over the treatment device. As a result, sufficient backup support can be provided quickly by the support catheter to allow the treatment device to be advanced distally to a location where, before insertion of the support catheter, was out of reach.

In some examples, a support catheter can be back-loaded onto an interventional device during a medical procedure. FIG. 53A depicts the back-loading of a support catheter 5300. As shown, the support catheter 5300 includes a tubular member 5302 defining a full-length longitudinal slit 5304 with or without a distal pre-set shape. The support catheter 5300 can be back-loaded over the distal end 5306 of a therapy catheter 5308, after which the two devices can be introduced together to a targeted lesion.

Alternatively, the support catheter 5300 can be introduced into a guide catheter 5310 over a guide wire 5312 and then the therapeutic device 5308 loaded and inserted through the support catheter 5300 and guide catheter 5310, as in FIG. 53B. The interventional device 5308 with the support catheter 5300 can be extended to the target lesion so that the proximal end 5314 of the tubular member 5302 remains in the distal end 5316 of the guide catheter 5310 near the lesion as reflected by FIG. 52C. Therapy is then performed, for example as in FIG. 52D. The support catheter 5300 can then be withdrawn so that the split tubular member 5302 is partially or completely extending outside the proximal end 5318 of the guiding catheter or sheath and the support catheter is peeled off or removed from the therapeutic shaft and guidewire, as shown for example in FIG. 52E. The therapeutic device can be used again or removed. At the end of the procedure, the guidewire, guiding catheter and access sheath are removed (or the guiding sheath is removed).

EXAMPLES

Although the present disclosure has been described with reference to preferred embodiments, those skilled in the art will recognize that changes can be made in form and detail without departing from the spirit and scope of the present disclosure. Accordingly, the above Detailed Description is intended to be illustrative and not restrictive. The above-described embodiments (or one or more features or components thereof) can be used in varying combinations with each other unless clearly stated to the contrary. Other embodiments can be used, such as by one of ordinary skill in the art upon viewing the above Detailed Description. Also, various features or components have been grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing as its own separate embodiment.

In Example 1, a device for use with a support catheter and at least one interventional device can include a body comprising an elongate delivery channel sized to receive and accommodate axial sliding of an interventional device. The device can also include an elongate loading structure sized to receive and accommodate axial sliding of a tubular member of the support catheter. A distal end of the elongate loading structure intersects the elongate delivery channel along a length of the elongate delivery channel.

In Example 2, the device of Example 1 can optionally be configured such that the elongate loading structure comprises a channel having a wedge-shaped protrusion extending along a length thereof. The cross-sectional dimension of the wedge-shaped protrusion varies along its length.

In Example 3, the device of Example 1 or Example 2 can optionally be configured such that a distal portion of the elongate delivery channel tapers to a smaller width than a proximal portion of the elongate delivery channel.

In Example 4, a device for use with a support catheter and at least one interventional device can include an elongate loading rod sized to be inserted within a tubular member of the support catheter. The elongate loading rod also has a distal end configured to couple with a shaft of an interventional device. The distal end of the elongate loading rod has a larger dimension than a proximal end of the elongate loading rod.

In Example 5, the device of Example 4 can optionally be configured to further include a handle protruding from a side of the elongate loading rod and configured for user engagement.

In Example 6, the device of Example 4 or 5 can optionally be configured such that the distal end of the elongate loading rod defines a cylindrical portion configured to bundle one or more interventional devices together.

In Example 7, the device of any one or any combination of Examples 4-6 can optionally be configured to further include two longitudinal components defining an interface therebetween. The two longitudinal components can be configured to separate along their lengths, thereby creating a longitudinal gap therebetween. The device can also include a locking mechanism configured to reduce a width of the longitudinal gap by bringing the longitudinal components closer together along their lengths.

In Example 8, a method for delivering two elongate medical devices to a lesion at a blood vessel bifurcation within a patient involves positioning a first guidewire and a second guidewire into a guide catheter and extending the first guidewire and the second guidewire to the blood vessel bifurcation. The method also involves positioning a first elongate medical device over the first guidewire and into the guide catheter and extending the first elongate medical device to the blood vessel bifurcation. The method also involves positioning a support catheter comprising a tubular member over the first and second guidewires and onto the first elongate medical device by urging a portion of the elongate medical device into a lumen defined by the tubular member, the tubular member including a longitudinal slit. The method also involves advancing the first elongate medical device distally until a distal treatment structure of the first elongate medical device is positioned at the lesion.

In Example 9, a method for treating a lesion in a blood vessel using an elongate medical device involves positioning a first guidewire into a guide catheter and extending the first guidewire distally beyond the lesion. The method also involves positioning a first elongate medical device over the guidewire and into the guide catheter and extending the first elongate medical device distally until a distal treatment structure of the first elongate medical device is positioned at a proximal side of the lesion. The method also involves positioning a support catheter comprising a tubular member over the first guidewire and onto a proximal or intermediate portion of the elongate medical device by urging the proximal or intermediate portion of the elongate medical device into a lumen defined by the tubular member, the tubular member including a longitudinal slit.

In Example 10, the method of Example 9 can optionally be configured to further involve advancing the tubular member of the support catheter along the elongate medical device until the tubular member is positioned at the proximal side of the lesion, proximal to the treatment structure, and advancing the treatment structure of the elongate medical device distally to or beyond the lesion.

In Example 11, the method of Example 10 can optionally be configured to further involve inflating a balloon of the treatment structure.

In Example 12, the method of Example 11 can optionally be configured to further involve removing the support catheter by withdrawing the tubular member proximally and peeling the tubular member from the proximal or intermediate portion of the elongate medical device via the longitudinal slit.

In Example 13, a guide extension catheter for use with a guide catheter includes an elongate tube member having or coupled with an angled proximal port and defining a longitudinal slit and a lumen and having an outer diameter smaller than a lumen of the guide catheter. The guide extension catheter also includes a push member eccentrically coupled relative to an axis of the tube member and extending proximal of the tube member for slidably positioning the tube member within and partially beyond a distal end of the guide catheter.

In Example 14, the guide extension catheter of Example 13 can optionally be configured such that the outer diameter of the elongate tube member tapers distally, such that the outer diameter is smaller at a distal portion of the elongate tube member than at a proximal portion of the elongate tube member.

In Example 15, the guide extension catheter of Example 14 can optionally be configured such that the distal portion of the elongate tube member comprises a flexible, tapered distal tip configured to fold proximally into the distal portion of the elongate tube member.

In Example 16, the guide extension catheter of any one or any combination of Examples 13-15 can optionally be configured such that a width of the longitudinal slit varies along a length thereof.

In Example 17, the guide extension catheter of Example 16 can optionally be configured such that the longitudinal slit comprises two or more cutout portions, each having a greater width relative to a remainder of the longitudinal slit.

In Example 18, the guide extension catheter of any one or any combination of Examples 13-17 can optionally be configured such that the push member comprises a flattened portion embedded in at least a portion of the elongate tube member.

In Example 19, the guide extension catheter of any one or any combination of Examples 13-18 can optionally be configured such that a distal portion of the elongate tube member is curved.

In Example 20, the guide extension catheter of any one or any combination of Examples 13-19 can optionally be configured such that the elongate tube member comprises at least one stent-like metal frame having a first interdigitating component at a first end and a second interdigitating component at a second end, the first interdigitating component complementary to the second interdigitating component.

Closing Notes

The above Detailed Description includes references to the accompanying drawings, which form a part of the Detailed Description. The Detailed Description should be read with reference to the drawings. The drawings show, by way of illustration, specific embodiments in which the present support catheters, loading components, and related methods can be practiced. These embodiments are also referred to herein as "examples."

Certain terms are used throughout this patent document to refer to particular features or components. As one skilled in the art appreciates, different people may refer to the same feature or component by different names. This patent document does not intend to distinguish between components or features that differ in name but not in function.

For the following defined terms, certain definitions shall be applied unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." All numeric values are assumed to be modified by the term "about," whether or not explicitly indicated. The term "about" generally refers to a range of numbers that one of skill in the art would consider equivalent to the recited value (e.g., having the same function or result). In many instances, the term "about" can include numbers that are rounded to the nearest significant figure. The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.). The terms "patient" and "subject" are intended to include mammals, such as for human or veterinary applications. The terms "distal" and "proximal" are used to refer to a position or direction relative to the treating clinician. "Distal" and "distally" refer to a position that is distant from, or in a direction away from, the treating clinician. "Proximal" and "proximally" refer to a position that is near, or in a direction toward, the treating clinician.

The scope of the invention should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, a device, kit or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A guide extension catheter for use with a guide catheter, comprising:
   an elongate tube member having a longitudinal slit, a lumen, and an outer diameter smaller than a lumen of the guide catheter, the elongate tube member further having or coupled with an angled proximal port; and
   a push member eccentrically coupled relative to an axis of the elongate tube member and extending proximal of the elongate tube member for slidably positioning the elongate tube member within and partially beyond a distal end of the guide catheter,
   wherein the longitudinal slit includes a straight portion and at least one slanted or curved portion relative to the axis of the elongate tube member, the at least one slanted or curved portion located distal to the straight portion.

2. The guide extension catheter of claim 1, wherein the outer diameter of the elongate tube member tapers distally, such that the outer diameter is smaller at a distal portion of the elongate tube member than at a proximal portion of the elongate tube member.

3. The guide extension catheter of claim 2, wherein the distal portion of the elongate tube member comprises a flexible, tapered distal tip configured to fold proximally into the lumen of the elongate tube member.

4. The guide extension catheter of claim 1, wherein a width of the longitudinal slit varies along a length of the elongate tube member.

5. The guide extension catheter of claim 1, wherein the push member comprises a flattened portion embedded in at least a portion of the elongate tube member.

6. The guide extension catheter of claim 5, wherein the flattened portion of the push member extends substantially an entire length of the elongate tube member.

7. The guide extension catheter of claim 1, wherein a distal portion of the elongate tube member is curved.

8. The guide extension catheter of claim 1, wherein the longitudinal slit is configured to accommodate an exchange of an interventional device into and out of the lumen of the elongate tube member.

9. The guide extension catheter of claim 1, wherein the at least one slanted or curved portion spans a length of 0.25 centimeters to 3 centimeters, inclusive.

10. The guide extension catheter of claim 1, wherein the elongate tube member comprises a frame defined by a longitudinal spine and a plurality of prongs extending from the longitudinal spine.

11. The guide extension catheter of claim 1, wherein the angled proximal port is defined by a slanted wall, a collar, or a concave track extending from the push member to a fully cylindrical portion of the elongate tube member.

12. The guide extension catheter of claim 1, wherein the push member is coupled to the elongate tube member at a location opposite a location of the longitudinal slit.

* * * * *